(12) United States Patent
Szarka et al.

(10) Patent No.: US 7,098,383 B2
(45) Date of Patent: Aug. 29, 2006

(54) METHODS FOR THE PRODUCTION OF MULTIMERIC IMMUNOGLOBULINS, AND RELATED COMPOSITIONS

(75) Inventors: Steven Szarka, Calgary (CA); Gijs Van Rooijen, Calgary (CA); Maurice Moloney, Calgary (CA)

(73) Assignee: SemBioSys Genetics Inc., Calgary (CA)

( * ) Notice: Subject to any disclaimer, the term of this patent is extended or adjusted under 35 U.S.C. 154(b) by 421 days.

(21) Appl. No.: 10/176,380

(22) Filed: Jun. 21, 2002

(65) Prior Publication Data

US 2003/0093832 A1    May 15, 2003

Related U.S. Application Data

(63) Continuation-in-part of application No. 10/032,201, filed on Dec. 19, 2001, now abandoned, which is a continuation-in-part of application No. 10/006,038, filed on Dec. 4, 2001, now abandoned.

(60) Provisional application No. 60/302,885, filed on Jul. 5, 2001, provisional application No. 60/331,363, filed on Dec. 19, 2000.

(51) Int. Cl.
  *C12N 15/82* (2006.01)
  *C12N 15/13* (2006.01)
  *C12N 15/62* (2006.01)
  *C12N 5/10* (2006.01)
  *A01H 5/00* (2006.01)

(52) U.S. Cl. .................... 800/288; 800/260; 800/278; 800/281; 800/287; 435/69.6; 435/69.7; 435/69.8; 435/419; 435/468; 536/23.4; 536/23.53

(58) Field of Classification Search ............... 800/260, 800/278, 281, 287, 288; 435/69.6–69.8, 435/419, 468, 69.9; 536/23.4, 23.53
See application file for complete search history.

(56) References Cited

U.S. PATENT DOCUMENTS

| | | | |
|---|---|---|---|
| 4,954,618 A | 9/1990 | Fahnestock |
| 5,151,350 A | 9/1992 | Colbert et al. |
| 5,202,422 A | 4/1993 | Hiatt et al. |
| 5,639,947 A | 6/1997 | Hiatt et al. |
| 5,650,554 A | 7/1997 | Moloney |
| 5,856,452 A | 1/1999 | Moloney et al. |
| 5,959,177 A | 9/1999 | Hein et al. |
| 5,965,390 A | 10/1999 | Björck et al. |
| 6,146,645 A | 11/2000 | Deckers et al. |
| 6,183,762 B1 | 2/2001 | Deckers et al. |
| 6,210,742 B1 | 4/2001 | Deckers et al. |
| 6,372,234 B1 | 4/2002 | Deckers et al. |
| 6,417,429 B1 | 7/2002 | Hein et al. |
| 6,509,453 B1 | 1/2003 | Moloney et al. |

OTHER PUBLICATIONS

Turk et al. New Phytologist 136(1): 29-38 (1997).*
Smeekens et al. Plant Molecular Biology 9(4): 377-388 (1987).*
Hiatt et al. Nature 342: 76-78 (Nov. 1989).*
Hiatt et al. FEBS Letters 307(1): 71-75 (Jul. 1992).*
De Neve et al. Molecular and General Genetics 260(6): 582-592 (1999).*
During et al. Plant Molecular Biology 15: 281-293 (1990).*
Van Rooijen, "Covalent and Non-covalent binding of proteins to oil bodies", 2000, ISPMB (Quebec).

* cited by examiner

*Primary Examiner*—David T. Fox
(74) *Attorney, Agent, or Firm*—Micheline Gravelle; Bereskin & Parr

(57) ABSTRACT

Improved methods for the production of multimeric-protein-complexes, such as redox proteins and immunoglobulins, in association with oil bodies are described. The redox protein is enzymatically active when prepared in association with the oil bodies. Also provided are related nucleic acids, proteins, cells, plants, and compositions.

69 Claims, 9 Drawing Sheets

FIGURE 1

| Class | Heterodimer | Example sequence reference for heterodimeric subunits |
|---|---|---|
| Biosynthetic | 3-methyl-2-oxobutanoate dehydrogenase (2-oxoisovalerate dehydrogenase (lipoamide))- E1 component) | McKean, et al. Biochim. Biophys. Acta (1992) 1171:109-112 / Chuang,J.L., et al.. FEBS Lett. A (1990) 262 (2), 305-309. |
| Biosynthetic | 3-oxoadipate CoA-transferase | Parales, R.E. and Harwood, S.C. J. Bacteriol. (1992) 174:4657-4666 |
| Biosynthetic | anthranilate synthase:indole-3-glycerol phosphate synthase | Zalkin, H.; et al. J. Biol. Chem. (1984) 259:3985-3992 . |
| Biosynthetic | beta-ketoacyl-[acyl carrier protein] synthase I | Siggaard-Andersen, M. et al. Proc. Natl. Acad. Sci. U.S.A. (1991) 88:4114-4118 |
| Biosynthetic | butyrate—acetoacetate CoA-transferase | Fischer,R.J., et al. J. Bacteriol. (1993) 175 (21), 6959-6969. |
| Biosynthetic | amp dependent protein kinase | Mutzel, R et al. Proc. Natl. Acad. Sci. U.S.A. (1987) 84:6-10./ Burki,E., et al. Gene (1991) 102 (1), 57-65. |
| Biosynthetic | carbamoyl-phosphate synthase | Shigenobu,S., et al. Nature. (2000) 407 (6800), 81-86. |
| Biosynthetic | Creatine kinase | Billadello, J.J.; et al. Biochem. Biophys. Res. Commun. (1986) 138:392-398. / Roman, D.; et al. Proc. Natl. Acad. Sci. U.S.A. (1985) 82:8394-8398. |
| Biosynthetic | gamma-glutamyltransferase (gamma-glutamyl transpeptidase) | Papandrikopoulou, A.; et al. Eur. J. Biochem. (1989) 183:693-698. |
| Biosynthetic | glutathione transferase | Morrow, C.S. et al. Gene (1989) 75:3-11 |
| Biosynthetic | glycerol-3-phosphate dehydrogenase | Cole, S.T. et al. J. Bacteriol. (1988) 170:2448-2456. |
| Biosynthetic | guanylate cyclase | Hinsch, K.D. et al. FEBS Lett. (1988) 239:29-34/ Koesling, D. et al. FEBS Lett. (1990) 266:128-132. |
| Biosynthetic | heterodisulfide reductase | Smith,D.R., et al. J. Bacteriol. (1997) 179 (22), 7135-7155. |
| Biosynthetic | human cathepsin | Ritonja, A. et al. FEBS Lett. (1988) 228:341-345. |
| Biosynthetic | Hydrogenase | Menon, N.K. et al. J. Bacteriol. (1990) 172:1969-1977. |
| Biosynthetic | Meprin A | Johnson, G.D. and Hersh, L.B. J. Biol. Chem. (1992) 267:13505-13512. |
| Biosynthetic | methionine adenosyltransferase | Horikawa, S.; Tsukada, K. FEBS Lett. (1992) 312:37-41. |
| Biosynthetic | methylmalonyl-CoA mutase | Jackson, C.A. et al. Gene (1995) 167:127-132. |
| Biosynthetic | mitochondrial processing peptidase | Pollock, R.A. et al. EMBO J. (1988) 7:3493-3500. |
| Biosynthetic | Na+/K+-exchanging ATPase | Shull,G.E., et al. Biochemistry (1986) 25 (25), 8125-8132./Mercer,R.W., et al. Mol. Cell. Biol. (1986) 6 (11), 3884-3890./ Mercer,R.W., et al. J. Cell Biol. (1993) 121 (3), 579-586. |
| Biosynthetic | NAD(+)-dependent isocitrate dehydrogenase | Cupp, J.R. and McAlister-Henn, L. J. Biol. Chem. (1992) 267:16417-16423. /Cupp, J.R. and McAlister-Henn, L. J. Biol. Chem. (1991) 266:22199-22205. |

FIGURE 1 (cont'd)

| | | |
|---|---|---|
| Biosynthetic | phosphoribosylformylglycinamidine synthase | Ebbole, D.J.; Zalkin, H. J. Biol. Chem. (1987) 262:8274-8287. |
| Biosynthetic | protocatechuate 3,4-dioxygenase | Frazee, R.W.; et al. J. Bacteriol. (1993) 175:6194-6202. |
| Biosynthetic | S-100 protein | Engelkamp, D.; et al. Biochemistry (1992) 31:10258-10264. / Allore, R.J.; et al. J. Biol. Chem. (1990) 265:15537-15543. |
| Biosynthetic | sucrose--fructan 6-fructosyltransferase | Sprenger, N.; et al. Proc. Natl. Acad. Sci. U.S.A. (1995) 92:11652-11656. |
| Biosynthetic | Superoxide dismutase | Capo, C.R.; et al. Biochem. Biophys. Res. Commun. (1990) 173:1186-1193. |
| Biosynthetic | Urease | Labigne, A.; et al. J. Bacteriol. (1991) 173:1920-1931. |
| Biosynthetic | urokinase-type plasminogen activator (urokinase) | Belin, D. et al. Eur. J. Biochem. (1985) 148:225-232. |
| Biosythetic | methylmalonyl-coenzyme A mutase | Birch,A., et al.. J. Bacteriol. (1993) 175 (11), 3511-3519. |
| Calcium binding | Calcineurin | Muramatsu,T. and Kincaid,R.L. Biochim. Biophys. Acta (1993) 1178 (1), 117-120 / Guerini, D. et al. DNA (1989) 8:675-682. |
| Calcium binding | Calgranulin | Imamichi, T. et al. Biochem. Biophys. Res. Commun. (1993) 194:819-825. |
| Calcium binding | Calpain | Aoki, K. et al. FEBS Lett. (1986) 205:313-317. |
| DNA binding | AP1 | van Straaten,F., et al. Proceedings of the National Academy of Sciences of the United States of America. (1983) 80 (11), 3183-3187. /Hattori,K., et al Proceedings of the National Academy of Sciences of the United States of America. (1988) 85 (23), 9148-9152. |
| DNA binding | cMyc-Max | Schreiber-Agus,N et al. Mol. Cell. Biol. (1993) 13 (5), 2765-2775. |
| DNA binding | DNA binding protein HU-1/HU-2 | Laine, B. et al. Eur. J. Biochem. (1980) 103:447-461. |
| DNA binding | hepatic nuclear factor 1 | Bach,I. et al. Nucleic Acids Res. (1992) 20 (16), 4199-4204. / Rey-Campos,J. et al. EMBO J. (1991) 10 (6), 1445-1457. |
| DNA binding | Integration host factor | Miller,H.I. Cold Spring Harbor symposia on quantitative biology. (1984) 49, 691-698. / Flamm, E. and Weisberg, R.A. J. Mol. Biol. (1985) 183:117-128. |
| DNA binding | Ku | Reeves,W.H. and Sthoeger,Z.M. J. Biol. Chem. (1989) 264 (9), 5047-5052. / J. Biol. Chem. (1989) 264 (23), 13407-13411. |
| DNA binding | MutS | Bocker et al. 1999. Cancer Research 59, 816-822. |
| DNA binding | NF-E2 | Chan,J.Y. et al.. Proc. Natl. Acad. Sci. U.S.A. (1993) 90 (23), 11366-11370./ Toki,T., et al. Oncogene (1997) 14 (16), 1901-1910. |
| DNA binding | nuclear factor kB (NFkB) | Kieran M, et al. Cell. (1990) Sep 7;62(5):1007-18. / Ruben SM, et al. Science (1991) Mar 22;251(5000):1490-3. Erratum in: Science (1991) Oct 4;254(5028):11 |
| Electron transport | corrinoid/iron-sulfur protein | Lu, W.P. et al. J. Biol. Chem. (1993) 268:5605-5614. |

FIGURE 1 (cont'd)

| | | |
|---|---|---|
| Electron transport | cytochrome d ubiquinol oxidase | Green, G.N. et al. J. Biol. Chem. (1988) 263:13138-13143. |
| Electron transport | cytochrome-c3 hydrogenase | Menon, N.K. et al. J. Bacteriol. (1987) 169:5401-5407. |
| Electron transport | electron transfer flavoprotein | Finocchiaro, G. et al. Biol. Chem. (1988) 263:15773-15780. / Finocchiaro, G. et al. Eur. J. Biochem. (1993) 213:1003-1008. |
| Electron transport | xylene monooxygenase | Shaw, J.P. and Harayama, S. Eur. J. Biochem. (1992) 209:51-61. / Kasai,Y., et al. J. Bacteriol. (2001) 183 (22), 6662-6666. |
| Growth factor | hepatocyte growth factor | Nakamura, T. et al. Nature (1989) 342:440-443. |
| Growth factor | human chorionic gonadotropin | Morgan,F.J. et al. J. Biol. Chem. (1975) 250 (13), 5247-5258. |
| Growth factor | Platelet-derived growth factor | Takimoto,Y., et al. Hiroshima J. Med. Sci. (1993) 42 (1), 47-52./ Josephs,S.F., et al. Science (1984) 225 (4662), 636-639. |
| Hormone | Bombyxin | Adachi, T. et al. J. Biol. Chem. (1989) 264:7681-7685. |
| Hormone | Follicle stimulating hormone | Fiddes,J.C. and Goodman,H.M. J. Mol. Appl. Genet. (1981) 1 (1), 3-18. / Watkins,P.C., et al. DNA (1987) 6 (3), 205-212. |
| Hormone | Insulin | Bell,G.I., Pictet,R.L., Rutter,W.J., Cordell,B., Tischer,E. and Goodman,H.M. Sequence of the human insulin gene. Nature. 284 (5751), 26-32 (1980) |
| Hormone | Luteinizing Hormone | Fiddes,J.C. and Goodman,H.M. J. Mol. Appl. Genet. (1981) 1 (1), 3-18. / Shome,B. and Parlow,A.F. J. Clin. Endocrinol. Metab. (1973) 36 (3), 618-621. |
| Hormone | Thyroid stimulating hormone | Fiddes,J.C. and Goodman,H.M. J. Mol. Appl. Genet. (1981) 1 (1), 3-18. / Hayashizaki Y, et al. FEBS Lett. (1985) 188 (2), 394-400. |
| Immune | B-cell antigen receptor complex | Hashimoto,S. et al. J. Immunol. (1993) 150 (2), 491-498. / Flaswinkel,H. and Reth,M. Immunogenetics (1992) 36 (4), 266-269. |
| Immune | Cell surface CD8 molecules | Ureta-Vidal,A., et al. Immunogenetics (1999) 49 (7-8), 718-721. |
| Immune | human complement subcomponent C1q | Sellar, G.C. et al. Biochem. J. (1991) 274:481-490. |
| Immune | T cell receptor | Talken,B.L. et al. Scand. J. Immunol. (2001) 54 (1-2), 204-210. |
| Photosynthesis | C-phycocyanin | Offner, G.D. et al. J. Biol. Chem. (1981) 256:12167-12175. / Troxler, R.F. et al. J. Biol. Chem. (1981) 256:12176-12184. |
| Photosynthesis | ferroredoxin-thioredoxin reductase | Chow, L.P. et al. Eur. J. Biochem. (1995) 231:149-156. / Iwadate, H. et al. Eur. J. Biochem. (1994) 223:465-471. |
| Photosynthesis | Light harvesting complex I | Proc. Natl. Acad. Sci. U.S.A. (1984) 81, 189-192. |
| Photosynthetic | cytochrome b559 | Carrillo, N. et al. Curr Genet. 1986;10(8):619-24. |

FIGURE 1 (cont'd)

| | | |
|---|---|---|
| Protease | ATP-dependent Clp protease | Gerth, U. et al. Gene (1996) 181:77-83. / Kunst,F. et al. Nature (1997) 390 (6657), 249-256. |
| Receptor | alpha-2-macroglobulin receptor | Strickland, D.K. et al. J. Biol. Chem. (1990) 265:17401-17404. / Strickland, D.K. et al. J. Biol. Chem. (1991) 266:13364-13369. |
| Receptor | Interleukin-2 receptor | Ishida, N. et al. Nucleic Acids Res. (1985) 13:7579-7589. / Hatakeyama, M. et al. Science (1989) 244:551-556 / Takeshita, T. et al. Science (1992) 257:379-382. |
| Receptor | platelet-derived growth factor receptor | Lee, K.H. et al. Mol. Cell. Biol. (1990) 10:2237-2246. / Herren,B. et al. Biochim. Biophys. Acta 1173 (3), 294-302 (1993). |
| Structural | Hemoglobin | Heindell,H.C. et al. Cell (1978) 15 (1), 43-54. / Best,J.S. et al. Hoppe-Seyler's Z. Physiol. Chem. (1989) 350 (5), 563-580. / Hardison,R.C. J. Biol. Chem. (1981) 256 (22), 11780-11786. |
| Structural | human platelet glycoprotein Ib | Wenger,R.H. et al. Biochem. Biophys. Res. Commun. (1988) 156 (1), 389-395. / Yagi,M. et al. J. Biol. Chem. (1994) 269 (26), 17424-17427. |
| Structural | Plasma fibronectin | Kornblihtt, A.R. et al. Proc. Natl. Acad. Sci. U.S.A. (1983) 80:3218-3222. |
| Structural | Spectrin | Sahr, K.E. et al. J. Biol. Chem. (1990) 265:4434-4443. / Winkelmann, J.C. et al. J. Biol. Chem. (1990) 265:11827-11832. |
| Structural | Tubulin | Ponstingl, H. et al. Proc. Natl. Acad. Sci. U.S.A. (1981) 78:2757-2761. / Krauhs, E. et al. Proc. Natl. Acad. Sci. U.S.A. (1981) 78:4156-4160. |
| Toxin | Agkisacutacin | Cheng,X. et al. Biochem. Biophys. Res. Commun. (1999) 265 (2), 530-535. |
| Toxin | Beta bungarotoxins | Kondo, K. et al. J. Biochem. (1978) 83:101-115. |
| Toxin | Crotoxin | Bouchier,C. et al. Nucleic Acids Res. (1988) 16 (18), 9050. |
| Toxin | Mojave toxin | John, T.R. et al. Gene (1994) 139:229-234. |
| Toxin | venom protein C9S3 | Rowan, E.G. et al. Nucleic Acids Res. (1990) 18:1639. / Joubert, F.J. and Viljoen, C.C. Hoppe-Seyler's Z. Physiol. Chem. (1979) 360:1075-1090. |
| Miscellaneous | Inhibin | Forage, R.G. et al. Proc. Natl. Acad. Sci. U.S.A. (1986) 83:3091-3095. |
| Miscellaneous | Monellin | Frank, G. and Zuber, H. Hoppe-Seyler's Z. Physiol. Chem. (1976) 357:585-592. |
| Miscellaneous | mRNA capping enzyme | Niles, E.G. et al., J. Virology (1986) 153:96-112. |
| Miscellaneous | Soybean insulin-binding protein si30 | Barbashov, S.F. et al. Bioorg. Khim. (1991) 17:421-423. |

FIGURE 3
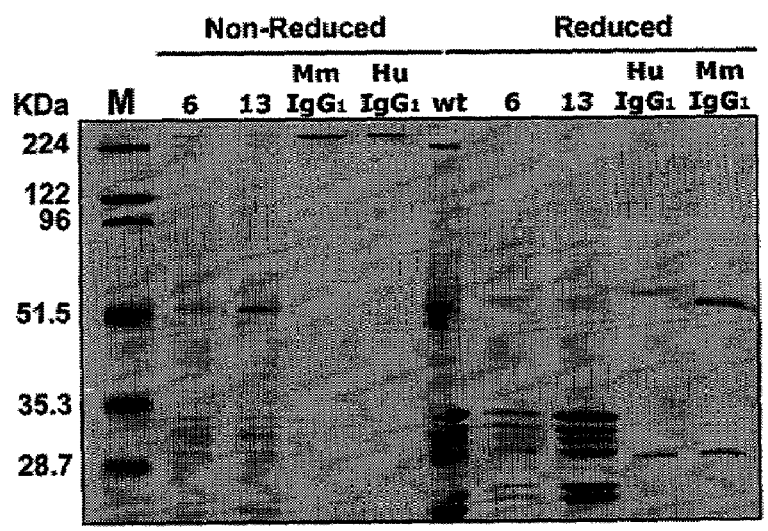
Coomassie Stained Gel
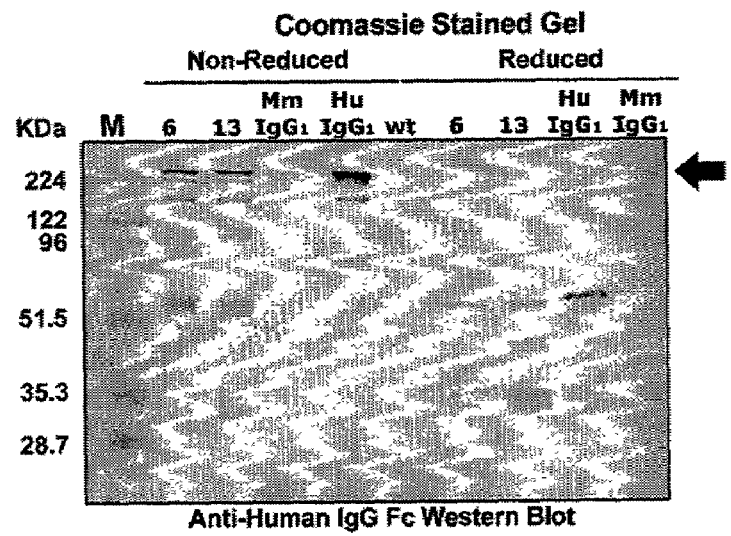
Anti-Human IgG Fc Western Blot
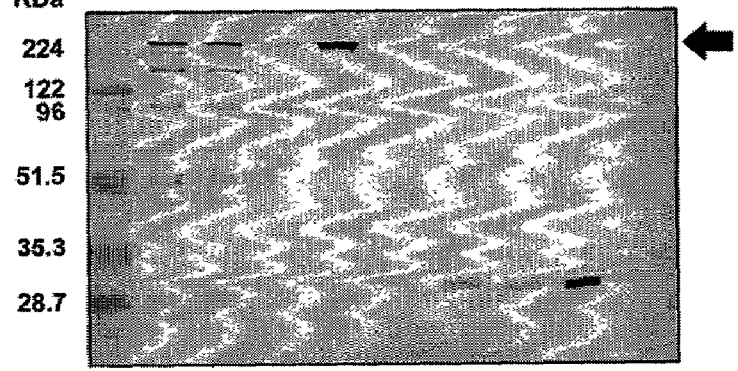
Anti-Human Kappa Western Blot

FIGURE 4

```
  1  AQHDEAQQNA FYQVLNMPNL NADQRNGFIQ SLKDDPSQSA NVLGEAQKLN
 51  DSQAPKADAQ QNNFNKDQQS AFYEILNMPN LNEAQRNGFI QSLKDDPSQS
101  TNVLGEAKKL NESQAPKADN NFNKEQQNAF YEILNMPNLN EEQRNGFIQS
151  LKDDPSQSAN LLSEAKKLNE SQAPKADNKF NKEQQNAFYE ILHLPNLNEE
201  QRNGFIQSLK DDPSQSANLL AEAKKLNDAQ APKADNKFNK EQQNAFYEIL
251  HLPNLTEEQR NGFIQSLKDD PSVSKEILAE AKKLNDAQAP KEEDN
```

FIGURE 5

```
          M  A  Q  H  D  E  A  Q  Q  N  A  F  Y  Q  V  L  N  M
  1   GCGCCATGGCACAGCATGATGAAGCACAGCAGAATGCTTTCTACCAGGTGCTCAACATGC
        P  N  L  N  A  D  Q  R  N  G  F  I  Q  S  L  K  D  D  P  S
 61   CCAATTTAAATGCTGATCAACGTAACGGCTTCATCCAATCGCTTAAAGACGACCCTTCCC
        Q  S  A  N  V  L  G  E  A  Q  K  L  N  D  S  Q  A  P  K  A
121   AGAGCGCTAATGTCCTCGGCGAAGCTCAAAAGCTGAACGACAGCCAAGCTCCAAAAGCGG
        D  A  Q  Q  N  N  F  N  K  D  Q  Q  S  A  F  Y  E  I  L  N
181   ATGCTCAACAGAACAACTTCAACAAAGATCAACAGTCAGCCTTTTACGAGATCCTTAATA
        M  P  N  L  N  E  A  Q  R  N  G  F  I  Q  S  L  K  D  D  P
241   TGCCCAACCTCAACGAGGCCCAGCGTAATGGTTTCATCCAATCTCTTAAGGACGACCCAT
        S  Q  S  T  N  V  L  G  E  A  K  K  L  N  E  S  Q  A  P  K
301   CGCAGTCGACCAACGTTTTGGGTGAAGCTAAGAAGCTAAACGAGTCACAGGCTCCTAAAG
        A  D  N  N  F  N  K  E  Q  Q  N  A  F  Y  E  I  L  N  M  P
361   CTGATAACAACTTCAACAAGGAGCAGCAGAACGCCTTCTATGAAATCCTCAACATGCCGA
        N  L  N  E  E  Q  R  N  G  F  I  Q  S  L  K  D  D  P  S  Q
421   ATCTCAACGAGGAACAGCGAAACGGGTTCATCCAGAGTCTTAAAGATGACCCATCCCAAT
        S  A  N  L  L  S  E  A  K  K  L  N  E  S  Q  A  P  K  A  D
481   CCGCTAACCTTCTGTCTGAAGCTAAGAAGCTAAACGAGAGCCAGGCGCCCAAAGCCGACA
        N  K  F  N  K  E  Q  Q  N  A  F  Y  E  I  L  H  L  P  N  L
541   ACAAGTTTAACAAGGAGCAACAGAACGCCTTCTATGAAATTCTGCATCTCCCTAATCTCA
        N  E  E  Q  R  N  G  F  I  Q  S  L  K  D  D  P  S  Q  S  A
601   ACGAGGAACAACGTAACGGTTTCATCCAATCGCTTAAGGATGATCCGAGTCAATCCGCAA
        N  L  L  A  E  A  K  K  L  N  D  A  Q  A  P  K  A  D  N  K
661   ACTTGTTGGCGGAGGCCAAGAAACTGAACGACGCGCAAGCACCAAAAGCTGATAACAAGT
        F  N  K  E  Q  Q  N  A  F  Y  E  I  L  H  L  P  N  L  T  E
721   TCAACAAGGAACAACAGAATGCTTTCTACGAGATACTTCACTTGCCAAATCTCACTGAGG
        E  Q  R  N  G  F  I  Q  S  L  K  D  D  P  S  V  S  K  E  I
781   AACAAAGAAACGGCTTCATCCAGAGTTTGAAGGATGACCCGTCTGTCAGCAAGGAGATAC
        L  A  E  A  K  K  L  N  D  A  Q  A  P  K  E  E  D  N  A  M
841   TAGCTGAGGCGAAGAAGTTGAACGATGCGCAAGCTCCGAAGGAGGAGGACAATGCCATGG

901   GCGC
```

US 7,098,383 B2

METHODS FOR THE PRODUCTION OF MULTIMERIC IMMUNOGLOBULINS, AND RELATED COMPOSITIONS

RELATED APPLICATIONS

This application is a continuation-in-part of application Ser. No. 10/032,201 filed 19 Dec. 2001, now abandoned; which is a continuation-in-part of application Ser. No. 10/006,038 filed Dec. 4, 2001, now abandoned. Application Ser. No. 10/032,201 claims benefit of Provisional Application No. 60/302,885 filed Jul. 5, 2001 application Ser. No. 10/006,038 claims benefit to Provisional Application No. 60/331,363 filed 19 Dec. 2000. The subject matter of each of the applications is incorporated herein by reference in its entirety.

FIELD OF THE INVENTION

The present invention relates to multimeric-protein-complexes, redox proteins, immunoglobulins and recombinant polypeptides; and improved methods for their production.

BACKGROUND OF THE INVENTION

Multimeric proteins (i.e. proteins comprising multiple polypeptide chains) are a biologically and commercially important class of proteins. Antibodies for example are multimeric proteins which are used to treat a wide range of disease conditions. However in view of their complexity, multimeric proteins frequently represent significant manufacturing challenges.

Redox proteins are also a commercially important class of proteins with applications in a variety of different industries including the pharmaceutical, personal care and food industry. For example, the redox protein thioredoxin may be used in the manufacture of personal care products (Japanese Patent Applications JP9012471A2, JP103743A2, JP1129785A2), pharmaceutical compositions/products (Aota et al. (1996) J. Cardiov. Pharmacol. (1996) 27: 727–732) as well as to reduce protein allergens present in food products such as milk (del Val et al. (1999) J. Allerg. Vlin. Immunol. 103: 690–697) and wheat (Buchanan et al. (1997) Proc. Natl. Acad. Sci. USA 94: 5372–5377).

However, there is a need in the art to further improve the methods for the recombinant expression of multimeric proteins, including redox proteins and immunoglobulins. The present invention satisfies this need and provides related advantages as well.

SUMMARY OF THE INVENTION

The present invention relates to novel and improved methods of producing a first and/or second recombinant polypeptides, multimeric-protein-complexes, heteromultimeric-protein-complexes, multimeric-fusion-proteins, heteromultimeric-fusion-proteins, immunoglobulin-polypeptide-chains, immunoglobulins, redox-fusion-polypeptides, and/or thioredoxin-related proteins; in association with oil bodies.

Accordingly, provided herein are methods of producing a recombinant multimeric-protein-complex, said method comprising: (a) producing in a cell comprising oil bodies, a first recombinant polypeptide and a second recombinant polypeptide wherein said first recombinant polypeptide is capable of associating with said second recombinant polypeptide to form said multimeric-protein-complex; and (b) associating said multimeric-protein-complex with an oil body through an oil-body-targeting-protein capable of associating with said oil bodies and said first recombinant polypeptide.

The method further contemplates isolating the oil bodies associated with said recombinant multimeric-protein-complex. The second recombinant polypeptide can be associated with a second oil-body-targeting-protein capable of associating with an oil body and said second recombinant polypeptide. Each of said oil-body-targeting-proteins can be an oil-body-protein or an immunoglobulin. The oil-body-targeting-protein can be an oleosin or caleosin. When the oil-body-targeting-protein can be an oleosin or caleosin, the first recombinant polypeptide can be fused to said oleosin or caleosin. Likewise, the second recombinant polypeptide can be fused to a second oleosin or second caleosin capable of associating with an oil body. The oil-body-targeting protein can also comprise an immunoglobulin-binding-protein, such as protein A. The first and second recombinant polypeptides can be produced as a multimeric-fusion-protein comprising said first and second polypetide, and can form a multimeric-protein-complex. The multimeric-protein-complex can be a heteromultimeric-protein-complex, and the heteromultimeric-protein-complex can be an enzymatically active redox complex or an immunoglobulin. In one embodiment, the first recombinant polypeptide is capable of associating with said second recombinant polypeptide in the cell. In another embodiment, the first recombinant polypeptide can be a thioredoxin and the second recombinant polypeptide can be a thioredoxin-reductase. In another embodiment, the first and second recombinant polypeptides can be an immunoglobulin-polypeptide-chain. For example, the first recombinant polypeptide can be an immunoglobulin light chain, or an immunologically active portion thereof, and the second recombinant polypeptide can be an immunoglobulin heavy chain, or an immunologically active portion thereof. In this embodiment, the oil-body-targeting-protein can comprise protein A, protein L or protein G, preferably fused to an oil body protein such as an oleosin. The cell can be a plant cell, such as a safflower cell, and the like.

Also provided herein is a method of expressing a recombinant multimeric-protein-complex comprising a first and second recombinant polypeptide in a cell, said method comprising:

(a) introducing into a cell a first chimeric nucleic acid sequence comprising:
  (i) a first nucleic acid sequence capable of regulating transcription in said cell operatively linked to;
  (ii) a second nucleic acid sequence encoding a first recombinant polypeptide;
(b) introducing into said cell a second chimeric nucleic acid sequence comprising:
  (i) a third nucleic acid sequence capable of regulating transcription in said cell operatively linked to;
  (ii) a fourth nucleic acid sequence encoding a second recombinant polypeptide;
(c) growing said cell under conditions to permit expression of said first and second recombinant polypeptide in a progeny cell comprising oil bodies wherein said first recombinant polypeptide and said second recombinant polypeptide are capable of forming a multimeric-protein-complex; and
(d) associating said first recombinant polypeptide with an oil body through an oil-body-targeting-protein capable of associating with said oil bodies and said first recombinant polypeptide. This method further contemplates isolating from the progeny cell, oil bodies comprising the multimeric-protein-complex. The method also contemplates separating the multimeric-protein-complex from the oil bodies. The second recombinant polypeptide can be associated with a second oil-body-targeting-protein capable of associating with an oil body and second recombinant polypeptide. Each of said oil-body-targeting-proteins can be an oil-body-protein or an immunoglobulin. The oil-body-targeting-protein can be an oleosin or caleosin. When the oil-body-targeting-protein is an oleosin or caleosin, the first recombinant polypeptide can be fused to said oleosin or caleosin. Likewise, the second recombinant polypeptide can be fused to a second oleosin or second caleosin capable of associating with an oil body. The first and second recombinant polypeptides can be produced as a multimeric-fusion-protein comprising said first and second polypetide, and can form a multimeric-protein-complex. The multimeric-protein-complex can be a heteromultimeric-protein-complex, and the heteromultimeric-protein-complex can be an enzymatically active redox complex or an immunoglobulin. In one embodiment, the first recombinant polypeptide and said second recombinant polypeptide are capable of forming a multimeric-protein-complex in said progeny cell. In another embodiment, the first recombinant polypeptide can be a thioredoxin and the second recombinant polypeptide can be a thioredoxin-reductase. In another embodiment, the first and second recombinant polypeptides can be an immunoglobulin-polypeptide-chain. For example, the first recombinant polypeptide can be an immunoglobulin light chain, or an immunologically active portion thereof, and the second recombinant polypeptide can be an immunoglobulin heavy chain, or an immunologically active portion thereof. In this embodiment, the oil-body-targeting-protein can comprise protein A, protein L or protein G, preferably fused to an oil body protein such as an oleosin. The cell can be a plant cell, such as a safflower cell, and the like.

Also provided herein are methods of producing in a plant a recombinant multimeric-protein-complex, said method comprising:
(a) preparing a first plant comprising cells, said cells comprising oil bodies and a first recombinant polypeptide wherein said first recombinant polypeptide is capable of associating with said oil bodies through an oil-body-targeting-protein;
(b) preparing a second plant comprising cells, said cells comprising oil bodies and a second recombinant polypeptide; and
(c) sexually crossing said first plant with said second plant to produce a progeny plant comprising cells, said cells comprising oil bodies, wherein said oil bodies are capable of associating with said first recombinant polypeptide, and said first recombinant recombinant polypeptide is capable of associating with said second recombinant polypeptide to form said recombinant multimeric-protein-complex. The second recombinant polypeptide can be associated with oil bodies through a second oil-body-targeting-protein in the second plant. The oil bodies can be isolated from the progeny plant comprising said multimeric-protein-complex. The oil-body-targeting-protein can be selected from an oil-body-protein or an immunoglobulin, wherein the oil-body-protein can be an oleosin or caleosin. The first recombinant polypeptide can be fused to the oleosin or caleosin; and the second recombinant polypeptide can be fused to a second oleosin or second caleosin capable of associating with an oil body. The first and second recombinant polypeptide can form a multimeric-protein-complex, such as a heteromultimeric-protein-complex, wherein the heteromultimeric-protein-complex can be an enzymatically active redox complex or an immunoglobulin. In another embodiment, the first and second recombinant polypeptides can be an immunoglobulin-polypeptide-chain. For example, the first recombinant polypeptide can be an immunoglobulin light chain, or an immunologically active portion thereof, and the second recombinant polypeptide can be an immunoglobulin heavy chain, or an immunologically active portion thereof. In this embodiment, the oil-body-targeting-protein can comprise protein A, protein L or protein G, preferably fused to an oil body protein such as an oleosin. The plant can be a safflower plant.

Also provided herein are methods of producing in a plant a recombinant multimeric-protein-complex, said method comprising:
(a) preparing a first plant comprising cells, said cells comprising oil bodies and a first and second recombinant polypeptide wherein said first recombinant polypeptide is capable of associating with said oil bodies through an oil-body-targeting-protein;
(b) preparing a second plant comprising cells, said cells comprising oil bodies and an oil-body-targeting-protein that is capable of associating with said first recombinant polypeptide; and
(c) sexually crossing said first plant with said second plant to produce a progeny plant comprising cells, said cells comprising oil bodies, wherein said oil bodies are capable of associating with said first recombinant polypeptide through said oil-body-targeting-protein, and said first recombinant recombinant polypeptide is capable of associating with said second recombinant polypeptide to form said recombinant multimeric-protein-complex. The oil bodies can be isolated from the progeny plant comprising said multimeric-protein-complex. The multimeric-protein-complex can be separated from the oil bodies. The oil-body-targeting-protein can be selected from an oil-body-protein or an immunoglobulin, wherein the oil-body-protein can be an oleosin or caleosin. The first and second recombinant polypeptide can form a multimeric-protein-complex, such as a heteromultimeric-protein-complex, wherein the heteromultimeric-protein-complex can be an enzymatically active redox complex or an immunoglobulin. In a particular embodiment, the first recombinant polypeptide is a thioredoxin and the second recombinant polypeptide is a thioredoxin-reductase. In another embodiment, the first and second recombinant polypeptides can be an immunoglobulin-polypeptide-chain. For example, the first recombinant polypeptide can be an immunoglobulin light chain, or an immunologically active portion thereof, and the second recombinant polypeptide can be an immunoglobulin heavy chain, or an immunologically active portion thereof. In this embodiment, the oil-body-targeting-protein can comprise protein A, protein L or protein G, preferably fused to an oil body protein such as an oleosin. The plant can be a safflower plant.

Also provided herein are chimeric nucleic acids encoding a multimeric-fusion-protein as described herein, said nucleic acid comprising:
(a) a first nucleic acid sequence encoding an oil-body-targeting-protein operatively linked in reading frame to;
(b) a second nucleic acid sequence encoding a first recombinant polypeptide; linked in reading frame to;
(c) a third nucleic acid sequence encoding a second recombinant polypeptide, wherein said first and second recombinant polypeptide are capable of forming a multimeric-protein-complex. The oil-body-targeting-protein can be selected from an oil-body-protein or an immunoglobulin. The oil-body-protein can be an oleosin or caleosin. The multimeric-protein-complex can be a heteromultimeric-protein-complex, and the first and second recombinant polypeptide can form an enzymatically active heteromultimeric redox complex or an immunoglobulin. In a particular embodiment, the first recombinant polypeptide is a thioredoxin and the second recombinant polypeptide is a thioredoxin-reductase. In another embodiment, the first and second recombinant polypeptides can be an immunoglobulin-polypeptide-chain. For example, the first recombinant polypeptide can be an immunoglobulin light chain, or an immunologically active portion thereof, and the second recombinant polypeptide can be an immunoglobulin heavy chain, or an immunologically active portion thereof. In yet another embodiment, positioned between the nucleic acid sequence encoding an oil-body-targeting-protein and the nucleic acid sequence encoding a first recombinant polypeptide can be a linker nucleic acid sequence encoding an oil-body-surface-avoiding linker amino acid sequence. The oil-body-surface-avoiding linker amino acid sequence can be substantially negatively charged, or have a molecular weight of at least 35 kd. Optionally, the gene fusion further comprises a linker nucleic acid sequence encoding an amino acid sequence that is specifically cleavable by an enzyme or a chemical, wherein the linker sequence is positioned between the oil-body-surface-avoiding linker amino acid sequence that is also a non-proteolytic linker and said sequence encoding the first recombinant polypeptide.

Also provided herein are recombinant multimeric-fusion-proteins comprising (i) an oil-body-targeting-protein, or fragment thereof, (ii) a first recombinant polypeptide and a (iii) second recombinant polypeptide, wherein said first and second recombinant polypeptides are capable of forming a multimeric-protein-complex. The oil-body-targeting-protein can be selected from an oil-body-protein or an immunoglobulin, and the oil-body-protein can be an oleosin or a caleosin. The multimeric-fusion-protein can be a heteromultimeric-fusion-protein, wherein said first and second recombinant polypeptide form an enzymatically active heteromultimeric redox complex or an immunoglobulin. In a particular embodiment, the first recombinant polypeptide is a thioredoxin and the second recombinant polypeptide is a thioredoxin-reductase. In another embodiment, the first and second recombinant polypeptides can be an immunoglobulin-polypeptide-chain. For example, the first recombinant polypeptide can be an immunoglobulin light chain, or an immunologically active portion thereof, and the second recombinant polypeptide can be an immunoglobulin heavy chain, or an immunologically active portion thereof. In this embodiment, the oil-body-targeting-protein can comprise protein A, protein L or protein G, preferably fused to an oil body protein such as an oleosin. In yet another embodiment, positioned between the nucleic acid sequence encoding an oil-body-targeting-protein and the nucleic acid sequence encoding a first recombinant polypeptide can be a linker nucleic acid sequence encoding an oil-body-surface-avoiding linker amino acid sequence. The oil-body-surface-avoiding linker amino acid sequence can be substantially negatively charged, or have a molecular weight of at least 35 kd. Optionally, the gene fusion further comprises a linker nucleic acid sequence encoding an amino acid sequence that is specifically cleavable by an enzyme or a chemical, wherein the linker sequence is positioned between the oil-body-surface-avoiding linker amino acid sequence and said sequence encoding the first recombinant polypeptide.

Also provided herein are isolated oil bodies comprising a multimeric-protein-complex comprising (i) an oil-body-targeting-protein and (ii) a first recombinant polypeptide, said oil bodies further comprising a second recombinant polypeptide, wherein said first and second recombinant polypeptide are capable of forming a multimeric-protein-complex. The oil-body-targeting-protein can be selected from an oil-body-protein or an immunoglobulin, and the oil-body-protein can be an oleosin or a caleosin. The multimeric-fusion-protein can be a heteromultimeric-fusion-protein, wherein said first and second recombinant polypeptide form an enzymatically active heteromultimeric redox complex or an immunoglobulin. In a particular embodiment, the first recombinant polypeptide is a thioredoxin and the second recombinant polypeptide is a thioredoxin-reductase. In another embodiment, the first and second recombinant polypeptides can be an immunoglobulin-polypeptide-chain. For example, the first recombinant polypeptide can be an immunoglobulin light chain, or an immunologically active portion thereof, and the second recombinant polypeptide can be an immunoglobulin heavy chain, or an immunologically active portion thereof. In this embodiment, the oil-body-targeting-protein can comprise protein A, protein L or protein G, preferably fused to an oil body protein such as an oleosin.

Also provided herein are isolated oil bodies comprising:
(a) a first fusion protein comprising a first oil-body-targeting-protein fused to a first recombinant polypeptide; and
(b) a second fusion protein comprising a second oil-body-targeting-protein fused to a second recombinant polypeptide,
wherein said first and second recombinant polypeptide are capable of forming a multimeric-protein-complex. The oil-body-targeting-protein can be selected from an oil-body-protein or an immunoglobulin, and the oil-body-protein can be an oleosin or a caleosin. The multimeric-fusion-protein can be a heteromultimeric-fusion-protein, wherein said first and second recombinant polypeptide form an enzymatically active heteromultimeric redox complex or an immunoglobulin. In a particular embodiment, the first recombinant polypeptide is a thioredoxin and the second recombinant polypeptide is a thioredoxin-reductase. In another embodiment, the first and second recombinant polypeptides can be an immunoglobulin-polypeptide-chain. For example, the first recombinant polypeptide can be an immunoglobulin light chain, or an immunologically active portion thereof, and the second recombinant polypeptide can be an immunoglobulin heavy chain, or an immunologically active portion thereof. In this embodiment, the oil-body-targeting-protein can comprise protein A, protein L or protein G.

Also provided are cells and transgenic plants comprising oil bodies, multimeric-protein-complexes, and multimeric-fusion-proteins, set forth herein. In one embodiment, the first recombinant polypeptide can be an immunoglobulin-polypeptide-chain. For example, the first recombinant polypeptide can be an immunoglobulin light chain, or an immunologically active portion thereof, and the second recombinant polypeptide can be an immunoglobulin heavy chain, or an immunologically active portion thereof. In this embodiment, the oil-body-targeting-protein can comprise protein A, protein L or protein C. In embodiments, wherein said first recombinant polypeptide is a thioredoxin and said second recombinant polypeptide is a thioredoxin-reductase, the methods described herein can be used to formulate the oil bodies for use in the preparation of a food product, personal care product or pharmaceutical composition. These formulations can further comprise the addition of NADP or NADPH. The food product can be a milk or wheat based food product. The personal care product can reduce the oxidative stress to the surface area of the human body or can be used to lighten the skin. The pharmaceutical composition can be used to treat chronic obstructive pulmonary disease (COPD), cataracts, diabetes, envenomation, bronchiopulmonary disease, malignancies, psoriasis, reperfusion injury, wound healing, sepsis, GI bleeding, intestinal bowel disease (IBD), ulcers, GERD (gastro esophageal reflux disease).

Also provided herein are compositions comprising isolated oil bodies and a first recombinant polypeptide that can be an immunoglobulin-polypeptide-chain and a second recombinant polypeptide that can also be an immunoglobulin-polypeptide-chain. For example, the first recombinant polypeptide can be an immunoglobulin light chain, or an immunologically active portion thereof, and the second recombinant polypeptide can be an immunoglobulin heavy chain, or an immunologically active portion thereof. In this embodiment, the oil-body-targeting-protein can comprise protein A, protein L or protein G.

Also provided are multimeric-fusion-proteins, wherein the fusion-protein contains two or more polypeptide chains selected from the group of proteins set forth in FIG. 1. Methods are also provided of reducing allergenicity of a food comprising the steps of providing the isolated oil bodies set forth herein; and adding the isolated oil bodies to the food, whereby allergenicity of the food is reduced. The food can be selected from the group consisting of wheat flour, wheat dough, milk, cheese, yogurt and ice cream. The various methods of treating food can further comprise providing NADH as a co-factor in the substantial absence of NADPH.

Also provided herein are methods of treating or protecting a target against oxidative stress, comprising the steps of providing the recombinant redox fusion polypeptide comprising thioredoxin and thioredoxin-reductase; and contacting the recombinant fusion polypeptide with a target, wherein the target is susceptible to oxidative stress, thereby treating or protecting against the stress. The target can be selected from the group consisting of a molecule, a molecular complex, a cell, a tissue, and an organ.

Also provided herein are methods for preparing an enzymatically active redox protein associated with oil bodies comprising:
 a) producing in a cell a redox fusion polypeptide comprising a first redox protein linked to a second redox protein;
 b) associating said redox fusion polypeptide with oil bodies through an oil-body-targeting-protein capable of associating with said redox fusion polypeptide and said oil bodies; and
 c) isolating said oil bodies associated with said redox fusion polypeptide.

The first redox protein can be a thioredoxin and the second redox protein can be a thioredoxin-reductase.

Also, provided herein are methods of producing an immunoglobulin, said method comprising: (a) producing in a cell comprising oil bodies, a first immunoglobulin-polypeptide-chain and a second immunoglobulin-polypeptide-chain wherein said first immunoglobulin-polypeptide-chain is capable of associating with said second immunoglobulin-polypeptide-chain to form said immunoglobulin; and (b) associating said immunoglobulin with an oil body through an oil-body-targeting-protein capable of associating with said oil bodies and said first immunoglobulin-polypeptide-chain. For example, the first immunoglobulin-polypeptide-chain can be an immunoglobulin light chain, or an immunologically active portion thereof, and the second immunoglobulin-polypeptide-chain can be an immunoglobulin heavy chain, or an immunologically active portion thereof. In this embodiment, the oil-body-targeting-protein can comprise protein A, protein L or protein G, preferably fused to an oil body protein such as an oleosin.

Also provided herein are methods for preparing a redox protein or an immunoglobulin associated with oil bodies comprising:
 a) introducing into a cell a chimeric nucleic acid sequence comprising:
  1) a first nucleic acid sequence capable of regulating transcription in said cell operatively linked to;
  2) a second nucleic acid sequence encoding a recombinant fusion polypeptide comprising (i) a nucleic acid sequence encoding a sufficient portion of an oil-body-protein to provide targeting of said recombinant fusion polypeptide to an oil body linked to (ii) a nucleic acid sequence encoding a redox fusion polypeptide comprising a first redox protein linked to a second redox protein, or a nucleic acid sequence encoding a immunoglobulin comprising a first immunoglobulin-polypeptide-chain linked to a second immunoglobulin-polypeptide-chain, operatively linked to;
  3) a third nucleic acid sequence capable of terminating transcription in said cell;
 b) growing said cell under conditions to permit expression of said redox fusion polypeptide or immunoglobulin in a progeny cell comprising oil bodies; and
 c) isolating from said progeny cell said oil bodies comprising said redox fusion polypeptide or immunoglobulin.

In certain embodiments, positioned between said nucleic acid sequence encoding a sufficient portion of an oil-body-protein and said nucleic acid sequence encoding a redox fusion polypeptide or immunoglobulin can be a linker nucleic acid sequence encoding an oil-body-surface-avoiding linker amino acid sequence. The oil-body-surface-avoiding linker amino acid sequence can be substantially negatively charged or have a molecular weight of at least 35 kd. Optionally, the gene fusion further comprises a linker nucleic acid sequence encoding an amino acid sequence that is specifically cleavable by an enzyme or a chemical, wherein the linker sequence is positioned between the oil-body-surface-avoiding linker amino acid sequence and said nucleic acid sequence encoding a redox fusion polypeptide. In this optional embodiment, also contemplated is the introduction of an enzyme or chemical that cleaves said redox fusion polypeptide from said oil body, thereby obtaining isolated redox fusion polypeptide. The first redox protein can be a thioredoxin and said second redox protein can be a thioredoxin-reductase. In one embodiment, the thioredoxin and thioredoxin-reductase can be obtained from *Arabidopsis*. In another embodiment, the first redox protein is at least 5 times more active when produced as a redox fusion polypeptide as compared to the production of the first redox protein without the second redox protein.

Also provided herein, for use with the various methods set forth herein is the formulation of an emulsion of the oil bodies associated with the redox fusion polypeptide for use in the preparation of a product capable of treating oxidative stress in a target, a product capable of chemically reducing a target, pharmaceutical composition, a personal care product or a food product. Accordingly, an emulsion formulation composition is provided.

Also provided herein is a chimeric nucleic acid comprising:

1) a first nucleic acid sequence capable of regulating transcription in a host cell operatively linked to;

2) a second nucleic acid sequence encoding a recombinant fusion polypeptide comprising (i) a nucleic acid sequence encoding a sufficient portion of an oil-body-protein to provide targeting of said recombinant fusion polypeptide to an oil body linked to (ii) a nucleic acid sequence encoding a redox fusion polypeptide comprising a first redox protein linked to a second redox protein operatively linked to;

3) a third nucleic acid sequence capable of terminating transcription in said cell.

The oil-body-protein can be an oleosin or a caleosin. The first redox protein can be a thioredoxin and said second redox protein can be a thioredoxin-reductase. In certain embodiments, positioned between said nucleic acid sequence encoding a sufficient portion of an oil-body-protein and said nucleic acid sequence encoding a redox fusion polypeptide is a linker nucleic acid sequence encoding an oil-body-surface-avoiding linker amino acid sequence. The oil-body-surface-avoiding linker amino acid sequence can be substantially negatively charged, or have a molecular weight of at least 35 kd. In one embodiment, the gene fusion optionally further comprises a linker nucleic acid sequence encoding an amino acid sequence that is specifically cleavable by an enzyme or a chemical, wherein the linker sequence is positioned between the oil-body-surface-avoiding linker amino acid sequence and said nucleic acid sequence encoding a redox fusion polypeptide.

Also provided herein are transgenic plants, e.g., safflower plants, comprising any of the chimeric nucleic acid sequences and constructs described herein. The chimeric nucleic acids can be contained within a plastid. Accordingly, isolated plastids are provided having chimeric nucleic acids therein. Also provided are plant seeds comprising the chimeric nucleic acids provided herein.

Also provided are oil body preparations obtained using any of the methods provided herein, and food products, pharmaceutical compositions, and personal care products containing the oil body preparations. The products and/or compositions provided herein are capable of treating oxidative stress in a target, capable of chemically reducing a target. Also provided is a detergent composition comprising an oil body preparation capable of chemically reducing a target, and related methods of cleansing an item, comprising administering such product to the item under conditions that promote cleansing.

Also provided herein are nucleic acid constructs comprising a gene fusion, wherein the gene fusion comprises a first region encoding an oil-body-protein or an active fragment thereof, operably linked to a second region encoding at least one thioredoxin-related protein or an active fragment thereof. In one embodiment, the at least one thioredoxin-related protein can be thioredoxin. The thioredoxin can be obtained from *Arabidopsis* or wheat.

In another embodiment, the at least one thioredoxin-related protein can be thioredoxin-reductase. The thioredoxin-reductase can be derived from *Arabidopsis* or wheat. The thioredoxin-reductase can be an NADPH-dependent thioredoxin-reductase. The second region can encode a thioredoxin and thioredoxin-reductase. In one embodiment, the thioredoxin and thioredoxin-reductase is obtained from *Mycobacterium leprae*. In another embodiment, the at least one thioredoxin-related protein can be an engineered fusion protein. The first region can precede, in a 5' to 3' direction, the second region. Alternatively, the first region follows, in a 5' to 3' direction, the second region. The gene fusion can optionally further comprise a third region encoding a second thioredoxin-related protein or an active fragment thereof, operably linked to the first region, or to the second region, or to both. A seed-specific promoter, such as a phaseolin promoter or linin promoter, can be operably linked to the gene fusion. In one embodiment, at least one thioredoxin-related protein is derived from a plant species selected from the group consisting of *Arabidopsis* and wheat. In another embodiment, at least one thioredoxin-related protein can be derived from *E. coli*.

In one embodiment, the gene fusion further comprises a nucleic acid sequence encoding an oil-body-surface-avoiding linker amino acid sequence, wherein the linker amino acid sequence is positioned between the first region and the second region. The oil-body-surface-avoiding linker amino acid sequence can be substantially negatively charged, or have a molecular weight of at least 35 kd. In addition, the gene fusion can further comprise a linker nucleic acid sequence encoding an amino acid sequence that is specifically cleavable by an enzyme or a chemical, wherein the linker sequence is positioned between the oil-body-surface-avoiding linker amino acid sequence and the second region.

Also provided herein are transgenic plants containing a nucleic acid construct comprising a gene fusion, wherein the gene fusion comprises a region encoding an oil-body-protein or an active fragment thereof, operably linked to a region encoding a first thioredoxin-related protein or an active fragment thereof. The thioredoxin-related protein can be thioredoxin. The nucleic acid construct can be contained within a plastid. In one embodiment, when the first thioredoxin-related protein is thioredoxin and the construct can further comprise a region encoding a thioredoxin-reductase. The gene fusion can optionally further comprise a third region encoding a second thioredoxin-related protein or an active fragment thereof, operably linked to the first region, or to the second region, or to both. The gene fusion can optionally further comprise a nucleic acid sequence encoding an oil-body-surface-avoiding linker amino acid sequence, wherein the nucleic acid encoding the linker amino acid sequence is positioned between the region encoding an oil-body-protein and the region encoding a first thioredoxin-related protein. The oil-body-surface-avoiding linker amino acid sequence can be substantially negatively charged, or have a molecular weight of at least 35 kd. The gene fusion can optionally further comprise a linker nucleic acid sequence encoding an amino acid sequence that is specifically cleavable by an enzyme or a chemical, wherein the linker sequence is positioned between the oil-body-surface-avoiding linker amino acid sequence and the region encoding a first thioredoxin-related protein.

Also provided is a transgenic plant comprising a nucleic acid construct, a seed-specific promoter operably linked to a gene fusion, wherein the gene fusion comprises a region encoding an oil-body-protein or an active fragment thereof, operably linked to a region encoding a first thioredoxin-related protein or an active fragment thereof, wherein a fusion protein comprising activities of oleosin and the thioredoxin-related protein is produced in a seed of the plant. In another embodiment, a thioredoxin-related protein having concentration of at least about 0.5% of total cellular seed protein is provided. Also provided herein is an extract comprising an activity of a thioredoxin-related protein. Also provided are oil bodies and/or oil obtained from various seeds.

Also provided herein are methods of making a fusion protein comprising a thioredoxin-related activity, the method comprising the steps of:

a) providing a transgenic plant comprising a nucleic acid construct comprising a seed-specific promoter operably linked to a gene fusion, wherein the gene fusion comprises a region encoding an oil-body-protein or an active fragment thereof, operably linked to a region encoding a first thioredoxin-related protein or an active fragment thereof, the gene fusion encoding a fusion protein comprising a thioredoxin-related activity;

b) obtaining seeds from the plant; and c) recovering the fusion protein by isolating oil bodies from the seeds. In one embodiment, the oil bodies are fractionated to achieve partial purification of the fusion protein. The oil bodies can be in association with a fusion protein. The oil-body-protein can be cleaved from the thioredoxin-related protein after fractionation of the oil bodies. The cleaving step can make use of a protease or chemical proteolysis.

Also provided herein are methods of reducing allergenicity of a food comprising the steps of:

a) providing a preparation comprising oil bodies associated with a fusion protein, the fusion protein comprising an oil-body-protein or an active fragment thereof and a thioredoxin-related protein or an active fragment thereof; and b) adding the preparation to the food, whereby allergenicity of the food is reduced due to activity of the thioredoxin-related protein or fragment. The food can be wheat flour, wheat dough, milk, cheese, yogurt and ice cream. In one embodiment, NADH is used as a co-factor in the substantial absence of NADPH.

Also provided herein are pharmaceutical compositions comprising a fusion protein, the fusion protein comprising an oil-body-protein or an active fragment thereof and a thioredoxin-related protein or an active fragment thereof, in a pharmaceutically acceptable carrier. The oil bodies can be associated with the fusion protein. Also provided is a cosmetic formulation comprising oil bodies associated with a fusion protein, the fusion protein comprising an oil-body-protein or an active fragment thereof and a thioredoxin-related protein or an active fragment thereof, in a pharmaceutically acceptable carrier. Also provided are methods of treating or protecting a target against oxidative stress, comprising the steps of:

a) providing a preparation comprising a fusion protein, the fusion protein comprising an oil-body-protein or an active fragment thereof and a thioredoxin-related protein or an active fragment thereof; and b) contacting the preparation with a target, wherein the target is susceptible to oxidative stress, thereby treating or protecting against the stress. The target can be selected from the group consisting of a molecule, a molecular complex, a cell, a tissue, and an organ.

Also provided is a nucleic acid construct comprising a gene fusion, wherein the gene fusion comprises a first region encoding an oil-body-protein or an active fragment thereof, operably linked to a second region encoding at least one polypeptide or an active fragment thereof, and an oil-body-surface-avoiding linker in frame between the first and second region polypeptides. Also provided are methods of expressing this construct into the encoded amino acid sequence; and oil bodies, formulations, emulsions, cells, and plants comprising the construct and encoded amino acid sequence. These particular constructs, oil bodies, formulations, emulsions, cells, and plants can be produced according to the methods described herein. The second region can encode any polypeptide, for example, a therapeutically, nutritionally, industrially or cosmetically useful peptide as set forth herein. For example, the second region can encode a redox protein, an immunoglobulin, a thioredoxin-related protein or any one or more recombinant polypeptides of a multimeric-protein-complex.

Other features and advantages of the present invention will become readily apparent from the following detailed description. It should be understood however that the detailed description and the specific examples while indicating particular embodiments of the invention are given by way of illustration only.

BRIEF DESCRIPTION OF THE DRAWINGS

FIG. 1 provides a listing of exemplary proteins for use in the heteromultimeric-fusion-proteins and heteromultimeric-protein-complexes provided herein.

FIG. 3. A) Coomassie stained gel of *Arabidopsis* total protein extracts showing reduced or non-reduced samples from wild type (wt) seeds and transgenic SBS4809 seeds expressing chimeric heavy and light antibody chains (Lines #6 and #13). Mouse (Mm) and human (Hu) samples of IgG1 antibody are included as controls. B) Western blots showing human heavy chain IgG Fc-specifc detection and human kappa chain-specific detection. Reduced samples were separated on SDS-PAGE to identify individual antibody chains, while non-reduced samples were separated to identify antibody assemblies of heavy and light chains covalently bound by disulfide bonds. Both heavy and light chains are detected in the assembled antibody complex (non-reduced samples; arrow). The migration of this complex is comparable to the mouse and human IgG1 control protein.

FIG. 4 (and SEQ ID NO:38) shows the amino acid sequence of the five immunoglobulin-binding domains in the Protein A sequence of *Staphylococcus aureus*.

FIG. 5 (and SEQ ID NO:39) shows the DNA and encoding amino acid sequence of the Protein A insert in pSBS2904.

DETAILED DESCRIPTION OF THE INVENTION

Figure 2:
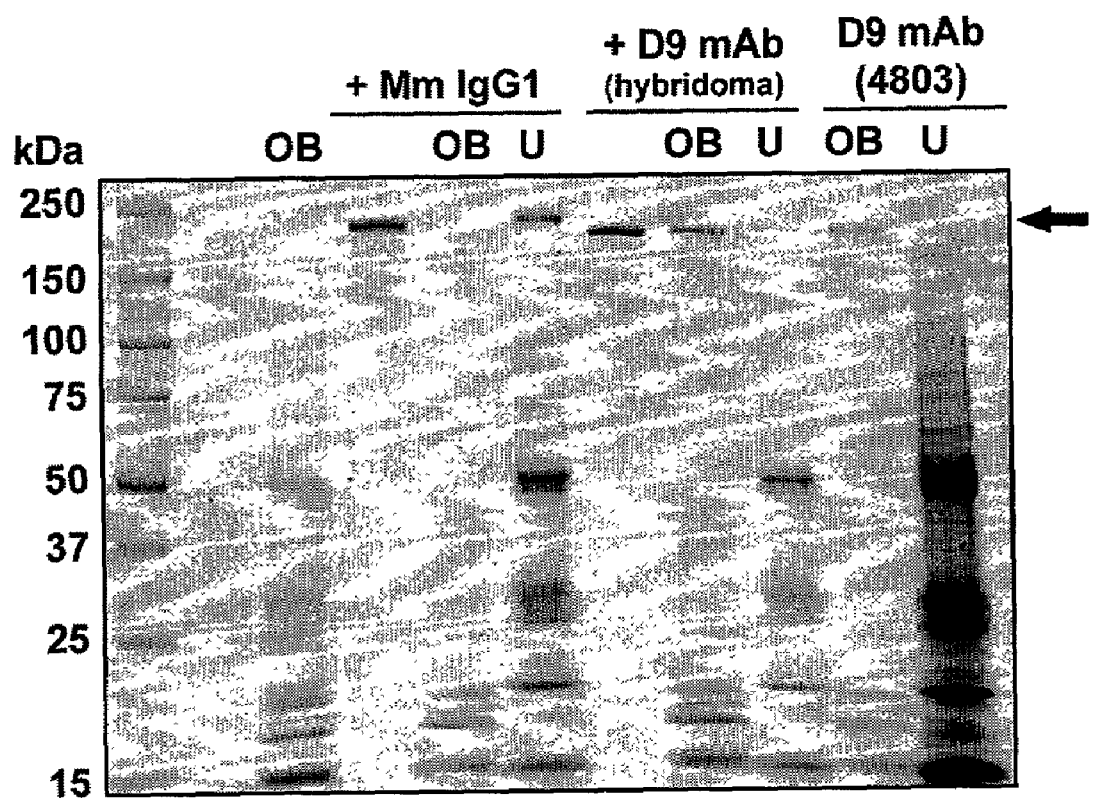
FIG. 2 Coomassie stained protein gel showing the partitioning of assembled antibody complexes with the oil body (OB) or the soluble undematant (U) fraction from wild type (wt) *Arabidopsis* C24 or transgenic SBS4803 seeds. The arrow indicates the high molecular weight antibody complexes in non-reduced samples separated by SDS-PAGE as evident by the mouse IgG1 and purified D9 MAb control lanes.

As hereinbefore mentioned, the present invention relates to novel and improved methods for the production of multimeric proteins, including a first and second recombinant polypeptide, multimeric-protein-complexes, heteromultimeric-protein-complexes, multimeric-fusion-proteins, heteromultimeric-fusion-proteins, immunoglobulin-polypeptide-chains, immunoglobulins, redox-fusion-polypeptides, and a first and second thioredoxin-related protein; and related products. These methods permit the production of active multimeric-protein-complexes in association with oil bodies. The oil bodies in association with the multimeric-protein-complex may be used to prepare various useful emulsions.

Accordingly, provided herein are methods of producing a recombinant multimeric-protein-complex associated with an oil body, said method comprising:

(a) producing in a cell comprising oil bodies, a first recombinant polypeptide and a second recombinant polypeptide wherein said first recombinant polypeptide is capable of associating with said second recombinant polypeptide in the cell to form said multimeric-protein-complex; and (b) associating said multimeric-protein-complex with an oil body through an oil-body-targeting-protein capable of associating with said oil body and said first recombinant polypeptide.

Definitions and Terms

Unless defined otherwise, all technical and scientific terms used herein have the same meaning as is commonly understood by one of skill in the art to which this invention belongs. Where permitted, all patents, applications, published applications and other publications and sequences from GenBank, SwissPro and other data bases referred to throughout in the disclosure herein are incorporated by reference in their entirety.

As used herein, the phrase "multimeric-protein-complex", refers to two or more polypeptide chains that permanently or repeatedly interact or permanently or repeatedly coordinate to form a biologically active assembly comprising said two or more polypeptide chains. It should be noted that the polypeptides may be independently biologically active without interaction or coordination to form the complex. The multimeric-protein-complex may provide a biological structure, or it may be capable of facilitating a chemical or biological reaction. For example, one of the protein regions within the multimeric-protein-complex can repeatedly activate or repeatedly inactivate the biological or metabolic activity of one or more of the other proteins contained within the multimeric-protein-complex. In one embodiment, the first and second recombinant polypeptide contained in a multimeric-protein-complex may either associate or interact as independent non-contiguous polypeptide chains or the multimeric-protein-complex may be prepared as a fusion polypeptide (multimeric-fusion-protein) between the first and second recombinant polypeptide.

One example of a repeated (e.g., reoccurring) interaction or association between the two or more polypeptides of a multimeric-protein-complex provided herein is the interaction between two or more non-identical redox proteins to form a heteromultimeric-protein-complex. Exemplary redox proteins for use in this regard are thioredoxin and the thioredoxin-reductase. A further example is the interaction between two or more immunoglobulin-polypeptide-chains to form an immunoglobulin. As used herein, the phrase "heteromultimeric-protein-complex", refers to two or more non-identical polypeptide chains that permanently or repeatedly interact or permanently or repeatedly coordinate to form a biologically active assembly comprising said two or more polypeptide chains. Other examples of multimeric-protein-complexes provided herein include a first and second recombinant polypeptide, heteromultimeric-protein-complexes, multimeric-fusion-proteins, heteromultimeric-fusion-proteins, immunoglobulins, first and second immunoglobulin-polypeptide-chains, redox-fusion-polypeptides, and a first and second thioredoxin-related protein.

The recombinant polypeptide or multimeric-protein-complex is associated with an oil body. As used herein, the phrase "oil body" or "oil bodies" refers to any oil or fat storage organelle in any cell type. Accordingly, the oil bodies may be obtained from any cell comprising oil bodies, including plant cells (described in for example: Huang (1992) Ann. Rev. Plant Mol. Biol. 43: 177–200), animal cells (described in for example: Murphy (1990) Prog Lipid Res 29(4): 299–324), including adipocytes, hepatocytes, steroidogenic cells, mammary epithelial cells, macrophages, algae cells (described in for example: Rossler (1988) J. Physiol. London, 24: 394–400) fungal cells, including yeast cells (described in for example Leber et al. (1994) Yeast 10: 1421–1428) and bacterial cells (described in for example: Pieper-Furst et al. (1994) J. Bacteriol. 176: 4328–4337). Preferably the oil bodies used herein are oil bodies obtainable from plant cells and more preferably the oil bodies obtainable from plant seed cells.

As used herein, the phrase "is capable of associating with", "associate" or grammatical variations thereof, refers to any interaction between two or more polypeptides, including any covalent interactions (e.g. multimeric-fusion-proteins) as well as non-covalent interactions. Exemplary non-covalent interactions can be between the oil-body-targeting-protein and a redox protein or immunoglobulin-polypeptide-chain, as well as between two or more different proteins contained within two or more separate oil-body-protein fusion proteins (e.g., the redox proteins in oleosin-thioredoxin and oleosin-thioredoxin-reductase).

As used herein, the term "recombinant" (also referred to as heterologous) in the context of recombinant proteins and amino acids, means "of different natural origin" or represents a non-natural state. For example, if a host cell is transformed with a nucleotide sequence derived from another organism, particularly from another species, that nucleotide sequence and amino acid sequence encoded thereby, is recombinant (heterologous) with respect to that host cell and also with respect to descendants of the host cell which carry that gene. Similarly, recombinant (or heterologous) refers to a nucleotide sequence derived from and inserted into the same natural, original cell type, but which is present in a non-natural state, e.g., a different copy number, or under the control of different regulatory elements. A transforming nucleotide sequence may include a recombinant coding sequence, or recombinant regulatory elements. Alternatively, the transforming nucleotide sequence may be completely heterologous or may include any possible combination of heterologous and endogenous nucleic acid sequences.

In various embodiments of the present invention, the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, and/or thioredoxin-related proteins, are produced in a cell comprising oil bodies. As used herein the phrase "in a cell", "in the cell", or grammatical variations thereof, mean that the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, and/or thioredoxin-related proteins, may be produced in any cellular compartment of that cell, so long as that cell comprises oil bodies therein. In embodiments of the invention in which plant cells are used, the phrase is intended to include the plant apoplast.

In various embodiments provided herein, the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, and thioredoxin-related proteins, associate with an oil body through an oil-body-targeting-protein. As used herein, the phrase "oil-body-targeting-protein" refers to any protein, protein fragment or peptide capable of associating with an oil body. Exemplary oil-body-targeting-proteins for use herein include oil-body-proteins, such as oleosin and caleosin; immunoglobulins, such as bi-specific antibodies; and the like.

In embodiments described herein in which an oil-body-protein is used, the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, and thioredoxin-related proteins, are preferably fused to the oil-body-protein. The term "oil-body-protein" refers to any protein naturally present in cells and having the capability of association with oil bodies, including any oleosin or caleosin.

Accordingly, provided herein a method of expressing a recombinant multimeric-protein-complex comprising a first and second recombinant polypeptide in a cell, said method comprising:
(a) introducing into a cell a first chimeric nucleic acid sequence comprising:
   (i) a first nucleic acid sequence capable of regulating transcription in said cell operatively linked to;
   (ii) a second nucleic acid sequence encoding a first recombinant polypeptide, such as a redox protein, an immunoglobulin-polypeptide-chain or an thioredoxin-related protein, fused to an oil-body-protein;
(b) introducing into said cell a second chimeric nucleic acid sequence comprising:
   (i) a third nucleic acid sequence capable of regulating transcription in said cell operatively linked to;
   (ii) a fourth nucleic acid sequence encoding a second recombinant polypeptide, such as a second redox protein, a second immunoglobulin-polypeptide-chain or a second thioredoxin-related protein;
(c) growing said cell under conditions to permit expression of said first and second recombinant polypeptide in a progeny cell comprising oil bodies wherein said first recombinant polypeptide and said second recombinant polypeptide are capable of forming a multimeric-protein-complex, preferably in said progeny cell; and
(d) associating said first recombinant polypeptide with an oil body through said oil-body-protein.

The term "nucleic acid" as used herein refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences may be ribonucleic acids (RNA) or deoxyribonucleic acids (DNA) and may contain naturally occurring bases including adenine, guanine, cytosine, thymidine and uracil. The sequences also may contain modified bases such as xanthine, hypoxanthine, 2-aminoadenine, 6-methyl, 2-propyl and other alkyl adenines, 5-halo-uracil, 5-halo cytosine, 6-aza uracil, 6-aza cytosine and 6-aza thymine, pseudo uracil, 4-thiouracil, 8-halo adenine, 8-amino adenine, 8-thiol-adenine, 8-thio-alkyl adenines, 8-hydroxyl adenine and other 8-substituted adenines, 8-halo guanines, 8 amino guanine, 8 thiol guanine, 8-thioalkyl guanines, 8 hydroxyl guanine and other 8-substituted guanines, other aza and deaza uracils, thymidines, cytosines, adenines, or guanines, 5-trifluoromethyl uracil and 5-trifluoro cytosine.

Multimeric-protein-complexes

In accordance with the methods and compositions provided herein, any two recombinant polypeptides capable of forming a multimeric-protein-complex may be used. The nucleic acid sequences encoding the two recombinant polypeptides may be obtained from any biological source or may be prepared synthetically. In general nucleic acid sequence encoding multimeric proteins are known to the art and readily available. Known nucleic acid sequences encoding multimeric-protein-complexes may be used to design and construct nucleic acid sequence based probes in order to uncover and identify previously undiscovered nucleic acid sequences encoding multimeric-protein-complexes, for example, by screening cDNA or genomic libraries or using 2- or multi-hybrid systems. Thus, additional nucleic acid sequences encoding multimeric-protein-complexes may be discovered and used as described herein.

The first and/or second recombinant polypeptides that are comprised within a multimeric-protein-complex provided herein, can themselves be in the form of heteromultimeric-protein-complexes, multimeric-fusion-proteins, heteromultimeric-fusion-proteins, immunoglobulins, immunoglobulin-polypeptide-chains, redox-fusion-polypeptides, and/or a first and/or second thioredoxin-related protein.

The nucleic acid sequence encoding the first and second recombinant polypeptide, heteromultimeric-protein-complexes, multimeric-fusion-proteins, heteromultimeric-fusion-proteins, immunoglobulins, immunoglobulin-polypeptide-chains, redox-fusion-polypeptides, and/or a first and/or second thioredoxin-related protein may be obtained from separate sources or may be obtained from the same source. In general however, such nucleic acid sequence is obtained from the same or a similar biological source. In certain embodiments wherein the nucleic acid sequence encoding the first and second recombinant polypeptide protein are obtained from the same source, the nucleic acid sequence encoding the first recombinant polypeptide and second recombinant polypeptide may be naturally fused. In accordance with a particular embodiment, the nucleic acid sequences encoding the first and second recombinant polypeptide are obtained from a plant source.

Oil-body-surface-avoiding Linkers

Polypeptide spacers or linkers of variable length and/or negative charge can be used herein to separate the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, and the first and/or second thioredoxin-related proteins from the in-frame oil-body-targeting-protein, to improve activity of and/or the accessibility of the polypeptide or complex. For example, in one embodiment set forth herein, positioned between a nucleic acid sequence encoding a sufficient portion of an oil-bodyprotein and a nucleic acid sequence encoding either the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, and the first and/or second thioredoxin-related proteins; is a linker nucleic acid sequence encoding an oil-body-surface-avoiding linker amino acid sequence.

Oil-body-surface-avoiding linkers are positioned between the oil-body targeting sequence and an in-frame recombinant polypeptide of interest, e.g., the multimeric-protein-complexes provided herein, serve to increase the distance and or decrease the interaction between the negatively charged oil body surface and the recombinant polypeptide of interest. A negatively charged linker is repelled by the negatively charged oil body surface, in turn increasing the distance or decreasing the interaction of its attached recombinant polypeptide with the oil body surface. As a consequence of the increased distance from the oil body surface, the recombinant polypeptide will be more accessible, e.g. to its target(s) substrate, protein substrate, protein partner, and less affected by the charged oil body surface. Exemplary linker sequences for use herein can be either a negatively charged linker, or a linker having a molecular weight of at least about 35 kd or more.

As used herein, a "negatively charged linker" sequence, refers to any amino acid segment, or nucleic acid encoding such, that has a pi less than or equal to the pI of an oil body. In certain embodiments, the pI of the negatively charged linker is about 90%, 80%, 70%, 60%, 50%, 40%, 30%, down to about 25% or more, below that of the pI of an oil body in the particular plant or cell system being used. Exemplary negatively charged linkers can be prepared comprising any combination of the negatively charged amino acid residues. For example, in one embodiment, a negatively charged linker comprises either a poly-glutamate or poly-aspartate sequence, or any combination of both amino acid residues. The negatively charged linker is typically at least 5, 10, 15, 20, 25, 30, 35, 40, 45, 50, 55, 60, 65, 70, 75, 80, 85, 90, 95, 100 or more amino acids in length. The negatively charged linkers are preferably non-proteolytic (e.g., non-proteolytic linkers), having no site for efficient proteolysis. When linker size rather than charge is used to minimize interaction of the recombinant polypeptide of interest with the oil body surface, then the linker is non-proteolytic and ranges in molecular weight from about 35 kd up to about 100 kd. The upper size limit is chosen such that the expression of, the activity of, the conformation of, and/or the access to target of, the recombinant polypeptide of interest is not significantly affected by the linker.

In certain embodiments, described herein where a non-proteolytic linker amino acid sequence is employed, the gene fusion or protein fusion (multimeric-fusion-protein) can optionally further comprise a linker nucleic or amino acid sequence encoding a sequence that is specifically cleavable by an enzyme or a chemical, wherein the linker sequence is positioned between the non-proteolytic linker sequence and sequence encoding the desired recombinant protein region, e.g., the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins set forth herein. When a cleavable linker sequence is used herein, in a particular embodiment, it is further downstream than the non-proteolytic linker sequence from the oil-body-targeting-protein region of the fusion protein. By virtue of cleavable linker, the recombinant fusion polypeptides provided herein, such as the multimeric-fusion-proteins and redox fusion polypeptides, can be isolated and purified by introducing an enzyme or chemical that cleaves said multimeric-fusion-protein and/or redox fusion polypeptide from said oil body, thereby obtaining and/or isolating the desired protein. It is contemplated herein that the use of cleavable linker sequence downstream of the non-proteolytic linker/spacer sequence will improve the yield of protein recovery when isolating or purifying proteins using the methods provided herein.

The nucleic acid sequences encoding the first or second recombinant polypeptide may be altered to improve expression levels for example, by optimizing the nucleic acids sequence in accordance with the preferred codon usage for the particular cell type which is selected for expression of the first and second recombinant polypeptide, or by altering of motifs known to destabilize mRNAs (see for example: PCT Patent Application 97/02352). Comparison of the codon usage of the first and second recombinant polypeptide with codon usage of the host will enable the identification of codons that may be changed. For example, typically plant evolution has tended towards a preference for CG rich nucleotide sequences while bacterial evolution has resulted in bias towards AT rich nucleotide sequences. By modifying the nucleic acid sequences to incorporate nucleic acid sequences preferred by the host cell, expression may be optimized. Construction of synthetic genes by altering codon usage is described in for example PCT patent Application 93/07278. The first and second recombinant polypeptide can be altered using for example targeted mutagenesis, random mutagenesis (Shiraishi et al. (1998) Arch. Biochem. Biophys. 358: 104–115; Galkin et al. (1997) Protein Eng. 10: 687–690; Carugo et al. (1997) Proteins 28: 10–28; Hurley et al. (1996) Biochemistry 35: 5670–5678), gene shuffling, and/or by the addition of organic solvent (Holmberg et al. (1999) Protein Eng. 12: 851–856). Any polypeptide spacers that are used in accordance with the methods and products provided herein may be altered in similar ways.

In particular embodiments provided herein, the recombinant polypeptides or thioredoxin-related proteins capable of forming a multimeric-protein-complex are capable of forming a heteromultimeric-protein-complex. Examples of heteromultimeric-protein-complexes that contain polypeptide chains that repeatedly interact, either to activate, inactivate, oxidize, reduce, stabilize, etc., with one another, that can be produced in association with oil bodies using the methods provided herein include those set forth in FIG. 1. Accordingly, exemplary proteins for use in the heteromultimeric-protein-complexes and nucleic acid constructs encoding such, provided herein include, among others described herein, those set forth in FIG. 1.

Other polypeptide regions that can be used in the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins, provided herein include, among other, those immunoglobulin regions set forth in Table 1.

TABLE 1

IMMUNOGLOBULIN HETERODIMERS

| Class or molecule | Subunits |
| --- | --- |
| Fab | Variable region and first constant region of heavy chain and complete light chain |
| Fv | Variable regions of heavy and light antibody chains |
| IgA | heavy chains, light chains and J (joining) chain |
| IgG, IgD, IgE | heavy and light chains |
| IgM | heavy chains, light chains and J (joining) chain |
| Antibody chain(s) and a toxin | Antibody chain(s) and a toxin |
| Autoantigens, allergens and transplant antigens with an adjuvant or tolerogen | Autoantigens, allergens and transplant antigens with an adjuvant or tolerogen |
| Chimeras using antibody Fc domain | Receptor subunits fused to the constant region of antibody heavy chains |

As set forth above, in one embodiment, exemplary heteromultimeric-protein-complexes and exemplary heteromultimeric-fusion-proteins provided herein comprise redox proteins, such as the thioredoxins and thioredoxin-reductases and immunoglobulins.

Oil-body-targeting-proteins

The nucleic acid sequence encoding the oil-body-targeting-protein that may be used in the methods and compositions provided herein may be any nucleic acid sequence encoding an oil-body-targeting-protein, protein fragment or peptide capable of association with first recombinant polypeptide, heteromultimeric-protein-complexes, multimeric-fusion-proteins, heteromultimeric-fusion-proteins, immunoglobulins, immunoglobulin-polypeptide-chains, redox-fusion-polypeptides, and/or a first and/or second thioredoxin-related protein and the oil bodies. The nucleic acid sequence encoding the oil body targeting peptide may be synthesized or obtained from any biological source.

For example, in one embodiment the oil-body-targeting-protein is an immunoglobulin or an immunoglobulin derived molecule, for example, a bispecific single chain antibody. The immunoglobulin will preferably bind an oil body protein that is associated with an oil body. The generation of single chain antibodies and bi-specific single chain antibodies is known to the art (see, e.g., U.S. Patents U.S. Pat. No. 5,763,733, U.S. Pat. No. 5,767,260 and U.S. Pat. No. 5,260,203). Nucleic acid sequences encoding single chain antibodies functioning as oil-body-targeting-proteins may be prepared from hybridoma cell lines expressing monoclonal antibodies raised against an oil body protein. In one embodiment the antibody binds an oleosin as described by Alting-Mees et al (2000) IBC's Annual International Conference on Antibody Engineering, Poster #1. In order to attain specificity for the first recombinant polypeptide a nucleic acid sequence encoding a second single chain antibody prepared from a monoclonal raised against the first recombinant polypeptide may be prepared and linked to the anti-oleosin single chain antibody. In this embodiment the oil body associates with the first recombinant polypeptide through non-covalent interactions of the oil-body-targeting-protein with the first recombinant polypeptide and the oil body. Alternatively the first recombinant polypeptide may be prepared as a fusion protein with an oil-body-targeting-protein. For example, a nucleic acid sequence encoding a single chain antibody raised against an oleosin may be fused to a nucleic acid sequence encoding the first recombinant polypeptide Non-immunoglobulin-based oil-body-targeting-proteins capable of association with the first recombinant polypeptide may be discovered and prepared using for example phage display techniques (Pharmacia Biotech Catalogue Number 27-9401-011 Recombinant Phage Antibody System Expression Kit).

Oil-body-targeting-proteins may also be chemically modified. For example, oleosins may be modified by changing chemical modification of the lysine residues using chemical agents such as biotinyl-N-hydroxysuccinimide ester resulting in a process referred to as biotinylation Conveniently this is accomplished by in vitro biotinylation of the oil bodies. In vivo biotinylation may be accomplished using the biotinylation domain peptide from the biotin carboxy carrier protein of E. coli acetyl-CoA carboxylase (Smith et al. (1998) Nucl. Acids. Res. 26: 1414–1420). Avidin or streptavidin may subsequently be used to accomplish association of the redox protein with the oil body.

In a particular embodiment the oil-body-targeting-protein is an oil-body-protein such as for example an oleosin or a caleosin or a sufficient portion derived thereof capable of targeting to an oil body. Nucleic acid sequences encoding oleosins are known to the art. These include for example the Arabidopsis oleosin (van Rooijen et al (1991) Plant Mol. Bio. 18:1177–1179); the maize oleosin (Qu and Huang (1990) J. Biol. Chem. Vol. 265 4:2238–2243); rapeseed oleosin (Lee and Huang (1991) Plant Physiol. 96:1395–1397); and the carrot oleosin (Hatzopoulos et al (1990) Plant Cell Vol. 2, 457–467.). Caleosin nucleic acid sequences are also known to the art (Naested et al (2000) Plant Mol Biol. 44(4):463–476; Chen et al (1999) Plant Cell Physiol. 40(10):1079–1086). Animal cell derived oil body proteins that may be used herein include adopihilin (Brasaemle et al, (1997) J. Lipid Res., 38: 2249–2263; Heid et al. (1998) Cell Tissue Research 294: 309–321), perilipin (Blanchette-Mackie et al. (1995), J. Lipid Res. 36: 1211–1226; Servetnick et al. (1995) J. Biol. Chem. 270: 16970–16973), apolipoproteins such as apo A–I, A–II, A–IV, C–I, C–II, CIII (Segrest et al. (1990), Proteins 8:103–117) and apoB (Chatterton et al. (1995) J. Lipid Res. 36: 2027–2037; Davis, R A in: Vance D E, Vance J. editors. Lipoprotein structure and secretion. The Netherlands, Elsevier, 191: 403–426.

In one embodiment, the first recombinant polypeptide is fused to an oil-body-protein. The methodology is further described in U.S. Pat. No. 5,650,554, which is incorporated herein by reference in its entirety. The first recombinant polypeptide may be fused to the N-terminus as well as to the C-terminus of the oil-body-protein (as described in: Moloney and van Rooijen (1996) INFORM 7:107–113) and fragments of the oil-body-protein such as for example the central domain of an oleosin molecule, or modified versions of the oil-body-protein may be used. In this embodiment, the second recombinant polypeptide is expressed intracellularly and then intracellularly associates with the first recombinant polypeptide to form the multimeric-protein-complex in the cell. Oil bodies comprising the multimeric-protein-complex are then conveniently isolated from the cells.

In a further embodiment both the first and second recombinant polypeptide are separately fused to an oil-body-protein. In this embodiment nucleic acid sequences encoding the first and second polypeptides may be prepared separately and introduced in separate cell lines or they may be introduced in the same cell lines. Where the nucleic acid sequences are introduced in the same cell line, these nucleic acid sequence may be prepared using two separate expression vectors, or they may be prepared using a single vector comprising nucleic acid sequences encoding both the first polypeptide fused to an oil body protein and the second polypeptide fused to an oil-body-protein. Where separate cell lines are used subsequent mating of the offspring (e.g. mating of plants) is used to prepare a generation of cells comprising oil bodies which comprise both the first and second recombinant polypeptide fused to an oil-body-protein In further alternate embodiment, the first and second recombinant polypeptide are fused to form a multimeric-fusion-protein comprising the multimeric-protein-complex. In such an embodiment, the first and second polypeptide is associated with the oil body through an oil-body-targeting-protein capable of associating with both the fusion protein and with the oil body. In a particular embodiment, the fusion protein comprising the multimeric-protein-complex is fused to an oil-body-protein, for example, an oleosin or caleosin.

In embodiments provided herein in which the multimeric-protein-complex is an immunoglobulin (e.g., a multimeric-immunoglobulin-complex), a particularly preferred oil body targeting protein is an oleosin or caleosin associated with an immunoglobulin binding protein, such as for example protein A (U.S. Pat. No. 5,151,350), protein L (U.S. Pat. No. 5,965,390) and protein G (U.S. Pat. No. 4,954,618), or active fragments of such immunoglobulin binding proteins. In a preferred embodiment, the immunoglobulin binding protein will be prepared as a fusion protein with an oil body protein.

New oil-body-proteins may be discovered for example by preparing oil bodies (described in further detail below) and identifying proteins in these preparations using for example SDS gel electrophoresis. Polyclonal antibodies may be raised against these proteins and used to screen cDNA libraries in order to identify nucleic acid sequences encoding oil-body-proteins. The methodologies are familiar to the skilled artisan (Huynh et al. (1985) in DNA Cloning Vol. 1. a Practical Approach ed. CM Glover, IRL Press, pp 49–78). New oil-body-proteins may further be discovered using known nucleic acid sequences encoding oil-body-proteins (e.g. the *Arabidopsis*, rapeseed, carrot and corn nucleic acid sequences) to probe for example cDNA and genomic libraries for the presence of nucleic acid sequences encoding oil-body-proteins.

Redox Proteins

In one embodiment, the first and second polypeptide are a first and second redox protein. Accordingly, one embodiment provided herein relates to novel and improved methods for the production of redox proteins. It has unexpectedly been found that a redox protein when prepared as a fusion protein with a second redox protein is fully enzymatically active when produced in association with an oil body. In contrast, when the redox protein is prepared without the second redox protein it has reduced enzymatic activity. In one embodiment, the first redox protein is at least 5 times more active when produced as a redox fusion polypeptide relative to production as a non-fusion polypeptide.

Accordingly, provided herein are methods for producing an oil body associated with a heteromultimeric redox protein complex, said method comprising:

(a) producing in a cell comprising oil bodies, a first redox protein and a second redox protein wherein said first redox protein is capable of interacting with said second redox protein, preferably in the cell, to form said heteromultimeric redox protein complex; and (b) associating said heteromultimeric redox protein complex with an oil body through an oil-body-targeting-protein capable of associating with said oil bodies and said heteromultimeric redox protein complex.

In a particular embodiment the first and second redox protein are prepared as a fusion protein to form a redox fusion polypeptide. Accordingly, provided herein are methods for preparing an enzymatically active redox protein associated with oil bodies comprising:

a) producing in a cell a redox fusion polypeptide comprising a first redox protein linked to a second redox protein;

b) associating said redox fusion polypeptide with oil bodies through an oil-body-targeting-protein capable of associating with said redox fusion polypeptide and said oil bodies; and c) isolating said oil bodies associated with said redox fusion polypeptide. The oil bodies in association with the redox protein may be used to prepare a variety of useful emulsions.

As used herein the phrase "redox proteins" or grammatical variations thereof, refers to any protein or active protein fragment capable of participating in electron transport. For example, redox proteins are capable of catalyzing the transfer of an electron from an electron donor (also frequently referred to as the reducing agent) to an electron acceptor (also frequently referred to as the oxidizing agent). In the process of electron transfer, the reducing agent (electron donor) is oxidized and the oxidizing agent (electron acceptor) is reduced. Exemplary redox proteins for use herein include iron-sulfur proteins, cytochromes, redox active thiol proteins and redox-active flavoproteins. To carry out their function as conduits for electron donors, redox proteins, such as thioredoxin and thioredoxin-reductase for example, are known to function by interacting or associating with one another in multimeric-protein-complexes (e.g., heteromultimeric-protein-complexes).

The term "redox fusion polypeptide" as used herein refers to any fusion polypeptide comprising a first redox protein linked to a second redox protein (e.g., an in-frame translational fusion). The redox proteins that may be used with the methods and compositions provided herein may be any redox protein. In one embodiment the first and second redox proteins are a pair of redox proteins that would normally occur together from the same source, in nature. In a particular embodiment, the first redox protein is a thioredoxin and the second redox protein is a thioredoxin-reductase.

The redox fusion polypeptide may be produced in any cell comprising oil bodies, including any animal cell, plant cell, algae cell, fungal cell or bacterial cell. In certain embodiments the redox fusion polypeptide is produced in a plant cell and in particular embodiments the redox fusion polypeptide is produced in the seed cells of a seed plant.

In particular embodiments the oil-body-targeting-protein that is used is an oil-body-protein. In embodiments of the present invention in which an oil-body-protein is used, the first and second redox protein are preferably covalently fused to the oil-body-protein. Accordingly, provided herein are methods for the preparation of a redox protein in association with an oil body comprising:

a) introducing into a cell a chimeric nucleic acid sequence comprising:

1) a first nucleic acid sequence capable of regulating transcription in said cell operatively linked to;

2) a second nucleic acid sequence encoding a recombinant fusion polypeptide comprising (i) a first nucleic acid sequence encoding a sufficient portion of an oil-body-protein to provide targeting of said recombinant fusion polypeptide to an oil body linked in reading frame to (ii) a second nucleic acid sequence encoding a redox fusion polypeptide comprising a first redox protein linked to a second redox protein operatively linked to;

3) a third nucleic acid sequence capable of terminating transcription in said cell;

b) growing said cell under conditions to permit expression of said redox fusion polypeptide in a progeny cell comprising oil bodies; and c) isolating said oil bodies comprising said redox fusion polypeptide from said progeny cell.

In particular embodiments, the redox proteins provided herein are thioredoxin and its reductant thioredoxin-reductase (which are jointly also referred to herein as "thioredoxin-related" protein(s)). As used herein, the term "thioredoxin" refers to relatively small proteins (typically approximately 12 kDa) that belong to the family of thiol-transferases which catalyze oxido-reductions via the formation or hydrolysis of disulfide bonds and are widely, if not universally, distributed throughout the animal plant and bacterial kingdom. The reduced form of thioredoxin is an excellent catalyst for the reduction of even the most intractable disulfide bonds. In order to reduce the oxidized thioredoxin, two cellular reductants provide the reduction equivalents: reduced ferredoxin and NADPH. These reduction equivalents are supplied to thioredoxin via interaction or association with different thioredoxin-reductases including the NADPH thioredoxin-reductase and ferredoxin thioredoxin-reductase. The supply of these reduction equivalents requires the formation of a heteromultimeric-protein-complex comprising thioredoxin and thioredoxin-reductase. Ferredoxin thioredoxin-reductase is involved in the reduction of plant thioredoxins designated as Trxf and Trxm, both of which are involved in the regulation of photosynthetic processes in the chloroplast. The NADPH/thioredoxin active in plant seeds is designated Trxh (also referred to herein as thioredoxin h-type) and is capable of the reduction of a wide range of proteins thereby functioning as an important cellular redox buffer. Generally, only one kind of thioredoxin, which analogous to the plant Trxh type, is found in bacterial or animal cells. The h-type thioredoxins are capable of being reduced by NADPH and NADPH-thioredoxin reductase.

Exemplary thioredoxins are further characterized as a protein having a core of 5 beta-sheets surrounded by 4 to 6 alpha helices. Exemplary thioredoxins are further characterized by having an active site containing the consensus amino acid sequence:

XCYYCZ, wherein Y is any amino acid, such as hydrophobic or non-polar amino acids, wherein X can be any of the 20 amino acids, preferably a hydrophobic amino acid, such as a tryptophan, and Z can be any amino acid, preferably polar amino acids.

In certain embodiments, the thioredoxins for use herein comprise an active site having the amino acid sequence X C G P C Z.

When the cysteines in the active site of thioredoxin or thioredoxin-like proteins are, they form an intramolecular disulfide bond. In the reduced state, the same active sites are capable of participating in redox reactions through the reversible oxidation of its active site dithiol, to a disulfide and catalyzes dithioldisulfide exchange reactions.

Exemplary thioredoxins are well-known in the art and can be obtained from several organisms including *Arabidopsis thaliana* (Riveira Madrid et al. (1995) Proc. Natl. Acad. Sci. 92: 5620–5624), wheat (Gautier et al. (1998) Eur. J. Biochem. 252: 314–324); *Escherichia coli* (Hoeoeg et al (1984) Biosci. Rep. 4: 917–923) and thermophylic microorganisms such as *Methanococcus jannaschii* and *Archaeoglobus fulgidus* (PCT Patent Application 00/36126). Thioredoxins have also been recombinantly expressed in several host systems including bacteria (Gautier et al. (1998) Eur J. Biochem. 252: 314–324) and plants (PCT Patent Application WO 00/58453) Commercial preparations of *E. coli* sourced Thioredoxins are readily available from for example: Sigma Cat No. T 0910 Thioredoxin (*E. coli*, recombinant; expressed in *E. coli*).

Exemplary nucleic acid sequences encoding thioredoxin polypeptides for use herein are readily available from a variety of diverse biological sources including *E. coli* (Hoeoeg et al. (1984) Biosci. Rep.: 4 917–923); *Methanococcus jannaschii* and *Archaeoglobus fulgidus* (PCT Patent Application 00/36126); *Arabidopsis thaliana* (Rivera-Madrid (1995) Proc. Natl. Acad. Sci. 92: 5620–5624); wheat (Gautier et al (1998) Eur. J. Biochem. 252(2): 314–324); tobacco (Marty et al. (1991) Plant Mol. Biol. 17: 143–148); barley (PCT Patent Application 00/58352); rice (Ishiwatari et al. (1995) Planta 195: 456–463); soybean (Shi et al. (1996) Plant Mol. Biol. 32: 653–662); rapeseed (Bower et al. Plant Cell 8: 1641–1650) and calf (Terashima et al. (1999) DNA Seq. 10(3): 203–205); and the like.

As used herein, the term "thioredoxin-reductase" refers to a protein that complexes with a flavin, such as FAD. The flavin compound serves as an electron donor for the thioredoxin-reductase protein active site. Thioredoxin reductases have a redox active, disulfide bond site capable of reducing thioredoxin. The active site of thioredoxin-reductase contains 2 cysteines. The type of amino acids surrounding the 2 cysteine residues forming the active site can vary as hydrophobic, non-polar or polar. An exemplary thioredoxin-reductase is NADPH-thioredoxin-reductase (TR), which is a cytosolic homodimeric enzyme comprising typically 300–500 amino acids. Crystal structures of both *E. coli* and plant thioredoxin-reductase have been obtained (Waksman et al. (1994) J. Mol. Biol. 236: 800–816; Dai et al. (1996) J. Mol. Biol. 264:1044–1057). NADPH-thioredoxin-reductases have been expressed in heterologous hosts, for example the *Arabidopsis* NADPH-thioredoxin-reductase has been expressed in *E. coli* (Jacquot et al. (1994) J. Mol. Biol. 235: 1357–1363) and wheat (PCT Patent Application 00/58453).

Exemplary nucleic acid sequences encoding thioredoxin-reductase proteins can readily be obtained from a variety of sources, such as from the sequence set forth in Table 5 and the Sequence Listing provide herein, from *Arabidopsis* (Riveira Madrid et al. (1995) Proc. Natl. Acad. Sci. USA 92: 5620–5624), *E. coli* (Russel et al. (1988) J. Biol. Chem. 263: 9015–9019); barley (PCT Patent Application 00/58352 and wheat (Gautier et al., (1998) Eur. J. Biochem. 252: 314–324); and the like.

Also contemplated for use in the methods and compositions provided herein are nucleic acid and amino acid homologs that are "substantially homologous" to the thioredoxin and thioredoxin-reductase nucleic and amino acids set forth herein, which includes thioredoxin and thioredoxin-reductase polypeptides encoded by a sequence of nucleotides that hybridizes under conditions of low, moderate or high stringency to the sequence of nucleotides encoding the thioredoxin and thioredoxin-reductase nucleic and amino acids set forth herein (e.g., in the Examples, Sequence Listing and/or Table 5). As used herein, a DNA or nucleic acid homolog refers to a nucleic acid that includes a preselected conserved nucleotide sequence, such as a sequence encoding a therapeutic polypeptide. By the term "substantially homologous" is meant having at least 80%, preferably at least 90%, most preferably at least 95% homology therewith or a less percentage of homology or identity and conserved biological activity or function.

The terms "homology" and "identity" are often used interchangeably. In this regard, percent homology or identity may be determined, for example, by comparing sequence information using a GAP computer program. The GAP program utilizes the alignment method of Needleman and Wunsch (*J. Mol. Biol.* 48:443 (1970), as revised by Smith and Waterman (*Adv. Appl. Math.* 2:482 (1981). Briefly, the GAP program defines similarity as the number of aligned symbols (i.e., nucleotides or amino acids) which are similar, divided by the total number of symbols in the shorter of the two sequences. The preferred default parameters for the GAP program may include: (1) a unary comparison matrix (containing a value of 1 for identities and 0 for non-identities) and the weighted comparison matrix of Gribskov and Burgess, *Nucl. Acids Res.* 14:6745 (1986), as described by Schwartz and Dayhoff, eds., *ATLAS OF PROTEIN SEQUENCE AND STRUCTURE,* National Biomedical Research Foundation, pp. 353–358 (1979); (2) a penalty of 3.0 for each gap and an additional 0.10 penalty for each symbol in each gap; and (3) no penalty for end gaps.

By sequence identity, the number of conserved amino acids are determined by standard alignment algorithms programs, and are used with default gap penalties established by each supplier. Substantially homologous nucleic acid molecules would hybridize typically at moderate stringency or at high stringency all along the length of the nucleic acid of interest. Preferably the two molecules will hybridize under conditions of high stringency. Also contemplated are nucleic acid molecules that contain degenerate codons in place of codons in the hybridizing nucleic acid molecule.

Whether any two nucleic acid molecules have nucleotide sequences that are at least 80%, 85%, 90%, 95%, 96%, 97%, 98% or 99% "identical" can be determined using known computer algorithms such as the "FAST A" program, using for example, the default parameters as in Pearson and Lipman, *Proc. Natl. Acad. Sci. USA* 85:2444 (1988). Alternatively the BLAST function of the National Center for Biotechnology Information database may be used to determine relative sequence identity.

In general, sequences are aligned so that the highest order match is obtained. "Identity" per se has an art-recognized meaning and can be calculated using published techniques. (See, e.g.: *Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM J Applied Math* 48:1073 (1988). Methods to determine identity and similarity are codified in computer programs. Preferred computer program methods to determine identity and similarity between two sequences include, but are not limited to, GCG program package (Devereux, J., et al., *Nucleic Acids Research* 12(l):387 (1984)), BLASTP, BLASTN, FASTA (Atschul, S. F., et al, *J Molec Biol* 215:403 (1990)).

Therefore, as used herein, the term "identity" represents a comparison between a test and a reference polypeptide or polynucleotide. For example, a test polypeptide may be defined as any polypeptide that is 90% or more identical to a reference polypeptide.

As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons may be made between a test and reference polynucleotides. Such differences may be represented as point mutations randomly distributed over the entire length of an amino acid sequence or they may be clustered in one or more locations of varying length up to the maximum allowable, e.g. 10/100 amino acid difference (approximately 90% identity). Differences are defined as nucleic acid or amino acid substitutions, or deletions.

As used herein: stringency of hybridization in determining percentage mismatch is as follows:
1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

Those of skill in this art know that the washing step selects for stable hybrids and also know the ingredients of SSPE (see, e.g., Sambrook, E. F. Fritsch, T. Maniatis, in: *Molecular Cloning, A Laboratory Manual,* Cold Spring Harbor Laboratory Press (1989), vol. 3, p. B.13, see, also, numerous catalogs that describe commonly used laboratory solutions). SSPE is pH 7.4 phosphate-buffered 0.18 NaCl. Further, those of skill in the art recognize that the stability of hybrids is determined by $T_m$, which is a function of the sodium ion concentration and temperature ($T_m$=81.5° C. −16.6($\log_{10}$[Na$^+$])+0.41(%G+C)−600/l)), so that the only parameters in the wash conditions critical to hybrid stability are sodium ion concentration in the SSPE (or SSC) and temperature.

It is understood that equivalent stringencies may be achieved using alternative buffers, salts and temperatures. By way of example and not limitation, procedures using conditions of low stringency are as follows (see also Shilo and Weinberg, *Proc. Natl. Acad. Sci. USA,* 78:6789–6792 (1981)): Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA (10×SSC is 1.5 M sodium chloride, and 0.15 M sodium citrate, adjusted to a pH of 7).

In a particular embodiment, a heteromultimeric-protein-complex is produced as a fusion polypeptide between the first and second redox protein, wherein the first redox protein is thioredoxin and the second redox protein is a thioredoxin-reductase. In one embodiment, the second recombinant polypeptide, e.g., the thioredoxin-reducase is positioned N-terminal relative to the first recombinant polypeptide, e.g., the thioredoxin. Accordingly, any protein which is classified as thioredoxin, such as the thioredoxin component of the NADPH thioredoxin system and the thioredoxin present in the ferredoxin-thioredoxin system also known as TRx and TRm may be used in combination with any thioredoxin-reductase such as the NADPH thioredoxin-reductase and the ferredoxin-thioredoxin-reductase and any other proteins having the capability of reducing thioredoxin. In particular embodiments the thioredoxin and thioredoxin-reductase are plant derived.

In an alternate embodiment, the naturally occurring nucleic acid sequence encoding the thioredoxin/thioredoxin-reductase protein fusion obtainable from *Mycobacterium leprae* (Wieles et al. (1995) J. Biol. Chem. 27:25604–25606) is used, as set forth in the Examples herein.

Immunoglobulins

In another embodiment of the present invention, the multimeric-protein-complexes are immunoglobulins. As used herein "immunoglobulin-polypeptide-chain" refers to a polypeptide comprising an immunoglobulin fold. "Immunoglobulin fold" as used herein refers to a barrel shaped protein structure comprising 2 β-sheets comprising several (e.g. seven in the case of a light chain C-domain of an IgG) anti-parallel β-strands held together by a disulfide bond. This includes any immunoglobulin or immunoglobulin-like proteins including portions of fragments thereof. The types of immunoglobulins and immunoglobulin-polypeptide-chains contemplated for use herein include the immunologically active (i.e. antigen binding) portions of a light or heavy chain of an antibody, as well as other polypeptides comprising an immunoglobulin fold, for example the immunoglobulin C-like domain and V-like domain of a T-cell receptor, and the antigen-binding domains of the MHC class of molecules, such as the α and β antigen binding domains of CD8. In a specific embodiment, the immunoglobulin-polypeptide chain is an immunoglobulin heavy chain or an immunoglobulin light chain or portions thereof. In preferred embodiments, the first immunoglobulin polypeptide is an immunoglobulin-light-chain, or an immunologically active fragment thereof, of an antibody, such as the VL fragment, and the second immunoglobulin polypeptide is an immunoglobulin-heavy-chain or an immunologically active fragment thereof of an antibody, such as the VH domain. The immunoglobulin-light-chain can be a k- or κ-light chain or an immunologically active fragment thereof. The immunoglobulin heavy chain can be a γ-, μ-, α-, ε- or δ-heavy chain or an immunologically active fragment thereof. Exemplary immunoglobulins for use herein include substantially intact immunoglobulins, including any IgG, IgA, IgD, IgE and IgM, as well as any portion of an immunoglobulin, including those portions well-known as Fab fragments, Fab' fragments, F(ab')$_2$ fragments and Fv fragments.

In this embodiment, the first recombinant polypeptide may be any immunoglobulin heavy chain, including any IgG, IgA, IgD, IgE or IgM heavy chain, and the second recombinant polypeptide may be a kappa or lambda immunoglobulin light chain. The immunoglobulin that may be used in accordance with the present invention may be capable of binding any antigenic determinant, including such determinants that are associated with any disease or condition. Accordingly, provided herein are methods of producing an immunoglobulin, said method comprising: (a) producing in a cell comprising oil bodies, a first immunoglobulin-polypeptide-chain and a second immunoglobulin-polypeptide-chain wherein said first immunoglobulin-polypeptide-chain is capable of associating with said second immunoglobulin-polypeptide-chain to form said immunoglobulin; and (b) associating said immunoglobulin with an oil body through an oil-body-targeting-protein capable of associating with said oil bodies and said first immunoglobulin-polypeptide-chain.

Also provided herein are methods for preparing a multimeric immunoglobulin associated with oil bodies comprising:

a) introducing into a cell a chimeric nucleic acid sequence comprising:
1) a first nucleic acid sequence capable of regulating transcription in said cell operatively linked to;
2) a second nucleic acid sequence encoding a recombinant fusion polypeptide comprising (i) a nucleic acid sequence encoding a sufficient portion of an oil-body-protein to provide targeting of said recombinant fusion polypeptide to an oil body linked to (ii) a nucleic acid sequence encoding a immunoglobulin comprising a first immunoglobulin-polypeptide-chain linked to a second immunoglobulin-polypeptide-chain, operatively linked to;
3) a third nucleic acid sequence capable of terminating transcription in said cell;

b) growing said cell under conditions to permit expression of said multimeric-immunoglobulin in a progeny cell comprising oil bodies; and c) isolating from said progeny cell said oil bodies comprising said multimeric immunoglobulin.

The present invention also provides a chimeric nucleic acid comprising:
1) a first nucleic acid sequence capable of regulating transcription in a host cell operatively linked to;
2) a second nucleic acid sequence encoding a recombinant fusion polypeptide comprising (i) a nucleic acid sequence encoding a sufficient portion of an oil-body-protein to provide targeting of said recombinant fusion polypeptide to an oil body linked to (ii) a nucleic acid sequence encoding an immunoglobulin comprising a first immunoglobulin polypeptide chain linked to a second immunoglobulin polypeptide chain operatively linked to;
3) a third nucleic acid sequence capable of terminating transcription in said cell.

The term "sufficient portion of an oil body protein" means that a nucleic acid sequence would be used that encodes enough of an oil body protein to allow for targeting of the recombinant fusion polypeptide to the oil bodies in the host cell. In general, the N-terminus and the hydrophobic core of an oil body protein (such as an oleosin) are sufficient to provide targeting of a recombinant fusion protein to the oil bodies in a cell.

Preparation of Immunoglobulin cDNAs

For expression of multimeric-protein-complexes containing multimeric-immunoglobulin-complexes, the cDNA sequences encoding individual light immunoglobulin and heavy immunoglobulin chains can be prepared from any appropriate source, including for example cell lines expressing a particular antibody, such as a hybridoma cell line, or clonal B cell lines, or may be prepared as recombinant antibody, assembled by combining select light and heavy chain variable domains and available light and heavy chain constant domain sequences, respectively. Variable domains with specific binding properties may be isolated from screening populations of such sequences, usually in the form of a single-chain Fv phage display library.

Methodologies to create hybridomas are well known to the an and vary depending on the cell type that is selected (see e.g., Harlow, E and Lane D, in: *Antibodies, A Laboratory* Manual, Cold Spring Harbor Laboratory Press (1988) p 139–243.) The production of monoclonal antibodies using hybridomas is usually accomplished by fusing mouse myelomas and mice antibody-secreting cells but rat or human cells, or other appropriate cells may also be used. Interspecies fusions (e.g. the immunization of rats and the fusion of rat B-cells with mouce myeloma cells) may also be performed. For the purpose of the present application, the production of mouse hybridomas is described: the production of mouse monoclonal antibodies can be divided into three stages: (1) immunization of the mice, (2) development of the screening procedure and (3) the production of the hybridomas. Mouse immunization involves injection of a mouse with the antigen and preferably the addition of an adjuvant (i.e. Freund's complete which contains killed *Mycobacterium tuberculosis* bacterium (initial injection) and Freund's incomplete antigen without the bacterium (subsequent injections)). Injection can include one or more of the following sites including intraperitoneal, subcutaneous, intravenous, intramuscular, intradermal and lymph node. Multiple injections or boosters are performed to ensure that a high antibody titre results. Antibody titre may be tested by collecting a tail bleed and preparing blood serum. A tail bleed is performed by swabbing a portion of the mouse tail about 1.5–2 inches from the body with alcohol and nicking the underside of the tail across one of the lower veins using a sterile scalpel. Several drops of blood are collected and the blood is incubated at 37° C. for 1 hour and subsequently flicking the side of the tube to dislodge the blood clot. The tube is transferred to 4° C. for a minimum of 2 hours or overnight. The tube is spun at 10,000 g for 10 minutes at 4° C., the serum collected. The serum is respun a second time for 10 minutes and the supernatant is carefully collected and 0.02% sodium azide is added. 1 in 5 dilutions of the serum samples in PBS (phosphate buffered saline) are compared with similar dilutions of normal mouse serum using for example in a dot blot. A dot blot is used when the antigen is a protein that is available in large amounts. The antigen is bound directly to a nitrocellulose sheet. An alternative to a dot blot may be the use of polyvinylchloride multi-well plates. To perform a dot blot, a protein solution of at least 1 μg/ml is placed on a nitrocellulose sheet at 0.1 ml/cm$^2$ and allowed to bind for a period of 1 hour. The nitrocellulose sheet is subsequently washed three times in PBS and placed in a solution of 3% BSA (bovine serum albumin) with 0.02% sodium azide for a period of 2 hours or overnight. The nitrocellulose sheet is cut into squares so that each sample may be tested. 1 μl of a diluted test bleed is blotted on the sheet and allowed to incubate in a humid atmosphere for 30 minutes. The presence of the antibody can be detected using multiple methods including $^{125}$I-labeled rabbit anti-mouse immunoglobulin or a horse radish peroxidase associated anti-mouse immunoglobulin. The mouse is then typically boosted to further increase the levels of antibodies. Positives may be evaluated further for antibody titre, affinity for the antigen, and appearance of spurious antibody activities against unrelated antigens. The decision to boost the mouse or proceed to fusion involves three factors: (1) whether the antibody recognizes the antigen of interest, (2) the different titres of the antibodies and different affinities of the antibody for the antigen and (3) the appearance of spurious antibody activities against unrelated antigens. To test whether the antibody recognizes the antigen of interest the dot blot performed above is likely sufficient but it is suggested that the antibody should be checked in assays that resemble the tests for which the antibody is being prepared for, i.e. immunoprecipitation, immunoblot analysis, immunohistochemical staining. To test whether the concentration of specific antibodies is appropriate, the test bleeds should be titred in appropriate assays, i.e. ELISA assay. As the immune response matures, increased levels of the antibody will be found. It should be noted that increased amounts of the antibody does not necessarily indicate that the antibody has a higher affinity to the antigen. Assays that are sensitive to affinity include immunoprecipitation. The final factor is the appearance of antibody activities against other, extraneous antigens (i.e. contaminating antigens in the sample, or antigens in response to antigens in the mouse's environment, including pathogenic organisms).

The next stage in creating hybridomas is the development of the screening procedure. A good screening procedure must reduce the number of cultures to be maintained to a reasonable level (50 cultures maximum is preferable), identify the potential positives within 48 hours, more preferably within 24 hours and be easy to perform as multiple samples will need to be tested. It is suggested that all screening procedures be tested and validated before the hybridoma fusions begin. In general, there are three different classes of screening strategies, antibody capture assays, antigen capture assays and functional screenings.

In general antibody capture assays the often the easiest and most convenient of the methods. The procedure for an antibody capture assay involves binding the antigen to a solid substrate, binding of the antibody from either the test bleed or subsequently the hybridoma tissue culture to the antigen, removing unbound antibody with washing and detecting the bound antibody with a secondary reagent that will specifically recognize the antibody. Most of these methods rely on an indirect method of detecting the antibody, most commonly done using a secondary antibody, for example a rabbit anti-mouse immunoglobulin antibody. Examples of secondary antibody labels or tags include iodine which is detected using X-ray film, an enzyme like horse radish peroxidase detected using chromogenic substrates, biotin which is detected using avidin/spreptavidin coupled to various labels and fluorochromes detected using a fluorescence microscope or fluorimeter. Alternatively, positives can be located using other reagents that bind specifically to antibodies like Protein A or Protein G labeled with an appropriate tag. The dot blot described above is indicative of an antibody capture assay. Other procedures including antibody capture in polyvinylchloride wells using 125I detection, antibody capture in polyvinylchloride wells using enzyme linked detection, antibody capture on whole cells using cell surface binding and antibody capture of permeabilized cells using cell staining are described in Harlow, E and Lane D, in: *Antibodies, A Laboratory Manual*, Cold Spring Harbor Laboratory Press (1988) p 180–187.

The second screening strategy is the antigen capture assay. This method identifies the presence of the antigen by labeling the antigen directly and requires the antibody to have a high affinity since the labeled antigen is added in very low concentrations. In general the procedure for an antigen capture assay includes binding the antibody-antigen complex to a solid support, removing any unbound antigen by washing and identifying positives by detecting the antigen. Two variations exist for the antigen capture assay. In the first variation the antibody is bound to a solid phase first and the antigen is allowed to react with the antibody. In the second variation, the antibody-antigen complex is allowed to form prior to binding the antibody to the solid phase. Detection of the antigen can be done by pre-labeling the antigen with a radiolabel, fluorescent label or by coupling an enzyme to the antigen. Alternatively if the antigen itself is an enzyme, positives may be identified by the presence of enzymatic activity. An example of an antigen capture assay is the reverse dot blot. To perform a reverse dot blot nitrocellulose paper is cut to the size of the dot blot apparatus and 10 ml/100 cm² of rabbit anti-mouse immunoglobulin solution (approximately 200 μg of purified antibody/ml in PBS). Rabbit anti-mouse immunoglobulin can be purified using protein A beads or alternatively purchased from a commercial source. The solution is incubated with the nitrocellulose paper for 60 minutes at room temperature. After incubation the paper is washed three times with PBS for a period of 5 minutes for each wash. The paper is subsequently incubated in 3% BSA/PBS with 0.02% sodium azide for 1 hour at room temperature and loaded into a 96-well dot blot apparatus. 50 μl of either hybridoma tissue culture supernatant or serum from a test bleed are added to each well and incubated for a period of 1 hour at room temperature to allow for the mouse antibody to bind to the rabbit anti-mouse immunoglobulin. The supernatant is drawn through the nitrocellulose paper using a vacuum and the paper is subsequently washed three times with 3% BSA/PBS. The paper is removed from the apparatus and incubated with labeled antigen at room temperature for 1 hour with shaking. If for example $^{125}$I-labeled antigen is used 10 ml/96-well sheet, 50,000 cpm/well in 3% BSA/PBS is used. The paper is then washed with PBS until the counts in the wash butter approach background levels. The paper is then covered in plastic wrap and exposed to X-ray film at −70° C. with a screen. Other examples of antigen capture assays including antigen capture in polyvinylchloride wells and antigen capture in solution using immunoprecipitation are described in Harlow, E and Lane D, in: *Antibodies, A Laboratory Manual*, Cold Spring Harbor Laboratory Press (1988) p 192–194.

The final screening assay is a functional assay. In a functional assay the antibodies in the hybridoma tissue culture supernatant or test bleed serum is used to either block a reaction or as a molecular handle to deplete an essential component of a reaction mixture. It should be noted that these assays are difficult to perform and interpret and a seldom used.

Once a good immune response has been achieved in the animal and a good screening procedure is developed, the final step is the creation of hybridomas. In general the procedure for producing hybridomas includes isolating antibody-secreting cells from the appropriate lymphoid tissue, mixing the cells with myeloma cells, centrifuging the two cell types to generate good cell-to-cell contact the fusing the cells with PEG (polyethylene glycol). The fused cells are subsequently diluted into selective media and plated in multi-well tissue culture dishes. Approximately 1 week later the supernatants are removed and tested for the presence of the desired antibody. The cells from the positive wells are grown, single-cloned and frozen.

It should be noted that approximately 3 to 5 days before the fusion, the mice should be given one final boost. The final boost should be administered at least 3 weeks after the previous injection to allow for the circulating antibodies to be cleared from the blood serum by the mouse. Waiting the 3-week time period will prevent high level of circulating antibodies from binding to the injected antigen and lowering the effectiveness of the final boost. This is due to the fact that serum antibody titres decrease approximately 14 days following injection of an antigen. The purpose of the final boost is to induce a good, strong response and to synchronize the maturation of the response (i.e. a substantial number of antigen-specific lymphocytes will be present 3–4 days after the final boost.).

The myeloma cells are prepared by thawing the cells from liquid nitrogen stocks at least 6 days prior to the fusion procedure. The myelomas should be growing rapidly and healthy before the fusion. One day before the fusion, the myelomas cells should be split into fresh medium supplemented with 10% fetal bovine serum (available commercially) so that the cells are at a concentration of 5×10⁵ cells/ml. 10 ml of the overnight culture is subsequently diluted with an equal volume of medium supplemented with 20% fetal bovine serum and 2×OPI. (100 mls of 100×OPI is prepared by dissolving 1.5 grams of oxaloacetate, 500 mg of sodium pyruvate in 100 mls of water that is suitable for tissue culture work. 2000 IU of bovine insulin is added to the solution and the solution is filtered sterilized.)

The splenocytes are isolated from the spleen of a sacrificed mouse. The spleen is aseptically removed from an immunized mouse and placed in a 100-mm tissue culture dish containing 10 ml of medium without serum which has been prewarmed to 37° C. Contaminating tissue from the spleen is trimmed off and discarded. The spleen is teased apart using a 19-gauge needle on a 1.0 ml syringe until the majority of the cells have been released and the spleen is torn into small particles. Cell clumps can be disrupted by pipetting. The cells and medium are transferred into a sterile centrifuge tube leaving any larger pieces of spleen tissue behind. The tissue culture plate and tissue clumps are washed with 10 ml of medium without serum which has been prewarmed to 37° C. and the solution is combined with the first 10 mls. The cell suspension is allowed to settle for approximately 2 minutes and the supernatant is carefully removed and transferred to a fresh centrifuge tube.

Fusion of the splenocytes and the melanocytes can be performed by stirring in the presence of 50% PEG (polyethylene glycol). PEG is prepared by melting PEG 1500 in a 50° C. water bath. 0.5 grams of PEG is placed in a small glass vial. The vial is capped and autoclaved to sterilize the PEG mixture. It should be noted that PEG 1500 is usually used for fusions but the range of PEG 1000 to PEG 6000 can also be used. The first step is the fusion of splenocytes and melanocytes is the washing of the splenocytes twice by centrifugation in 400 ml of medium without serum (prewarmed to 37° C.). During the second wash, the melanocytes can also be washed in a second centrifuge tube containing 20 ml of medium without serum. During these washes, the vial with 0.5 grams of PEG is melted in a 50° C. water bath. Once the PEG has melted, 0.5 ml of medium without serum is added and the vial is transferred to a 37° C. water bath. After the splenocytes and melanocytes have been washed the two cell pellets are resuspended in medium without serum (prewarmed to 37° C.) and combined. The cells are centrifuged together at 800 g for 5 minutes and after centrifugation the medium is carefully removed. The 50% PEG solution is removed from its vial with a Pasteur pipette and slowly added to the cell pellet while resuspending the cells by stirring with the end of the pipette. This procedure should take approximately 1 minute with stirring for an additional minute. A 10-ml pipette is filled with 10 ml of medium without serum (prewarmed to 37° C.). 1.0 ml of the medium is added to the cell suspension over the next minute with continued stirring with the end of the pipette. The remaining 9.0 mls is added over the next 2 minutes with continuous stirring. The final mixture is centrifuged at 400 g for 5 minutes. The supernatant is removed and the cells are resuspended in 10 ml of medium supplemented with 20% fetal bovine serum (prewarmed to 37° C.), 1×OPI and 1×AH. (100 ml of 100×AH is prepared ahead of time by adding 0.136 grams of hypoxanthine in water suitable for tissue culture, heated to 70° C. to dissolve with a subsequent addition of 10 mg of azaserine. The solution is filter sterilized and dispensed into sterile tubes in 2.0 ml aliquots. 100×AH can be stored at −20° C. for a period of 1 year.) The cells are transferred to 200 ml of medium with 20% pre-screened fetal bovine serum (prewarmed to 37° C.), 1×OPI and 1×AH. 100 μl of cells are dispensed into the wells of 20 96-well microtite plates and placed at 37° C. in a $CO_2$ incubator.

Screening of hybridomas can be done approximately 7 to 14 days after the fusion. For most screening procedures, clones that are just visible by the eye are acceptable for screening. Due to the large number of hybridomas to screen on the first day it may be advisable to pool the supernatants to reduce the total number of tests to be performed. The most widely used method is a simple combination of several tissue culture supernatants. A possible disadvantage of this method is that the positive well in the pool will need to be identified by immediately rescreening. The use of a 2 dimensional matrix (i.e. pooling each vertical column and each horizontal row) can be used to identify positives. The positive clone can be identified by the location of intersecting positives. It should be noted that the matrix should only be used if the positive supernatants are likely to be rare. The screening method used to screen the hybridomas will have been determined in the development of the screening procedure discussed above. When the clones are ready to be screened 50 μl of supernatant is aseptically removed without disturbing the hybridoma and transferred to a suitable container. After the removal of the supernatant, fresh medium should be added to the hybridomas.

After the positives clones have been identified, the cells are transferred from the 96-well plate to 0.5 ml of medium supplemented with 20% fetal bovine serum, 1×OPI and 1×AH in a 24-well plate. Once the cultures become dense, the cells are transferred into 5.0 ml in a 60-mm dish and then to 10 ml in a 100-mm dish. At the 100-mm dish stage the cells should be frozen. The next step is to clone the antibody-producing cell so that only one clone of the hybridoma cells is present. The single-cell cloning ensures that monoclonal antibodies are being produced and that the secretion of the antibody can be maintained. The easiest single cell cloning technique is limiting dilution. Note that limiting dilution should be done at least twice to ensure that colonies do not arise from two cells that were stuck together. Limiting dilution is performed by adding 50 μl of medium with 20% FBS and 2×OPI to each well of a 96-well place already containing 50 μl of feeder cells giving 100 μl total volume. (Splenocyte feeder cells are prepared as described above for the splenocytes except that the source of the spleen is a female mouse of the same genetic background as the hybridoma). 100 μl of the hybridoma cell suspension is removed using a pipetteman and transferred to the top left-hand well. 1 in 2 doubling dilutions are done down the left-hand row of the plate and the tip discarded. 1 in 2 doubling dilutions are subsequently performed across the plate using an 8-well multipipetter. Clones should be visible within a few days using microscopy and should be ready to screen after 7 to 10 days.

Once the hybridoma has been cloned messenger RNA coding for the heavy and light chain can be isolated employing standard techniques of RNA isolation and using oligo-dT cellulose chromatography to segregate the poly-A mRNA. A cDNA library is prepared from the mixture of RNA using a suitable primer. The primer is preferably a nucleic acid sequence which is characteristic of the desired cDNA. It the sequence of the antibody is known then the primer may be hypothesized based on the known amino acid sequence. In the present invention, cDNA must be used so that the DNA to be subsequently introduced into the selected host system is free from introns.

For expression of multimeric-protein-complexes containing multimeric-immunoglobulin-complexes, the cDNA sequences encoding individual light and heavy chains may be a recombinant antibody, assembled by combining select light and heavy chain variable domains and available light and heavy chain constant domain sequences, respectively. For example a chimeric antibody is constructed using mouse variable domains and human constant domains for both the heavy and light chains. Variable domains with specific binding properties may be isolated from screening populations of such sequences, usually in the form of a single-chain Fv phage display library. Or alternatively if the sequence of the mouse variable domain is known for either the heavy or light chain, PCR primers can be readily designed to amplify the variable region which can subsequently be fused to the a human constant region for the appropriate heavy or light chain. If the sequence is not known, degenerate primers to mouse immunoglobulin gene variable regions have been designed (see for example Wang et al. (2000) J. Immunological Methods 233: 167–177) for Reverse Transcription Polymerase Chain Reaction.

The nucleic acid sequences encoding the heavy and light antibody chains may be altered to improve expression levels for example by optimizing the nucleic acids sequence in accordance with the preferred codon usage for the particular cell type which is selected for expression of the heavy and light antibody chains, or by altering of motifs known to destabilize mRNAs (see for example: PCT Patent Application 97/02352). Comparison of the codon usage of the heavy and light antibody chains with codon usage of the host will enable the identification of codons that may be changed. For example, typically plant evolution has tended towards a preference for CG rich nucleotide sequences while bacterial evolution has resulted in bias towards AT rich nucleotide sequences. By modifying the nucleic acid sequences to incorporate nucleic acid sequences preferred by the host cell, expression may be optimized. Construction of synthetic genes by altering codon usage is described in for example PCT patent Application 93/07278. The heavy and light antibody chain genes may be altered using for example, targeted mutagenesis, random mutagenesis (Shiraishi et al. (1998) Arch. Biochem. Biophys. 358: 104–115; Galkin et al. (1997) Protein Eng. 10: 687–690; Carugo et al. (1997) Proteins 28: 10–28; Hurley et al. (1996) Biochemistry 35: 5670–5678) (and/or by the addition of organic solvent (Holmberg et al. (1999) Protein Eng. 12: 851–856).

As set forth herein, the multimeric immunoglobulin is associated with an oil body through an oil-body-targeting-protein. In particular embodiments, the oil-body-targeting-protein may be a fusion polypeptide comprising an oil-body-protein and an immunoglobulin binding protein, such as for example protein A, protein L, and protein G. In this embodiment the first recombinant polypeptide may be an immunglobulin heavy chain, including any IgG, IgA, IgD, IgE or IgM heavy chain and the second recombinant polypeptide may be a kappa or lambda immunoglobulin light chain.

In yet another embodiment involving immunoglobulins, the first and second recombinant polypeptides (immunoglobulins) are separately fused to an oil body protein, for example an oleosin or caleosin. For example, a) the first recombinant polypeptide may be an immunoglobulin heavy chain, including any IgG, IgA, IgD, IgE or IgM heavy chain, and the second recombinant polypeptide may be a kappa or lambda immunoglobulin light chain; or b) the first recombinant polypeptide may be the variable and first constant domain from an immunoglobulin heavy chain and the second recombinant polypeptide may be a kappa or lambda immunoglobulin light chain; or c) the first recombinant polypeptide may be the variable domain from an immunoglobulin heavy chain and the second recombinant polypeptide may be the variable domain from a kappa or lambda immunoglobulin light chain.

In certain embodiments, the fusion polypeptides are designed or selected to allow the heteromultimeric-protein-complex formation between immunoglobulin light and heavy chain sequences on the oil bodies within the cell comprising oil bodies.

Preparation of Expression Vectors Comprising oil-body-targeting-proteins and the First and/or Second Recombinant Polypeptides, Multimeric-protein-complexes, Heteromultimeric-protein-complexes, Multimeric-fusion-proteins, Heteromultimeric-fusion-proteins, Immunoglobulins, Immunoglobulin-polypeptide-chains, Redox-fusion-polypeptides, or the First and/or Second Thioredoxin-related Proteins In accordance with the present invention, the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins; and the oil-body-targeting-protein are conveniently produced in a cell. In order to produce the recombinant polypeptides or multimeric-protein-complexes, a nucleic acid sequence encoding either the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins; and/or the oil-body-targeting-protein are incorporated in a recombinant expression vector. Accordingly, provided herein are recombinant expression vectors comprising the chimeric nucleic acids provided herein suitable for expression of the oil-body-targeting-protein and the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins, suitable for the selected cell. The term "suitable for expression in the selected cell" means that the recombinant expression vector contains all nucleic acid sequences required to ensure expression in the selected cell.

Accordingly, the recombinant expression vectors further contain regulatory nucleic acid sequences selected on the basis of the cell which is used for expression and ensuring initiation and termination of transcription operatively linked to the nucleic acid sequence encoding the recombinant polypeptide or multimeric-protein-complex and/or the oil-body-targeting-protein. Regulatory nucleic acid sequences include promoters, enhancers, silencing elements, ribosome binding sites, Shine-Dalgarno sequences, introns and other expression elements. "Operatively linked" is intended to mean that the nucleic acid sequences comprising the regulatory regions linked to the nucleic acid sequences encoding the recombinant polypeptide or multimeric-protein-complex and/or the oil-body-targeting-protein allow expression in the cell. A typical nucleic acid construct comprises in the 5' to 3' direction a promoter region capable of directing expression, a coding region comprising the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins; and/or an oil-body-targeting-protein and a termination region functional in the selected cell.

The selection of regulatory sequences will depend on the organism and the cell type in which the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins; and/or the oil-body-targeting-protein is expressed, and may influence the expression levels of the polypeptide. Regulatory sequences are art-recognized and selected to direct expression of the oil-body-targeting-protein and the recombinant polypeptides or multimeric-protein-complexes in the cell.

Promoters that may be used in bacterial cells include the lac promoter (Blackman et al. (1978) Cell: 13: 65–71), the trp promoter (Masuda et al. (1996) Protein Eng: 9: 101–106) and the T7 promoters (Studier et al. (1986) J. Mol. Biol. 189: 113–130). Promoters functional in plant cells that may be used herein include constitutive promoters such as the 35S CaMV promoter (Rothstein et al. (1987) Gene: 53: 153–161) the actin promoter (McElroy et al. (1990) Plant Cell 2: 163–171) and the ubiquitin promoter (European Patent Application 0 342 926). Other promoters are specific to certain tissues or organs (for example, roots, leaves, flowers or seeds) or cell types (for example, leaf epidermal cells, mesophyll cells or root cortex cells) and or to certain stages of plant development. Timing of expression may be controlled by selecting an inducible promoter, for example the PR-a promoter described in U.S. Pat. No. 5,614,395. Selection of the promoter therefore depends on the desired location and timing of the accumulation of the desired polypeptide. In a particular embodiment, the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins; and the oil-body-targeting-protein are expressed in a seed cell and seed specific promoters are utilized. Seed specific promoters that may be used herein include for example the phaseolin promoter (Sengupta-Gopalan et al. (1985) Proc. Natl. Acad. Sci. USA: 82: 3320–3324), and the *Arabidopsis* 18 kDa oleosin promoter (van Rooijen et al. (1992) Plant. Mol. Biol. 18: 1177–1179). New promoters useful in various plant cell types are constantly discovered. Numerous examples of plant promoters may be found in Ohamuro et al. (Biochem of Pl. (1989) 15: 1–82).

Genetic elements capable of enhancing expression of the polypeptide may be included in the expression vectors. In plant cells these include for example, the untranslated leader sequences from viruses such as the AMV leader sequence (Jobling and Gehrke (1987) Nature: 325: 622–625) and the intron associated with the maize ubiquitin promoter (See: U.S. Pat. No. 5,504,200).

Transcriptional terminators are generally art recognized and besides serving as a signal for transcription termination serve as a protective element serving to extend the mRNA half-life (Guarneros et al. (1982) Proc. Natl. Acad. Sci. USA: 79: 238–242). In nucleic acid sequences for the expression in plant cells, the transcriptional terminator typically is from about 200 nucleotide to about 1000 nucleotides in length. Terminator sequences that may be used herein include for example, the nopaline synthase termination region (Bevan et al. (1983) Nucl. Acid. Res.: 11: 369–385), the phaseolin terminator (van der Geest et al. (1994) Plant J.: 6: 413–423), the terminator for the octopine synthase gene of *Agrobacterium tumefaciens* or other similarly functioning elements. Transcriptional terminators can be obtained as described by An (1987) Methods in Enzym. 153: 292). The selection of the transcriptional terminator may have an effect on the rate of transcription.

Accordingly, provided herein are chimeric nucleic acid sequences encoding a first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, and/or thioredoxin-related proteins. In one embodiment, said nucleic acid comprises:

(a) a first nucleic acid sequence encoding an oil-body-targeting-protein operatively linked in reading frame to;

(b) a second nucleic acid sequence encoding a first recombinant polypeptide, immunoglobulin-polypeptide-chain, or redox protein; linked in reading frame to;

(c) a third nucleic acid sequence encoding a second recombinant polypeptide, immunoglobulin-polypeptide-chain or redox protein, wherein said first and second recombinant polypeptides, immunoglobulin-polypeptide-chains or redox proteins are capable of forming a multimeric-protein-complex.

In another embodiment, provided herein is an expression vector comprising:

1) a first nucleic acid sequence capable of regulating transcription in said cell operatively linked to;

2) a second nucleic acid sequence encoding a recombinant fusion polypeptide comprising (i) a nucleic acid sequence encoding a sufficient portion of an oil-body-protein to provide targeting of said recombinant fusion polypeptide to an oil body linked in reading frame to (ii) a nucleic acid sequence encoding a multimeric-fusion-protein, such as a redox fusion polypeptide or immunoglobulin, comprising a first recombinant polypeptide, such as a redox protein or immunoglobulin-polypeptide-chain, linked to a second recombinant polypeptide, such as a second redox protein or a second immunoglobulin-polypeptide-chain, operatively linked to;

3) a third nucleic acid sequence capable of terminating transcription in said cell.

The recombinant expression vector further may contain a marker gene. Marker genes that may be used in accordance with the present invention include all genes that allow the distinction of transformed cells from non-transformed cells including all selectable and screenable marker genes. A marker may be a resistance marker such as an antibiotic resistance marker against for example kanamycin, ampicillin, G418, bleomycin hygromycin, chloramphenicol which allows selection of a trait by chemical means or a tolerance marker against for example a chemical agent such as the normally phytotoxic sugar mannose (Negrotto et al. (2000) Plant Cell Rep. 19: 798–803). In plant recombinant expression vectors herbicide resistance markers may conveniently be used for example as markers conferring resistance against glyphosate (U.S. Pat. Nos. 4,940,935 and 5,188,642) or phosphinothricin (White et al. (1990) Nucl. Acids FRes. 18: 1062; Spencer et al. (1990) Theor. Appl. Genet. 79: 625–631). Resistance markers to a herbicide when linked in close proximity to the redox protein or oil-body-targeting-protein may be used to maintain selection pressure on a population of plant cells or plants for those plants that have not lost the protein of interest. Screenable markers that may be employed to identify transformants through visual observation include beta-glucuronidase (GUS) (see US Patents U.S. Pat. No. 5,268,463 and U.S. 5,599,670) and green fluorescent protein (GFP) (Niedz et al. (1995) Plant Cell Rep.: 14: 403).

The recombinant expression vectors further may contain nucleic acid sequences encoding targeting signals ensuring targeting to a cell compartment or organelle. Suitable targeting signals that may be used herein include those that are capable of targeting polypeptides to the endomembrane system. Exemplary targeting signals that may be used herein include targeting signals capable of directing the protein to the periplasm, the cytoplasm, the golgi apparatus, the apoplast (Sijmons et al., 1990, Bio/Technology, 8:217–221) the chloroplast (Comai et al. (1988) J. Biol. Chem. 263: 15104–15109), the mitochondrion, the peroxisome (Unger et al. (1989) Plant Mol. Biol. 13: 411–418), the ER, the vacuole (Shinshi et al. (1990) Plant Mol. Biol. 14: 357–368 and the oil body. By the inclusion of the appropriate targeting sequences it is possible to direct the oil-body-targeting-protein or the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, and/or thioredoxin-related proteins, to the desired organelle or cell compartment.

The recombinant expression vectors of the present invention may be prepared in accordance with methodologies well known to those of skill in the art of molecular biology (see for example: Sambrook et al. (1990) Molecular Cloning, $2^{nd}$ed. Cold Spring Harbor Press). The preparation of these constructs may involve techniques such as restriction digestion, ligation, gel electrophoresis, DNA sequencing and PCR. A wide variety of cloning vectors is available to perform the necessary cloning steps resulting in a recombinant expression vector ensuring expression of the polypeptide. Especially suitable for this purpose are vectors with a replication system that is functional in *Escherichia coli* such as pBR322, the PUC series of vectors, the M13mp series of vectors, pBluescript etc. Typically these vectors contain a marker allowing the selection of transformed cells for example by conferring antibiotic resistance. Nucleic acid sequences may be introduced in these vectors and the vectors may be introduced in *E. coli* grown in an appropriate medium. Vectors may be recovered from cells upon harvesting and lysing the cells.

Recombinant expression vectors suitable for the introduction of nucleic acid sequences in plant cells include *Agrobacterium* and Rhizobium based vectors such as the Ti and Ri plasmids. *Agrobacterium* based vectors typically carry at least one T-DNA border sequence and include vectors such pBIN 19 (Bevan (1984) Nucl Acids Res. Vol. 12, 22:8711–8721) and other binary vector systems (for example: U.S. Pat. No. 4,940,838).

Production of Cells Comprising a First and/or Second Recombinant Polypeptides, Multimeric-protein-complexes, Heteromultimeric-protein-complexes, Multimeric-fusion-proteins, Heteromultimeric-fusion-proteins, Immunoglobulins, Immunoglobulin-polypeptide-chains, Redox-fusion-polypeptides, and/or a First and/or Second Thioredoxin-related Protein and Oil-body-targeting-proteins In accordance with the present invention, the recombinant expression vectors are introduced into the cell that is selected and the selected cells are grown to produce the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, a first and/or second thioredoxin-related protein; and the oil-body-targeting-protein either directly or in a progeny cell.

Methodologies to introduce recombinant expression vectors into a cell also referred to herein as "transformation" are well known to the art and vary depending on the cell type that is selected. General techniques to transfer the recombinant expression vectors into the cell include electroporation; chemically mediated techniques, for example CaCl2 mediated nucleic acid uptake; particle bombardment (biolistics); the use of naturally infective nucleic acid sequences for example virally derived nucleic acid sequences or when plant cells are used *Agrobacterium* or *Rhizobium* derived nucleic acid sequences; PEG mediated nucleic acid uptake, microinjection, and the use of silicone carbide whiskers (Kaeppler et al. (1990) Plant Cell Rep. 9:415418) all of which may be used herein.

Introduction of the recombinant expression vector into the cell may result in integration of its whole or partial uptake into host cell genome including the chromosomal DNA or the plastid genome. Alternatively the recombinant expression vector may not be integrated into the genome and replicate independently of the host cell's genomic DNA. Genomic integration of the nucleic acid sequence is typically used as it will allow for stable inheritance of the introduced nucleic acid sequences by subsequent generations of cells and the creation of cell, plant or animal lines.

Particular embodiments involve the use of plant cells. Particular plant cells used herein include cells obtainable from Brazil nut (*Betholletia excelsa*); castor (*Riccinus communis*); coconut (*Cocus nucifera*); coriander (*Coriandrum sativum*); cotton (*Gossypium* spp.); groundnut (*Arachis hypogaea*); jojoba (*Simmondsia chinensis*); linseed/flax (*Linum usitatissimum*); maize (*Zea mays*); mustard (*Brassica* spp. and *Sinapis alba*); oil palm (*Elaeis guineeis*); olive (*Olea europaea*); rapeseed (*Brassica* spp.); safflower (*Carthamus tinctorius*); soybean (*Glycine max*); squash (*Cucurbita maxima*); barley (*Hordeum vulgare*); wheat (*Traeticum aestivum*) and sunflower (*Helianthus annuus*).

Transformation methodologies for dicotelydenous plant species are well known. Generally *Agrobacterium* mediated transformation is utilized because of its high efficiency as well as the general susceptibility by many, if not all dicotelydenous plant species. *Agrobacterium* transformation generally involves the transfer of a binary vector (e.g. pBIN19) comprising the DNA of interest to an appropriate *Agrobacterium* strain (e.g. CIB542) by for example tri-parental mating with an *E. coli* strain carrying the recombinant binary vector and an *E. coli* strain carrying a helper plasmid capable of mobilization of the binary vector to the target *Agrobacterium* strain, or by DNA transformation of the *Agrobacterium* strain (Hofgen et al. Nucl. Acids. Res. (1988) 16: 9877. Other transformation methodologies that may be used to transform dicotelydenous plant species include biolistics (Sanford (1988) Trends in Biotechn. 6: 299–302); electroporation (Fromm et al. (1985) Proc. Natl. Acad. Sci. USA 82: 5824–5828); PEG mediated DNA uptake (Potrykus et al. (1985) Mol. Gen. Genetics 199: 169–177); microinjection (Reich et al. Bio/Techn. (1986) 4: 1001–1004) and silicone carbide whiskers (Kaeppler et al. (1990) Plant Cell Rep. 9: 415–418). The exact transformation methodologies typically vary somewhat depending on the plant species that is used.

In a particular embodiment the oil bodies are obtained from safflower and the recombinant proteins are expressed in safflower. Safflower transformation has been described by Baker and Dyer (Plant Cell Rep. (1996) 16: 106–110).

Monocotelydenous plant species may now also be transformed using a variety of methodologies including particle bombardment (Christou et al. (1991) Biotechn. 9: 957–962; Weeks et al. Plant Physiol. (1993) 102: 1077–1084; Gordon-Kamm et al. Plant Cell (1990) 2: 603–618) PEG mediated DNA uptake (EP 0 292 435; 0 392 225) or *Agrobacterium*-mediated transformation (Goto-Fumiyuki et al (1999) Nature-Biotech. 17 (3):282–286).

Plastid transformation is described in U.S. Pat. Nos. 5,451,513; 5,545,817 and 5,545,818; and PCT Patent Applications 95/16783; 98/11235 and 00/39313) Basic chloroplast transformation involves the introduction of cloned plastid DNA flanking a selectable marker together with the nucleic acid sequence of interest into a suitable target tissue using for example biolistics or protoplast transformation. Selectable markers that may be used include for example the bacterial aadA gene (Svab et al. (1993) Proc. NatI. Acad. Sci. USA 90: 913–917). Plastid promoters that may be used include for example the tobacco clpP gene promoter (PCT Patent Application 97/06250).

In another embodiment, the invention chimeric nucleic acid constructs provided herein are directly transformed into the plastid genome. Plastid transformation technology is described extensively in U.S. Pat. Nos. 5,451,513, 5,545,817, 5,545,818 and 5,576,198; in PCT application nos. WO 95/16783 and WO 97/32977; and in McBride et. al., *Proc Natl Acad Sci USA* 91: 7301–7305 (1994), the entire disclosures of all of which are hereby incorporated by reference. In one embodiment, plastid transformation is achieved via biolistics, first carried out in the unicellular green alga *Chlamydomonas* reinhardtii (Boynton et al. (1988) *Science* 240:1534–1537)) and then extended to *Nicotiana tabacum* (Svab et al. (1990) *Proc Natl Acad Sci USA* 87:8526–8530), combined with selection for cis-acting antibiotic resistance loci (spectinomycin or streptomycin resistance) or complementation of non-photosynthetic mutant phenotypes.

In another embodiment, tobacco plastid transformation is carried out by particle bombardment of leaf or callus tissue, or polyethylene glycol (PEG)-mediated uptake of plasmid DNA by protoplasts, using cloned plastid DNA flanking a selectable antibiotic resistance marker. For example, 1 to 1.5 kb flanking regions, termed targeting sequences, facilitate homologous recombination with the plastid genome and allow the replacement or modification of specific regions of the 156 kb tobacco plastid genome. In one embodiment, point mutations in the plastid 16S rDNA and rps12 genes conferring resistance to spectinomycin and/or streptomycin can be utilized as selectable markers for transformation (Svab et al. (1990) *Proc Natl Acad Sci USA* 87:8526–8530; Staub et al. (1992) *Plant Cell* 4:39–45, the entire disclosures of which are hereby incorporated by reference), resulting in stable homoplasmic transformants at a frequency of approximately one per 100 bombardments of target leaves. The presence of cloning sites between these markers allows creation of a plastid targeting vector for introduction of foreign genes (Staub et al. (1993) *EMBO J* 12:601–606, the entire disclosure of which is hereby incorporated by reference). In another embodiment, substantial increases in transformation frequency can be obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab et al. (1993) *Proc Natl Acad Sci USA* 90: 913–917, the entire disclosure of which is hereby incorporated by reference). This marker has also been used successfully for high-frequency transformation of the plastid genome of the green alga *Chlamydomonas reinhardtii* (Goldschmidt-Clermont, M. (1991) *Nucl Acids Res* 19, 4083–4089, the entire disclosure of which is hereby incorporated by reference). In other embodiments, plastid transformation of protoplasts from tobacco and the moss *Physcomitrella* can be attained using PEG-mediated DNA uptake (O'Neill et al. (1993) *Plant J* 3:729–738; Koop et al. (1996) *Planta* 199:193–201, the entire disclosures of which are hereby incorporated by reference).

Both particle bombardment and protoplast transformation are also contemplated for use herein. Plastid transformation of oilseed plants has been successfully carried out in the genera *Arabidopsis* and *Brassica* (Sikdar et al. (1998) *Plant Cell Rep* 18:20–24; PCT Application WO 00/39313, the entire disclosures of which are hereby incorporated by reference).

A chimeric nucleic sequence construct is inserted into a plastid expression cassette including a promoter capable of expressing the construct in plant plastids. A particular promoter capable of expression in a plant plastid is, for example, a promoter isolated from the 5' flanking region upstream of the coding region of a plastid gene, which may come from the same or a different species, and the native product of which is typically found in a majority of plastid types including those present in non-green tissues. Gene expression in plastids differs from nuclear gene expression and is related to gene expression in prokaryotes (Stern et al. (1997) *Trends in Plant Sci* 2:308–315, the entire disclosure of which is hereby incorporated by reference).

Plastid promoters generally contain the −35 and −10 elements typical of prokaryotic promoters, and some plastid promoters called PEP (plastid-encoded RNA polymerase) promoters are recognized by an *E. coli*-like RNA polymerase mostly encoded in the plastid genome, while other plastid promoters called NEP promoters are recognized by a nuclear-encoded RNA polymerase. Both types of plastid promoters are suitable for use herein. Examples of plastid promoters include promoters of clpP genes such as the tobacco clpP gene promoter (WO 97/06250, the entire disclosure of which is hereby incorporated by reference) and the *Arabidopsis* clpP gene promoter (U.S. Application No. 09/038,878, the entire disclosure of which is hereby incorporated by reference). Another promoter capable of driving expression of a chimeric nucleic acid construct in plant plastids comes from the regulatory region of the plastid 16S ribosomal RNA operon (Harris et al., (1994) *Microbiol Rev* 58:700–754; Shinozaki et al. (1986) *EMBO J* 5:2043–2049, the entire disclosures of both of which are hereby incorporated by reference). Other examples of promoters capable of driving expression of a nucleic acid construct in plant plastids include a psbA promoter or am rbcL promoter. A plastid expression cassette preferably further includes a plastid gene 3' untranslated sequence (3' UTR) operatively linked to a chimeric nucleic acid construct of the present invention. The role of untranslated sequences is preferably to direct the 3' processing of the transcribed RNA rather than termination of transcription. An exemplary 3' UTR is a plastid rps16 gene 3' untranslated sequence, or the *Arabidopsis* plastid psbA gene 3' untranslated sequence. In a further embodiment, a plastid expression cassette includes a poly-G tract instead of a 3' untranslated sequence. A plastid expression cassette also preferably further includes a 5' untranslated sequence (5' UTR) functional in plant plastids, operatively linked to a chimeric nucleic acid construct provided herein.

A plastid expression cassette is contained in a plastid transformation vector, which preferably further includes flanking regions for integration into the plastid genome by homologous recombination. The plastid transformation vector may optionally include at least one plastid origin of replication. The present invention also encompasses a plant plastid transformed with such a plastid transformation vector, wherein the chimeric nucleic acid construct is expressible in the plant plastid. Also encompassed herein is a plant or plant cell, including the progeny thereof, including this plant plastid. In a particular embodiment, the plant or plant cell, including the progeny thereof, is homoplasmic for transgenic plastids.

Other promoters capable of driving expression of a chimeric nucleic acid construct in plant plastids include transactivator-regulated promoters, preferably heterologous with respect to the plant or to the subcellular organelle or component of the plant cell in which expression is effected. In these cases, the DNA molecule encoding the transactivator is inserted into an appropriate nuclear expression cassette which is transformed into the plant nuclear DNA. The transactivator is targeted to plastids using a plastid transit peptide. The transactivator and the transactivator-driven DNA molecule are brought together either by crossing a selected plastid-transformed line with and a transgenic line containing a DNA molecule encoding the transactivator supplemented with a plastid-targeting sequence and operably linked to a nuclear promoter, or by directly transforming a plastid transformation vector containing the desired DNA molecule into a transgenic line containing a chimeric nucleic acid construct encoding the transactivator supplemented with a plastid-targeting sequence operably linked to a nuclear promoter. If the nuclear promoter is an inducible promoter, in particular a chemically inducible embodiment, expression of the chimeric nucleic acid construct in the plastids of plants is activated by foliar application of a chemical inducer. Such an inducible transactivator-mediated plastid expression system is preferably tightly regulatable, with no detectable expression prior to induction and exceptionally high expression and accumulation of protein following induction.

A particular transactivator is, for example, viral RNA polymerase. Particular promoters of this type are promoters recognized by a single sub-unit RNA polymerase, such as the T7 gene 10 promoter, which is recognized by the bacteriophage T7 DNA-dependent RNA polymerase. The gene encoding the T7 polymerase is preferably transformed into the nuclear genome and the T7 polymerase is targeted to the plastids using a plastid transit peptide. Promoters suitable for nuclear expression of a gene, for example a gene encoding a viral RNA polymerase such as the T7 polymerase, are described above and elsewhere in this application. Expression of chimeric nucleic acid constructs in plastids can be constitutive or can be inducible, and such plastid expression can be also organ- or tissue-specific. Examples of various expression systems are extensively described in WO 98/11235, the entire disclosure of which is hereby incorporated by reference. Thus, in one aspect, the present invention utilizes coupled expression in the nuclear genome of a chloroplast-targeted phage T7 RNA polymerase under the control of the chemically inducible PR-1a promoter, for example of the PR-1 promoter of tobacco, operably linked with a chloroplast reporter transgene regulated by T7 gene 10 promoter/terminator sequences, for example as described in as in U.S. Pat. No. 5,614,395 the entire disclosure of which is hereby incorporated by reference. In another embodiment, when plastid transformants homoplasmic for the maternally inherited TR or NTR genes are pollinated by lines expressing the T7 polymerase in the nucleus, F1 plants are obtained that carry both transgene constructs but do not express them until synthesis of large amounts of enzymatically active protein in the plastids is triggered by foliar application of the PR-1a inducer compound benzo(1,2,3)thiadiazole-7-carbothioic acid S-methyl ester (BTH).

In a particular embodiment, two or more genes, for example TR and NTR genes, are transcribed from the plastid genome from a single promoter in an operon-like polycistronic gene. In one embodiment, the operon-like polycistronic gene includes an intervening DNA sequence between two genes in the operon-like polycistronic gene. In a particular embodiment, the intervening DNA sequence is not present in the plastid genome to avoid homologous recombination with plastid sequences. In another embodiment, the DNA sequence is derived from the 5' untranslated (UTR) region of a non-eukaryotic gene, preferably from a viral 5'UTR, preferably from a 5'UTR derived from a bacterial phage, such as a T7, T3 or SP6 phage. In one embodiment, a portion of the DNA sequence may be modified to prevent the formation of RNA secondary structures in an RNA transcript of the operon-like polycistronic gene, for example between the DNA sequence and the RBS of the downstream gene. Such secondary structures may inhibit or repress the expression of the downstream gene, particularly the initiation of translation. Such RNA secondary structures are predicted by determining their melting temperatures using computer models and programs such a the "mfold" program version 3 (available from Zuker and Turner, Washington University School of Medicine, St-Louis, Mo.) and other methods known to one skilled in the art.

The presence of the intervening DNA sequence in the operon-like polycistronic gene increases the accessibility of the RBS of the downstream gene, thus resulting in higher rates of expression. Such strategy is applicable to any two or more genes to be transcribed from the plastid genome from a single promoter in an operon-like chimeric heteromultimeric gene.

Following transformation the cells are grown, typically in a selective medium allowing the identification of transformants. Cells may be harvested in accordance with methodologies known to the art. In order to associate the oil bodies with the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, and a first and/or second thioredoxin-related protein, the integrity of cells may be disrupted using any physical, chemical or biological methodology capable of disrupting the cells' integrity. These methodologies are generally cell-type dependent and known to the skilled artisan. Where plants are employed they may be regenerated into mature plants using plant tissue culture techniques generally known to the skilled artisan. Seeds may be harvested from mature transformed plants and used to propagate the plant line. Plants may also be crossed and in this manner, contemplated herein is the breeding of cells lines and transgenic plants that vary in genetic background. It is also possible to cross a plant line comprising the first recombinant polypeptide with a plant line comprising the second recombinant polypeptide. Accordingly, also provided herein are methods of producing in a plant a recombinant multimeric-protein-complex, said method comprising:

(a) preparing a first plant comprising cells, said cells comprising oil bodies and a first recombinant polypeptide, such as a redox protein (e.g., a thioredoxin-related protein, and the like) or an immunoglobulin-polypeptide-chain, wherein said first recombinant polypeptide is capable of associating with said oil bodies through an oil-body-targeting-protein;

(b) preparing a second plant comprising cells, said cells comprising oil bodies and a second recombinant polypeptide, such as a second redox protein (e.g., a thioredoxin-related protein, and the like) or a second immunoglobulin-polypeptide-chain; and (c) sexually crossing said first plant with said second plant to produce a progeny plant comprising cells, said cells comprising oil bodies, wherein said oil bodies are capable of associating with said first recombinant polypeptide, and said first recombinant recombinant polypeptide is capable of associating with said second recombinant polypeptide to form said recombinant multimeric-protein-complex.

The second recombinant polypeptide may also associate with the oil bodies. Accordingly, also provided herein are methods of producing in a plant a recombinant multimeric-protein-complex, said method comprising:

(a) preparing a first plant comprising cells, said cells comprising oil bodies and a first recombinant polypeptide, such as a redox (or thioredoxin-related) protein or immunoglobulin-polypeptide-chain, wherein said first recombinant polypeptide is capable of associating with said oil bodies through an oil-body-targeting-protein;

(b) preparing a second plant comprising cells, said cells comprising oil bodies and a second recombinant polypeptide, such as a second redox (thioredoxin-related) protein or a second immunoglobulin-polypeptide-chain, wherein said second recombinant polypeptide is capable of associating with said oil bodies through an oil body targeting protein; and (c) sexually crossing said first plant with said second plant to produce a progeny plant comprising cells, said cells comprising oil bodies, wherein said oil bodies are capable of associating with said first recombinant polypeptide, and said first recombinant recombinant polypeptide is capable of associating with said second recombinant polypeptide to form said recombinant multimeric-protein-complex.

The first and second recombinant polypeptide may also be prepared in a first plant line. A second plant line comprising the oil body targeting protein capable of associating with the first recombinant polypeptide may subsequently be crossed with the first plant line. Oil bodies comprising the multimeric-protein-complex may be isolated from progeny plants. Accordingly, also provided herein are methods of producing in a plant a recombinant multimeric-protein-complex, said method comprising:

(a) preparing a first plant comprising cells, said cells comprising oil bodies and a first and second recombinant polypeptide wherein said first recombinant polypeptide is capable of associating with said oil bodies through an oil-body-targeting-protein;

(b) preparing a second plant comprising cells, said cells comprising oil bodies and an oil-body-targeting-protein that is capable of associating with said first recombinant polypeptide; and (c) sexually crossing said first plant with said second plant to produce a progeny plant comprising cells, said cells comprising oil bodies, wherein said oil bodies are capable of associating with said first recombinant polypeptide through said oil-body-targeting-protein, and said first recombinant recombinant polypeptide is capable of associating with said second recombinant polypeptide to form said recombinant multimeric-protein-complex. The oil bodies can be isolated from the progeny plant comprising said multimeric-protein-complex. The oil-body-targeting-protein can be selected from an oil-body-protein or an immunoglobulin, wherein the oil-body-protein can be an oleosin or caleosin. The first and second recombinant polypeptide can form a multimeric-protein-complex, such as a heteromultimeric-protein-complex, wherein the heteromultimeric-protein-complex can be an enzymatically active redox complex or an immunoglobulinln another embodiment, the first recombinant polypeptide can be an immunoglobulin-polypeptide-chain. For example, the first recombinant polypeptide can be an immunoglobulin light chain, or an immunologically active portion thereof, and the second recombinant polypeptide can be an immunoglobulin heavy chain, or an immunologically active portion thereof. In this embodiment, the oil-body-targeting-protein can comprise protein A, protein L or protein G. The plant can be a safflower plant.

Isolation of Oil Bodies

The oil bodies provided herein may be obtained from any cell containing oil bodies, including any animal cell; plant cell; fungal cell; for example a yeast cell, algae cell; or bacterial cell. Any process suitable for the isolation oil bodies from cells may be used herein. Processes for the isolation of oil bodies from plant seed cells have been described in U.S. Pat. Nos. (6,146,645 and 6,183,762) and the isolation of oil bodies from yeast cells has been described by Ting et al. (1997) J. Biol. Chem. 272: 3699–3706).

In certain embodiments, the oil bodies are obtained from a plant cell such as for example a pollen cell; a fruit cell; a spore cell; a nut cell; mesocarp cell; for example the mesocarp cells obtainable from olive (*Olea europaea*) or avocado (*Persea americana*); or a seed cell. In particular embodiments the oil bodies are obtained from a plant seed cell. The seeds can be obtained from a transgenic plant according to the present invention. In particular embodiments, a seed of a transgenic plant according to the present invention contains the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or first and/or second thioredoxin-related proteins in a concentration of at least about 0.5% of total cellular seed protein. In further embodiments, a seed of a transgenic plant provided herein contains a recombinant polypeptide or multimeric-protein-complex in a concentration of at least about 0.5%, 0.6%, 0.7%, 0.8%, 0.9%, 1.0%, 1.25%, 1.5%, 1.75%, 2.0%, 2.25%, 2.5%, 3%, 4%, 5%, 6%, 7%, 8%, 9%, 10% or more, of total cellular seed protein. The upper limits of the recombinant polypeptide or multimeric-protein-complex concentration can be up to about 8%, 9%, 10%, 11%, 12%, 13%, 14%, 15%. Thus, the ranges at least about 0.5% up to about 15%; at least about 1.0% up to about 10%; and at least about 5% up to about 8% are among the various ranges contemplated herein.

Among the plant seeds useful in this regard are plant seeds obtainable from the group of plant species consisting of Brazil nut (*Betholletia excelsa*); castor (*Riccinus communes*); coconut (*Cocus nucifera*); coriander (*Coriandrum sativum*); cotton (*Gossypium* spp.); groundnut (*Arachis hypogaea*); jojoba (*Simmondsia chinensis*); linseed/flax (*Linum usitatissimum*); maize (*Zea mays*); mustard (*Brassica* spp. and *Sinapis alba*); oil palm (*Elaeis guineeis*); olive (*Olea europaea*); rapeseed (*Brassica* spp.); safflower (*Carthamus tinctorius*); soybean (*Glycine max*); squash (*Cucurbita maxima*); sunflower (*Helianthus annuus*); barley (*Hordeum vulgare*); wheat (*Traeticum aestivum*) and mixtures thereof. In a particular embodiment, oil bodies are obtainable from the seeds obtainable from safflower (*Carthamus tinctorius*).

In order to prepare oil bodies from plant seeds, plants are grown and allowed to set seed in accordance with common agricultural practices. Thus, the present invention also provides seeds comprising oil bodies, wherein said oil bodies further comprise invention multimeric-protein-complexes described herein. Upon harvesting the seed and, if necessary the removal of large insoluble materials such as stones or seed hulls, by for example sieving or rinsing, any process suitable for the isolation of oil bodies from seeds may be used herein. A typical process involves grinding of the seeds followed by an aqueous extraction process.

Seed grinding may be accomplished by any comminuting process resulting in a substantial disruption of the seed cell membrane and cell walls without compromising the structural integrity of the oil bodies present in the seed cell. Suitable grinding processes in this regard include mechanical pressing and milling of the seed. Wet milling processes such as described for cotton (Lawhon et al. (1977) J. Am. Oil Chem. Soc. 63: 533–534) and soybean (U.S. Pat. No. 3,971,856; Carter et al. (1974) J. Am. Oil Chem. Soc. 51: 137–141) are particularly useful in this regard. Suitable milling equipment capable of industrial scale seed milling include colloid mills, disc mills, pin mills, orbital mills, IKA mills and industrial scale homogenizers. The selection of the milling equipment will depend on the seed, which is selected, as well as the throughput requirement.

Solid contaminants such as seed hulls, fibrous materials, undissolved carbohydrates, proteins and other insoluble contaminants are subsequently preferably removed from the ground seed fraction using size exclusion based methodologies such as filtering or gravitational based methods such as a centrifugation based separation process. Centrifugation may be accomplished using for example a decantation centrifuge such as a HASCO 200 2-phase decantation centrifuge or an NX310B (Alpha Laval). Operating conditions are selected such that a substantial portion of the insoluble contaminants and sediments and may be separated from the soluble fraction.

Following the removal of insolubles the oil body fraction may be separated from the aqueous fraction. Gravitational based methods as well as size exclusion based technologies may be used. Gravitational based methods that may be used include centrifugation using for example a tubular bowl centrifuge such as a Sharples AS-16 or AS-46 (Alpha Laval), a disc stack centrifuge or a hydrocyclone, or separation of the phases under natural gravitation. Size exclusion methodologies that may be used include membrane ultra filtration and crossflow microfiltration.

Separation of solids and separation of the oil body phase from the aqueous phase may also be carried out concomitantly using gravity based separation methods or size exclusion based methods.

The oil body preparations obtained at this stage in the process are generally relatively crude and depending on the application of the oil bodies, it may be desirable to remove additional contaminants. Any process capable of removing additional seed contaminants may be used in this regard. Conveniently the removal of these contaminants from the oil body preparation may be accomplished by resuspending the oil body preparation in an aqueous phase and re-centrifuging the resuspended fraction, a process referred to herein as "washing the oil bodies". The washing conditions selected may vary depending on the desired purity of the oil body fractions. For example where oil bodies are used in pharmaceutical compositions, generally a higher degree of purity may be desirable than when the oil bodies are used in food preparations. The oil bodies may be washed one or more times depending on the desired purity and the ionic strength, pH and temperature may all be varied. Analytical techniques may be used to monitor the removal of contaminants. For example SDS gel electrophoresis may be employed to monitor the removal of seed proteins.

The entire oil body isolation process may be performed in a batch wise fashion or continuous flow. In a particular embodiment, industrial scale continuous flow processes are utilized.

Through the application of these and similar techniques the skilled artisan is able to obtain oil bodies from any cell comprising oil bodies. The skilled artisan will recognize that generally the process will vary somewhat depending on the cell type that is selected. However, such variations may be made without departing from the scope and spirit of the present invention.

Association of the First and/or Second Recombinant Polypeptides, Multimeric-protein-complexes, Heteromultimeric-protein-complexes, Multimeric-fusion-proteins, Heteromultimeric-fusion-proteins, Immunoglobulins, Immunoglobulin-polypeptide-chains, Redox-fusion-polypeptides, the First and/or Second Thioredoxin-related Proteins with Oil Bodies In accordance with the present invention, the oil bodies are associated with either the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, the first and/or second thioredoxin-related proteins through association with an oil-body-targeting-protein capable of association with these multimeric-protein-complexes and the oil bodies. As used herein the phrase "associating the oil bodies with the multimeric-protein-complex" means that the oil bodies are brought in proximity of the multimeric-protein-complexes in a manner that allows the association of the oil bodies with either the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins. The association of the oil bodies with the multimeric-protein-complexes is accomplished by association of the oil-body-targeting-protein with both the oil body and with the multimeric-protein-complex. In particular embodiments, the cells expressing the multimeric-protein-complex associate with the oil bodies that are obtainable from these same cells, which permits the convenient production and isolation of the multimeric-protein-complex, including the first and/or second recombinant polypeptides, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins, in an oil body-comprising host cell system. Accordingly, in one embodiment, the association of the oil body with the multimeric-protein-complex is accomplished intracellularly during the growth of the cell. For example, a redox fusion polypeptide may be fused to an oil-body-protein and the chimeric protein may be expressed in oil body-containing plant seeds. Isolation of the oil bodies from the seeds in this case results in isolation of oil bodies comprising either the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins. In another embodiment, in which the multimeric-protein-complex associates with oil bodies obtainable from the same cells in which the complex is produced, the association of the oil bodies with the multimeric-protein-complex is accomplished upon disrupting the cell's integrity, for example in embodiments of the present invention where plant seeds are used upon grinding these plant seeds.

For example, the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins may be expressed in such a manner that it is targeted to the endomembrane system of the seed cells. Oil bodies present in the same seed cells comprising an oil-body-targeting-protein capable of association with these multimeric-protein-complexes, for example an oleosin linked to a single chain antibody capable of association with a recombinant polypeptide or multimeric-protein-complex, may then associate with the recombinant polypeptide or multimeric-protein-complex upon grinding of the seed.

In accordance with this embodiment, plant seed cells comprising a light and heavy chain of an immunoglobulin targeted to the plant apoplast can be prepared. These particular seed cells are prepared to further comprise oil bodies associated with an oil-body-targeting-protein capable of association with the immunoglobulin, such as for example, an oleosin-protein A fusion protein, and the like. Upon grinding of the seed, the oil bodies comprising protein A associate with the immunoglobulin through binding.

In yet another embodiment, the oil bodies used to associate with the multimeric-protein-complex are obtained from a cellular source different from the cell comprising the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins, such as from a separate plant line. For example, oil bodies associated with protein A may be prepared from one plant line. These oil bodies may then be mixed with ground seeds comprising an apoplastically expressed light and heavy chain constituting an immunoglobulin. Alternatively, a plant line comprising oil bodies associated with protein A may be crossed with a plant line comprising an immunoglobulin.

The first recombinant polypeptide, second recombinant polypeptide and oil-body-targeting-protein may also be prepared in separate cellular compartments. Association of the first polypeptide, second polypeptide, and oil body then may occur upon disruption of the cell's integrity. For example, various mechanisms for targeting gene products are known to exist in plants, and the sequences controlling the functioning of these mechanisms have been characterized in some detail. For example, the targeting of gene products to the chloroplast is controlled by a transit sequence found at the amino terminal end of various proteins which is cleaved during chloroplast import to yield the mature protein (Comai et al. (1988) *J Biol Chem* 263: 15104–15109). Other gene products are localized to other organelles such as the mitochondrion and the peroxisome (Unger et al. (1989) *Plant Mol Biol* 13:411–418). The cDNAs encoding these products can be manipulated to target heterologous gene products to these organelles. In addition, sequences have been characterized which cause the targeting of gene products to other cell compartments. Amino terminal sequences are responsible for targeting to the ER, the apoplast, and extracellular secretion from aleurone cells (Koehler & Ho (1990) *Plant Cell* 2:769–783). Additionally, amino terminal sequences in conjunction with carboxy terminal sequences are responsible for vacuolar targeting of gene products (Shinshi et al., (1990) *Plant Mol Biol* 14:357–368). By the fusion of the appropriate targeting sequences described above to transgene sequences of interest it is possible to direct the transgene product to the desired organelle or cell compartment.

As hereinbefore mentioned, the redox protein obtained using the methods provided herein is enzymatically active while associated with the oil body. Preferably the redox protein is at least 5 times more active when produced as a redox fusion polypeptide with a second redox protein relative to its production in association with an oil body as a non-fusion polypeptide (i.e. without the second redox protein). More preferably the redox protein is at least 10 times more active when produced as a redox fusion polypeptide.

The activity of the redox fusion polypeptide may be determined in accordance with methodologies generally known to the art (see for example: Johnson et al (1984) J. of Bact. Vol. 158 3:1061–1069) and may be optimized by for example the addition of detergents, including ionic and non-ionic detergents.

Formulation of Oil Bodies

In accordance with a particular embodiment, the oil bodies comprising the first and/or second recombinant polypeptides, multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides, or the first and/or second thioredoxin-related proteins, are preferably formulated into an emulsion. The emulsion is preferably used in the preparation of a pharmaceutical composition, personal care or a food product. In emulsified form, the oil body offers certain desirable properties, such as for example excellent compatibility with the human skin.

It particular embodiments, the oil body formulation is stabilized so that a final product may be obtained which may be stored and preserved for longer periods of time. As used herein, the term "stabilized oil body preparation" refers to an oil body preparation that is prepared so that the formulation does not undergo undesirable physical or chemical alterations when the oil body preparation is stored. The stabilization requirements may vary depending on the final product. For example personal care products are preferably stable for at least one year at room temperature while additionally being able to withstand short temperature fluctuations. Pharmaceutical formulations may in some cases be less stable as they may be stored at lower temperatures thereby preventing the occurrence of undesirable reactions.

In general, stabilization techniques that may be used herein include any and all methods for the preservation of biological material including the addition of chemical agents, temperature modulation based methodologies, radiation-based technologies and combinations thereof. In particular embodiments small amounts of stabilizing chemical agents are mixed with the oil body formulation to achieve stabilization. These chemical agents include inter alia preservatives, antioxidants, acids, salts, bases, viscosity modifying agents, emulsifiers, gelling agents and mixtures thereof and may all be used to stabilize the oil body preparation. In view of the presence of the redox fusion polypeptide or immunoglobulin the stabilizing agent is generally selected to be compatible with and resulting in good enzymatic function of the redox fusion polypeptide or immunoglobulin function.

Diagnostic parameters to assess the stability of the oil body preparation may be as desired and include all parameters indicative of undesirable qualitative or quantitative changes with respect to chemical or physical stability. Typical parameters to assess the oil body preparation over time include color, odor, viscosity, texture, pH and microbial growth, and enzymatic activity.

In particular embodiments, the oil body formulation is stabilized prior to the addition of further ingredients that may be used to prepare the final product. However, in other embodiments, it is nevertheless possible to formulate the final formulation using non-stabilized oil bodies and stabilize the final formulation. The final preparations may be obtained using one or more additional ingredients and any formulation process suitable for the preparation of a formulation comprising oil bodies. Ingredients and processes employed will generally vary depending on the desired use of the final product, will be art recognized and may be as desired. Ingredients and processes that may be used herein include those described in US Patents (U.S. Pat. Nos. 6,146,645 and 6,183,762) which are incorporated by reference herein.

In particular embodiments, the redox fusion polypeptide comprises a thioredoxin and a thioredoxin-reductase. Accordingly, provided herein are oil bodies comprising a thioredoxin/thioredoxin-reductase fusion polypeptide. Also provided herein is a formulation containing oil bodies comprising a thioredoxin/thioredoxin-reductase fusion capable of treating or protecting a target against oxidative stress. The stress of the target is treated or prevented by contacting the target with the formulation. The target may be any substance susceptible to oxidative stress, including any molecule, molecular complex, cell, tissue or organ.

In another embodiment, provided herein is a formulation containing oil bodies comprising a thioredoxin/thioredoxin-reductase fusion capable of chemically reducing a target. Contacting the target with the formulation reduces the target. The target may be any substance susceptible to reduction, including any molecule or molecular complex. Particularly susceptible targets in this regard are the disulfide bonds present in proteins.

The oil bodies comprising thioredoxin/thioredoxin-reductase may be used to prepare formulations used to reduce the allergenicity of food or increase the digestibility of food. Preferably, the method of reducing the food allergenicity is practiced by mixing the thioredoxin/thioredoxin-reductase comprising oil bodies with food or food ingredients selected from a variety of sources including for example wheat flour, wheat dough, milk, cheese, soya, yogurt and ice cream. The thioredoxin/thioredoxin-reductase comprising oil bodies may also be used to increase the digestibility of milk as well as other disulfide containing proteins (Jiao, J. et al. (1992) J. Agric. Food Chem 40: 2333–2336). Further food applications include the use of the oil thioredoxin/thioredoxin-reductase comprising oil bodies as a food additive to enhance dough strength and bread quality properties (Wong et al., (1993) J. Cereal Chem. 70: 113–114; Kobrehel et al. (1994) Gluten Proteins: Association of Cereal Research; Detmold, Germany).

Also provided herein are pharmaceutical compositions comprising, in a pharmaceutically active carrier: oil bodies comprising a thioredoxin/thioredoxin-reductase; oil bodies comprising multimeric-protein-complexes, such as heteromultimeric-protein-complexes; isolated thioredoxin/thioredoxin-reductase fusion proteins; or isolated multimeric-protein-complexes. These pharmaceutical compositions may be used for the treatment of reperfusion injury (Aota et al. (1996) J. Cardiov. Pharmacol. (1996) 27: 727–732), cataracts (U.S. Pat. No. 4,771,036), chronic obstructive pulmonary disease (COPD) (MacNee et al. (1999) Am. J. Respir. Crit. Care Med. 160:S58-S65), diabetes (Hotta et al. J. Exp. Med. 188: 1445–1451), envenomation (PCT Patent Application 99/20122; U.S. Pat. No. 5,792,506), bronchiopulmonary disease (MacNee (2000) Chest 117:3035–317S); malignancies (PCT Patent Application 91/04320) and the alleviation of the allergenic potential of airborne, for example pollen-derived, and contact allergens (PCT Patent Application 00/44781). Other diseases or conditions that may be treated with the pharmaceutical compositions provided herein include: psoriasis, wound healing, sepsis, GI bleeding, intestinal bowel disease (IBD), ulcers, transplantation, GERD (gastro esophageal reflux disease).

The pharmaceutical compositions provided herein are preferably formulated for single dosage administration. The concentrations of the compounds in the formulations are effective for delivery of an amount, upon administration, that is effective for the intended treatment. Typically, the compositions are formulated for single dosage administration. To formulate a composition, the weight fraction of a compound or mixture thereof is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems, such as the assays provided herein.

The concentration of active compound in the drug composition will depend on absorption, inactivation and excretion rates of the active compound, the physicochemical characteristics of the compound, the dosage schedule, and amount administered as well as other factors known to those of skill in the art.

Typically a therapeutically effective dosage is contemplated. The amounts administered may be on the order of 0.001 to 1 mg/ml, preferably about 0.005–0.05 mg/ml, more preferably about 0.01 mg/ml, of blood volume. Pharmaceutical dosage unit forms are prepared to provide from about 1 mg to about 1000 mg and preferably from about 10 to about 500 mg, more preferably about 25–75 mg of the essential active ingredient or a combination of essential ingredients per dosage unit form. The precise dosage can be empirically determined.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or use of the claimed compositions and combinations containing them.

Preferred pharmaceutically acceptable derivatives include acids, salts, esters, hydrates, solvates and prodrug forms. The derivative is typically selected such that its pharmacokinetic properties are superior to the corresponding neutral compound.

Thus, effective concentrations or amounts of one or more of the compounds provided herein or pharmaceutically acceptable derivatives thereof are mixed with a suitable pharmaceutical carrier or vehicle for systemic, topical or local administration to form pharmaceutical compositions. Compounds are included in an amount effective for ameliorating or treating the disorder for which treatment is contemplated. The concentration of active compound in the composition will depend on absorption, inactivation, excretion rates of the active compound, the dosage schedule, amount administered, particular formulation as well as other factors known to those of skill in the art. Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as Tween®, or dissolution in aqueous sodium bicarbonate. Derivatives of the compounds, such as prodrugs of the compounds may also be used in formulating effective pharmaceutical compositions. For ophthalmic indications, the compositions are formulated in an ophthalmically acceptable carrier. For the ophthalmic uses herein, local administration, either by topical administration or by injection is preferred. Time release formulations are also desirable. Typically, the compositions are formulated for single dosage administration, so that a single dose administers an effective amount.

Upon mixing or addition of the compound with the vehicle, the resulting mixture may be a solution, suspension, emulsion or other composition. The form of the resulting mixture depends upon a number of factors, including the intended mode of administration and the solubility of the compound in the selected carrier or vehicle. If necessary, pharmaceutically acceptable salts or other derivatives of the compounds are prepared.

The compound is included in the pharmaceutically acceptable carrier in an amount sufficient to exert a therapeutically useful effect in the absence of undesirable side effects on the patient treated. It is understood that number and degree of side effects depends upon the condition for which the compounds are administered. For example, certain toxic and undesirable side effects are tolerated when treating life-threatening illnesses that would not be tolerated when treating disorders of lesser consequence.

The compounds can also be mixed with other active materials, that do not impair the desired action, or with materials that supplement the desired action known to those of skill in the art. The formulations of the compounds and agents for use herein include those suitable for oral, rectal, topical, inhalational, buccal (e.g., sublingual), parenteral (e.g., subcutaneous, intramuscular, intradermal, or intravenous), transdermal administration or any route. The most suitable route in any given case will depend on the nature and severity of the condition being treated and on the nature of the particular active compound which is being used. The formulations are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutically acceptable carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Methods of preparing such dosage forms are known, or will be apparent, to those skilled in this art (see, e.g., Remington's Pharmaceutical Sciences, Mack Publishing Company, Easton, Pa., 15th Edition, 1975). The composition or formulation to be administered will contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, the pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

The pharmaceutical preparation may also be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid).

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin or to the eye preferably take the form of an ointment, cream, lotion, paste, gel, spray, aerosol and oil. Carriers which may be used include vaseline, lanoline, polyethylene glycols, alcohols, and combinations of two or more thereof. The topical formulations may further advantageously contain 0.05 to 15 percent by weight of thickeners selected from among hydroxypropyl methyl cellulose, methyl cellulose, polyvinylpyrrolidone, polyvinyl alcohol, poly (alkylene glycols), poly/hydroxyalkyl, (meth)acrylates or poly(meth)

acrylamides. A topical formulation is often applied by instillation or as an ointment into the conjunctival sac. It can also be used for irrigation or lubrication of the eye, facial sinuses, and external auditory meatus. It may also be injected into the anterior eye chamber and other places. The topical formulations in the liquid state may be also present in a hydrophilic three-dimensional polymer matrix in the form of a strip, contact lens, and the like from which the active components are released.

For administration by inhalation, the compounds for use herein can be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin, for use in an inhaler or insulator may be formulated containing a powder mix of the compound and a suitable powder base such as lactose or starch.

Formulations suitable for buccal (sublingual) administration include, for example, lozenges containing the active compound in a flavored base, usually sucrose and acacia or tragacanth; and pastilles containing the compound in an inert base such as gelatin and glycerin or sucrose and acacia.

The compounds may be formulated for parenteral administration by injection, e.g., by bolus injection or continuous infusion. Formulations for injection may be presented in unit dosage form, e.g., in ampules or in multi-dose containers, with an added preservative. The compositions may be suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile pyrogen-free water or other solvents, before use.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 to 0.2 M concentration with respect to the active compound. Formulations suitable for transdermal administration may also be delivered by iontophoresis (see, e.g., Pharmaceutical Research 3 (6), 318 (1986)) and typically take the form of an optionally buffered aqueous solution of the active compound.

The pharmaceutical compositions may also be administered by controlled release means and/or delivery devices (see, e.g., in U.S. Pat. Nos. 3,536,809; 3,598,123; 3,630,200; 3,845,770; 3,847,770; 3,916,899; 4,008,719; 4,687,610; 4,769,027; 5,059,595; 5,073,543; 5,120,548; 5,354,566; 5,591,767; 5,639,476; 5,674,533 and 5,733,566).

Desirable blood levels may be maintained by a continuous infusion of the active agent as ascertained by plasma levels. It should be noted that the attending physician would know how to and when to terminate, interrupt or adjust therapy to lower dosage due to toxicity, or bone marrow, liver or kidney dysfunctions. Conversely, the attending physician would also know how to and when to adjust treatment to higher levels if the clinical response is not adequate (precluding toxic side effects).

The efficacy and/or toxicity of the pharmaceutical compositions provided herein, alone or in combination with other agents can also be assessed by the methods known in the art (See generally, O'Reilly, *Investigational New Drugs*, 15:5–13 (1997)).

The active compounds or pharmaceutically acceptable derivatives may be prepared with carriers that protect the compound against rapid elimination from the body, such as time release formulations or coatings.

Kits containing the compositions and/or the combinations with instructions for administration thereof are provided. The kit may further include a needle or syringe, preferably packaged in sterile form, for injecting the complex, and/or a packaged alcohol pad. Instructions are optionally included for administration of the active agent by a clinician or by the patient. Finally, the pharmaceutical compositions provided herein containing any of the preceding agents may be packaged as articles of manufacture containing packaging material, a compound or suitable derivative thereof provided herein, which is effective for treatment of a diseases or disorders contemplated herein, within the packaging material, and a label that indicates that the compound or a suitable derivative thereof is for treating the diseases or disorders contemplated herein. The label can optionally include the disorders for which the therapy is warranted. Also provided herein are personal care formulations containing oil bodies comprising a thioredoxin/thioredoxin-reductase fusion polypeptide or a multimeric immunoglobulin. Personal care products comprising thioredoxin and thioredoxin-reductase are disclosed in for example Japanese Patent Applications JP9012471A2, JP103743A2, and JP1129785A2. Personal care formulations that may be prepared in accordance with the present invention include formulations capable of improving the physical appearance of skin exposed to detrimental environmental stimuli resulting in oxidative stress for example oxidative stress caused by UV-generated free-radicals. The oil bodies comprising thioredoxin/thioredoxin-reductase may also be used to prepare hair care products as described in U.S. Pat. Nos. 4,935,231 and 4,973,475 (incorporated herein by reference in their entirety). The personal care formulations comprising multimeric immunoglobulins that may be prepared in accordance with the present invention, include formulations to treat acne, liver spots, skin aging and the like.

Oil Bodies as Vehicles to Isolate Multimeric Recombinant Protein Complexes

Once the oil bodies comprising the multimeric-protein-complexes, heteromultimeric-protein-complexes, multimeric-fusion-proteins, heteromultimeric-fusion-proteins, immunoglobulins, immunoglobulin-polypeptide-chains, redox-fusion-polypeptides have been isolated, the multimeric-protein-complexes may be separated from the oil bodies. In embodiments of the invention in which the oil bodies are associated with the multimeric-protein-complexes in a non-covalent manner such a separation may be accomplished by eluting the multimeric-protein-complexes from the oil bodies using an appropriate elution buffer. The multimeric-protein-complexes may then conveniently be separated from the oil bodies by density centrifugation or any other methodology allowing separation of the oil bodies from the multimeric protein complex. In this manner immunoglobulins associated with oil bodies through for example Protein A, may be separated from the oil bodies. In embodiments of the invention in which the multimeric protein complex is covalently associated with the oil body—either through covalent association of the first recombinant polypeptide or the second recombinant polypeptide, or both the first and second recombinant polypeptide—the covalent linkage may be designed to be sensitive to cleavage by a chemical or enzymatic cleavage agent. Application of the cleavage agent results in breaking of the linkage between the oil bodies and multimeric protein complexes. As above, separation of the multimeric-protein-complex from the oil bodies may be accomplished using for example density centrifugation. The isolated multimeric-protein-complexes may be used in accordance with applications for such complexes known to those skilled in the art.

The following examples are included for illustrative purposes only and are not intended to limit the scope of the invention.

EXAMPLE 1

Production of Multimeric Immunoglobulin Protein in Plant Seed Cells and Capture on Oil Bodies Using Protein A—oleosin Fusion Proteins 1+ Production of Multimeric Immunoglobulin Protein in Plant Seed Cells For expression of multimeric-protein-complexes containing multimeric-immunoglobulin-complexes, the cDNA sequences encoding individual light and heavy chains can be isolated from; 1) cell lines expressing a particular antibody, such as clonal B cell lines, or a hybridoma cell line, or 2) may be a recombinant antibody, assembled by combining select light and heavy chain variable domains and available light and heavy chain constant domain sequences, respectively. Variable domains with specific binding properties may be isolated from screening populations of such sequences, usually in the form of a single-chain Fv phage display library.

Starting from known nucleic acid sequences and a source of light and heavy chains, the mature polypeptide coding sequences of each chain is isolated with a secretion signal sequence. The signal sequence can be the native antibody sequence or derived from a known secreted plant sequence (e.g. a PR sequence from *Arabidopsis* or tobacco). The addition of a plant secretion signal sequence to both light and heavy chain mature coding sequences is carried out by standard molecular biology techniques. PCR fusion is used routinely to make such modifications. Secretion signal sequences are included to target the light and heavy immunoglobulin polypeptides for secretion from the cell and further assembly of the two chains into a multimeric-immunoglobulin-complex. For expression in transgenic plant seeds, an expression cassette is assembled comprising: 1) a regulatory promoter sequence to provide expression in plant seeds, 2) the secretion signal-light chain sequence, and 3) a regulatory sequence to terminate transcription. A second expression cassette is assembled comprising: 1) a regulatory promoter sequence to provide expression in plant seeds, 2) the secretion signal -heavy chain sequence, and 3) a regulatory sequence to terminate transcription. Each of the antibody chain expression cassettes is cloned individually into an *Agrobacterium* plant transformation vector or is combined into a single transformation vector with both expression cassettes. In both cases, the expression cassettes are cloned into plant transformation vectors, between the left and right delineating border sequences, and adjacent to a plant selectable marker cassette. Each plant transformation vector is transformed into *Agrobacterium*. The resulting *Agrobacterium* strains are used to infect plant tissues. Transgenic plant material is regenerated and viable transgenic plants are selected. When individual transformation vectors are used, the transgenic plant lines that are produced, expressing either light or heavy chain sequences, are crossed to generate a single plant line expressing both chains in the same plant cell. When a single transformation vector, containing both light and heavy expression cassettes, is used, the initial transgenic plant line produces both light and heavy chain sequences in the same plant cell.

2+ Production of Transgenic Oil Bodies Which Display Protein A for the Capture of Immunoglobulins To capture and display immunoglobulin protein on oil bodies, oil bodies are engineered to display an immunoglobulin binding protein. In this example, the well-known antibody-binding domains from Protein A are used. Based on the known sequence for Protein A from Staphylococcus aureus, PCR primers are designed to isolate the five consecutive Ig-binding domains from the bacterial Protein A sequence. Primers are designed to allow cloning of the Protein A sequence as either an N-terminal or C-terminal fusion to an oleosin sequence for targeting to oil bodies. The sequence that encodes an in-frame translational fusion between Protein A and oleosin is cloned into a plant expression cassette for seed-specific expression. The final cassette consists of a regulatory promoter sequence that provides expression in seeds, the Protein A—oleosin fusion sequence, and a regulatory sequence to terminate transcription. The Protein A—oleosin expression cassette is cloned into a plant transformation vector compatible with *Agrobacterium* — mediated plant transformation. The transformation vector comprises left and right border sequences flanking the Protein A—oleosin expression cassette and an adjacent plant selectable marker cassette. The *Agrobacterium* strain containing this vector is used to infect plant tissues and subsequent regeneration and selection from transgenic plant material to create transgenic plants.

3+ Capture and Display of Multimeric-immunoglobulins on Oil Bodies Displaying Protein A Having produced light and heavy chain multimeric immunoglobulin complexes in one transgenic plant line and the display of Protein A on oil bodies through the oil body targeting of a Protein A—oleosin fusion protein in a second plant line, at least two embodiments can be used to capture the immunoglobulin complex on the Protein A oil bodies. In the first embodiment, transgenic seed from both the immunoglobulin and the Protein A—oleosin expression lines is combined in an optimum ratio and then ground together such that the disrupted material from both seed lines would be combined in the same extract. The combined seed extracts are mixed and/or incubated under conditions that allow maximum recovery of the immunoglobulin by Protein A. The oil body fraction is separated using standard phase separation techniques (e.g. centrifugation). The recovered oil body fraction contains both native oil bodies, from the immunoglobulin expression line, and transgenic Protein A oil bodies from the Protein A—oleosin expression line.

In a second embodiment, the plant lines expressing the immunoglobulin complex and the Protein A—oleosin fusion are crossed and individual plant lines expressing both components are identified and propagated. In this approach, the immunoglobulin complex and the Protein A—oleosin fusion are produced in different cellular compartments of the same plant seed cell. Seed from the double transgenic line is ground to disrupt the cellular material and mix the contents of all cellular compartments, including combining the immunoglobulin in the extracellular compartment and the Protein A—oleosin on the oil body in the cytosolic compartment. The material is mixed and/or incubated under conditions to allow maximum recovery of the immunoglobulin by Protein A, and the oil body fraction is separated by phase separation techniques. The recovered oil body fraction contains the displayed Protein A and the capture immunoglobulin complex.

EXAMPLE 2

Production of Assembled Multimeric-immunoglobulin-complexess as Fusions with Oil Body Targeting Domains Individual polypeptides are produced as a fusion protein with oil body targeting sequences (e.g. oleosin) for display on oil bodies. It has been found that the individual subunits of naturally associating heterodimeric proteins can be co-produced as individual oleosin fusions and still associate as an active heterodimer on the surface of the oil body. In this example, the heterodimer is the light and heavy chain subunits, or derived portions thereof, of an immunoglobulin complex.

Production of an Immunoglobulin Fab Complex on Oil Bodies

The mature light chain sequence, lacking the secretion signal sequence, is attached as an in-frame N-terminal fusion to an oleosin sequence. This fusion sequence is assembled into a seed-specific expression cassette consisting of a seed-specific promoter sequence, the light chain—oleosin fusion sequence, and a transcriptional terminator sequence. The expression cassette is inserted between the left and right border markers, adjacent to a plant selectable marker cassette, of a transformation vector. The transformation vector, in *Agrobacterium*, is used to infect plants and generate transgenic plants.

An equivalent construct for the heavy chain subunit, comprising the variable and constant heavy chain domains, is also attached as an in-frame fusion to oleosin and assembled into an expression cassette for seed-specific expression. The expression cassette can be a part of a separate transformation vector for the generation of a separate transgenic line, or the heavy chain expression cassette can be combined together with the light chain cassette into a single transformation vector. If light and heavy chain expression cassettes are transformed into plants on separate transformation vectors, the individual plant lines are crossed to create a single line expressing both heterodimer subunit—oleosin fusions in the same plant cell. Seed from the double transgenic line, or a single transgenic line generated from the dual expression vector, is extracted to isolate oil bodies. The seed material is ground to release the cellular contents and oil bodies are isolated by phase separation. The targeting of both light and heavy chain sequence to oil bodies, as oleosin fusions, allows the association of the immunoglobulin complex on the surface of the oil body.

Similar configurations, using the entire heavy chain sequence in combination with the entire light chain sequence, or using the variable domains from both the light and heavy chain sequences, are constructed to assemble different types of heteromultimeric-immunoglobulin-complexes (e.g., heterodimers) on the surface of oil bodies.

EXAMPLE 3

To assemble immunoglobulin complexes on the surface of oil bodies requires 1) the use of an oil body-binding domain (e.g. anti-oleosin MAb or scFv) as part of the immunoglobulin complex (EXAMPLE 3), or 2) the use of an immunoglobulin binding domain attached to the surface of oil bodies (EXAMPLE 4).

Isolation of an Anti-Oleosin Monoclonal Antibody-Producing Hybridoma Cell Line

To produce monoclonal antibodies (MAb) which specifically bind to the oleosin protein on the surface of oil bodies, an *Arabidopsis* oleosin cDNA sequence (*Arabidopsis* Stock Center; GI: 16928) was cloned into an expression vector for recombinant protein production in *E. coli*. The oleosin coding sequence was selectively amplified by a polymerase chain reaction (PCR) using primers #0013 (SEQ ID NO:1) and #0605 (SEQ ID NO:2) to engineer an NcoI site at the translation initiation codon (ATG) and a HindIII site following the translation termination codon (TAA), respectively.

```
Primer # 0013:
5' CGCGGATCCATGGCGGATACAGCTAGA 3'    (SEQ ID NO:1)
(NcoI site underlined)

Primer # 0605:
5' AAGCTTAAGTAGTGTGCTGGCCACC 3'      (SEQ ID NO:2)
(HindIII site underlined)
```

The oleosin PCR fragment was cloned and confirmed by DNA sequencing. The oleosin sequence was then digested with NcoI and HindIII, and cloned into the NcoI and HindIII sites of pRSET B (Invitrogen) to create an *E. coli* expression vector. The vector is designed to produce a peptide containing six tandem histidine residues and a T7 epitope fused to the 5' end of the inserted oleosin sequence. The pRSET B vector containing the *Arabidopsis* oleosin sequence was transformed into the *E. coli* strain BL21(DE3) containing an inducible T7 RNA polymerase gene. A confirmed clone was grown in liquid media and induced to produce the recombinant oleosin protein (Schoepfer R. (1993) Gene 14: 83–85; Kroll D. J. et al (1993) DNA Cell. Biol. 12: 441–453). The oleosin protein was produced as an insoluble aggregate in *E. coli*. The cell pellet was collected by centrifugation, and the inclusion body fraction was solubilized in SDS loading buffer and separated by preparative SDS-PAGE. The gel strip containing the recombinant oleosin protein was excised and the protein was electroeluted from the gel in SDS-PAGE running buffer. The eluted oleosin protein was dialyzed against a minimal amount of SDS to maintain solubility of the oleosin protein. Using this material as the antigen for MAb production, standard procedures were used to immunize mice and recover hybridoma cell lines producing anti-oleosin monoclonal antibodies (Antibodies: A Laboratory Manual. (1988) Harlow E. & Lane D. Cold Spring Harbour Press). Several clones showed specificity for the Arabidopsis oleosin when used in Western blots to detect *Arabidopsis* seed extracts. Based on signal intensity and specificity, the D9 clone was selected for further manipulation. The D9 MAb was confirmed to bind to the surface of intact oil bodies isolated from *Arabidopsis* seeds, a functional requirement for its use as an oil body associating-sequence.

Primer Design for Isolating the D9 Heavy and Light Chain Sequences

To isolate a cDNA copy of the complete D9 heavy and light chain coding sequences from the D9 hybridoma cell line, the variable regions of each chain were isolated using the Recombinant Phage Antibody System (RPAS; Amersham Biosciences). The RPAS protocols for reverse transcription (RT)-PCR were followed to amplify the heavy variable and light variable domains from D9 hybridoma-derived mRNA. The DNA sequence of the cloned D9 heavy and light chain variable domains was determined. Using a commercially available kit, the isotype class of the D9 MAb chains was also determined and found to be IgG1 and kappa for the heavy and light chains, respectively. The isotype and variable domain sequence information was used to determine more precisely the gene or gene subgroup from which the D9 MAb arose. The known sequences for other members of the same subgroup were then used to design primers outside the known regions of the D9 sequence. This allowed the complete coding sequence of the D9 heavy and light chains to be isolated.

The D9 heavy chain variable sequence was used as a query to search the Genbank database using the BLAST algorithm (www.ncbi.nlm.nih.gov). Four entries with the strongest sequence match to the D9 heavy variable domain, and that also contain sequence encompassing the secretion signal peptide upstream of the mature coding sequence, were selected for alignment (Genbank IDs GI: 2791981, 195311, 195307, 195305). The small number of sequence differences between D9 and the other four antibody sequences suggested that D9 also arose from the same germline sequence. The secretion signal sequences for all four antibodies were identical. Therefore a single specific forward primer was designed to this region (#1020—SEQ ID NO:3). Since the D9 heavy chain was identified as an IgG1 isotype, mouse sequences encoding the IgG1 C-terminal constant domain (GI: 1513181, 861030) were used to design a single specific reverse primer downstream of the coding sequence termination codon (#1021—SEQ ID NO:4).

```
Primer # 1020:
5' CTGTCAGTAACTGCAGGTGTC 3'      (SEQ ID NO:3)

Primer # 1021:
5' GTAGGTGTCAGAGTCCTGTAG 3'      (SEQ ID NO:4)
```

A Genbank database search using the D9 light chain variable sequence as a BLAST query identified four sequences with strong identity and which also included sequence upstream encoding the secretion signal peptide (GI: 2906115, 286098, 286086, 5327121). Within the aligned variable regions a number of base differences were apparent, therefore instead of a single specific primer, a degenerate primer sequence was used with broader specificity for the light chain subgroup I family of sequences (#1022 (SEQ ID NO:5); Chardès T. et al (1999) FEBS Letters 452: 386–394). Based on the identification of the D9 light chain as a kappa isotype, the mouse germline sequence encoding the kappa C-terminal constant domain (GI: 51657) was used to design a specific reverse primer downstream of the coding sequence termination codon (#1023 (SEQ ID NO:6)).

```
Primer # 1022:
5' TCTGGGTATCTGGTRCSTGTG 3'      (SEQ ID NO:5)

Primer # 1023:
5' GCAACAGTGGTAGGTCGCTTG 3'      (SEQ ID NO:6)
```

Isolation of Anti-Oleosin D9 Monoclonal Antibody Heavy and Light Chain cDNA Sequences and Construction of a Dual Expression Transformation Vector The mouse hybridoma cell line expressing the D9 monoclonal antibody was used as the source of RNA for the D9 heavy and light chain sequences. Messenger RNA (mRNA) was isolated from the D9 hybridoma cell line using the QuickPrep Micro mRNA Purification kit (Amersham Biosciences). RT-PCR (Titan One Tube RT-PCR System; Roche Applied Science) was carried out on the D9 hybridoma mRNA using primers #1020 (SEQ ID NO:3) and #1021 (SEQ ID NO:4) or #1022 (SEQ ID NO:5) and #1023 (SEQ ID NO:6) to amply the D9 IgG1 heavy chain and kappa light chain sequences respectively. The D9 heavy and light chain PCR products were each cloned into the pCR2.1 vector (Invitrogen). The DNA sequence was determined for the insert in each of the resulting clones (pSBS2801 heavy chain and pSBS2800 light chain). As the primers were designed outside the D9 heavy and light chain coding sequences (for the purpose of obtaining complete native coding sequence) removal of these extra sequences was required for expression in plants. In addition, the partial mouse secretion signal sequences present in each sequence was replaced with a complete plant-derived secretion signal sequence.

Primers were designed and synthesized to selectively amplify the mature protein coding sequence for each chain. These primers were designed as part of a larger set, which when assembled by PCR fusion (Sandhu G. S. et al (1992) BioTechniques 12:14–16), attached a complete secretion signal sequence to the 5' end of both heavy and light chain sequences. The secretion signal DNA sequences were designed de novo but encode the secretion peptide of the tobacco pathogenesis-related thaumatin-like protein (GI: 131017, 19857). In addition, restriction enzyme sites were included 5' of the secretion signal sequence and 3' of the coding sequence of each chain to facilitate subsequent cloning. PCR of the heavy chain sequence used pSBS2801 as a template and primers #1207 (SEQ ID NO:7), #1208 (SEQ ID NO:8), #1209 (SEQ ID NO:9), #1210 (SEQ ID NO:10) and #1211 (SEQ ID NO:11). PCR of the light chain sequence used pSBS2800 as a template and primers #1202 (SEQ ID NO:12), #1203 (SEQ ID NO:13), #1204 (SEQ ID NO:14), #1205 (SEQ D NO:15) and #1206 (SEQ ID NO:16).

```
Primer # 1202:
5' GCGCCTCGAGATCTACCATGAACTTCCTCAAGT (SEQ ID NO:12)
                                CTTTC 3'
(XhoI site underlined)

Primer # 1203:
5' GACCAAAGCAGAGAAAAGCATAAAACGGGAAAG (SEQ ID NO:13)
                              ACTTGAGGAAGTTCAT 3'

Primer # 1204:
5' GCTTTTCTCTGCTTTGGTCAGTATTTCGTCGCT (SEQ ID NO:14)
                                GTTACCCATGCT 3'

Primer # 1205:
5' GACTGTGTCATCACAATGTCAGCATGGGTAACA (SEQ ID NO:15)
                                   GCGACG 3'

Primer # 1206:
5' GCGCAGATCTCGAGCTAACACTCATTCCTGTTG (SEQ ID NO:16)
                                     AAGC 3'
(XhoI site underlined)

Primer # 1207:
5' GCGCAGATCTAACATGAACTTTCTCAAGTCC   (SEQ ID NO:7)
                                  3'
(BgIII site underlined)

Primer # 1208:
5' GTCCGAAACAGAGGAAAGCGTAGAATGGAAAGG (SEQ ID NO:8)
                              ACTTGAGAAAGTTCAT 3'

Primer # 1209:
5' GCTTTCCTCTGTTTCGGACAATACTTTGTTGCT (SEQ ID NO:9)
                                GTCACTCACGCT 3'
```

-continued

```
Primer # 1210:
5' GACTGCTGCAGGTGAACCTGAGCGTGAGTGACA (SEQ ID NO:10)
                                GCAAC 3'

Primer # 1211:
5' GCGCAGATCTTCATTTACCAGGAGAGTGG 3'  (SEQ ID NO:11)
(BgIII site underlined)
```

The assembled signal sequence—D9 heavy chain PCR product was cloned into pCR2.1 (Invitrogen) to generate pSBS2803. The assembled signal sequence—D9 light chain PCR product was cloned into pCR2.1 to generate pSBS2802. To create the plant transformation vector containing dual D9 heavy and light expression cassettes, the signal sequence—D9 heavy chain was cut from pSBS2803 with BgIII and cloned into the compatible BamHI site of pSBS4014, between the phaseolin promoter and phaseolin terminator regulatory elements, creating pSBS4800. The phaseolin promoter and terminator gene regulatory elements are derived from the common bean Phaseolus vulgaris (Slightom et al (1983) Proc. Natl. Acad. Sci. 80: 1897–1901; Sengupta-Gopalan et al (1985) Proc. Natl. Acad. Sci. USA 82: 3320–3324) and are used to achieve seed-specific over expression. pSBS4014 was constructed by inserting a (PstI MluI)—phaseolin promoter—(BamHI)—phaseolin terminator—(KpnI) cassette into the PstI and KpnI sites of pSBS4004 (described below).

The signal sequence—D9 light chain was cut from pSBS2802 with XhoI and cloned into the XhoI site of pSBS2808, between the flax linin storage protein promoter and terminator sequences (see patent WO 01/16340)), to create pSBS2810. These storage protein regulatory elements are also used to achieve seed-specific over expression. The linin promoter—secretion signal D9 light chain—linin terminator cassette (SEQ ID NO:17) was excised from pSBS2810 with the MluI sites flanking the cassette and cloned into the MluI site upstream of the phaseolin D9 heavy chain cassette (SEQ ID NO:18) in pSBS4800. The two heavy and light cassettes in the final transformation vector pSBS4803 were in a divergent orientation relative to direction of transcription for each cassette.

The pSBS4803 transformation vector was electroporated into Agrobacterium strain EHA101 (Hood et al (1986) J. Bacteriol. 168: 1291–1301). A confirmed Agrobacterium clone was used to transform Arabidopsis. Arabidopsis transformation was done essentially as described in "Arabidopsis Protocols: Methods in Molecular Biology" Vol 82. (Edited by Martinez-Zapater J M and Salinas J. ISBN 0-89603-391-0 pg 259–266 (1998)) with the modification of selecting putative transgenic plants on agarose plates containing 80 µM L-phosphinothricine. Plants which survived selection were transplanted to soil and allowed to set seed.

Extraction of D9 Antibody Complexes Associated with Oil bodies

A representative SBS4803 transgenic Arabidopsis line was tested for association of the assembled D9 heavy and light chain antibody complex with the surface of extracted oil bodies. The behavior of mouse IgG1 antibody protein with no affinity for oil bodies and anti-oleosin D9 mAb, produced and purified from the original D9 hybridoma cell line, were analyzed as negative and positive controls respectively.

Forty milligrams of non-transgenic wild type Arabidopsis C24 seed was ground in 150 ul of 50 mM sodium phosphate buffer pH 8.0. The extract was centrifuged for 10 minutes at 4° C. and the oil body and soluble undernatant fractions were removed to a new tube. The pellet was re-extracted with 100 ul of sodium phosphate buffer. The tube was centrifuged at 4° C. for 10 minutes, and the oil body and soluble undernatant fraction was pooled with the first equivalent fraction. The pooled oil body and soluble undernatant fractions were centrifuged for 10 minutes at 4° C. and the oil body fraction was recovered and resuspended in 200 ul of sodium phosphate buffer. To equal aliquots of the oil bodies was added 15 ug of either mouse IgG1 antibody (Sigma) or D9 MAb purified from the hybridoma cell culture medium. The samples were centrifuged and the undernatants were removed to a fresh tube. The undernatants were clarified twice more by centrifugation before SDS-PAGE. The oil body fractions were washed three times by repeated centrifugation and resuspension in 200 ul of sodium phosphate buffer. The final washed oil bodies and clarified undernatants were solubilized in SDS loading buffer before analysis be SDS-PAGE. Similar to the control treatments above, 20 mg of transgenic SBS4803 seed was ground in 50 mM sodium phosphate buffer pH 8.0 and centrifuged for 10 minutes at 4° C. The soluble undernatant was removed and clarified by two further centrifugation steps to remove trace oil bodies. The first SBS4803 oil body fraction was washed three times by repeat centrifugation and resuspension in 200 ul of sodium phosphate buffer. The oil body and undernatant samples were solubilized in SDS loading buffer before SDS-PAGE analysis. The mouse IgG1 control antibody protein, when added to wild type Arabidopsis oil body extracts, does not interact with oil bodies and partitions with the undernatant fraction (FIG. 2). The anti-oleosin D9 mAb, purified from the original mouse hybridoma cell line, partitions with the oil body fraction. Extraction of the SBS4803 transgenic Arabidopsis seed shows the D9 mAb, produced and assembled within the seed, also associates with the oil body fraction.

EXAMPLE 4

As described above for the mouse D9 antibody, standard hybridoma techniques may be used to isolate antibody sequences for MAbs which bind a wide range of different antigens. To assemble antibody complexes on oil bodies, particularly for those antibodies that do not bind directly to oil body-associated antigens, requires the assembly to be mediated by an immunoglobulin-binding domain attached to the surface of the oil body. In this example, the IgG-binding domains of Protein A from Staphylococcus aureus are attached to the surface of the oil body, to mediate the association of immunoglobulin complexes on oil bodies. To make the immunoglobulin complex compatible with Protein A binding, mouse MAb sequences are converted to mouse/human chimeric sequences. The Fc region of human IgG1, IgG2 and IgG4 immunoglobulin isotypes bind strongly to Protein A, in contrast to the equivalent Fc region of mouse IgG proteins. By replacing the mouse Fc region on the heavy chain and the constant domains on both heavy and light chains with the equivalent human sequences, a chimeric antibody complex can assemble which now binds to Protein A.

Construction of a Dual Expression Transformation Vector for the Production of an Assembled Chimeric Antibody Additional mouse monoclonal antibodies, with affinity for non-oil body related antigens, can be cloned from mouse hybridoma cell lines following a procedure similar to that used for the D9 MAb. Following well defined procedures, the mouse heavy and light chain variable domains can be fused to the constant domains from human heavy and light chain sequences to generate chimeric antibodies (Sahagan B. G. et al (1983) J. Immunol. 137: 1066–1074; Hutzell P. et al (1991) Cancer Res. 51: 181–189).

The heavy and light chain sequences of a chimeric antibody were both modified by PCR fusion to attach a secretion signal sequence and flanking restriction enzyme sites for cloning (described above for D9 MAb). The signal peptide—chimeric heavy chain sequence in pSBS2819 was excised with BglII and cloned into the compatible BamHI site of pSBS4014 (described above) between the phaseolin promoter and terminator sequences to create pSBS4807. The signal peptide—chimeric light chain sequence in pSBS2820 was excised with XhoI and cloned into the XhoI site between the linin promoter and terminator in pSBS4013 to create pSBS4808. pSBS4013 is equivalent to pSBS4014 but contains the (MluI)—linin promoter—(XhoI)—linin terminator—(MluI) cassette upstream of the phaseolin promoter—terminator sequence. The MluI fragment from pSBS4808, containing the linin promoter—chimeric light chain—linin terminator cassette, was cloned upstream of the phaseolin promoter—chimeric heavy chain—phaseolin terminator cassette in pSBS4807 to generate tandem dual expression vectors. The clone with the two expression cassettes in a divergent orientation is pSBS4809, and the clone with the expression cassettes in a series configuration is pSBS4810.

The chimeric antibody transformation vectors pSBS4809 and pSBS4810 were electroporated into *Agrobacterium* strain EHA101 (Hood et al (1986) J. Bacteriol. 168: 1291–1301). The pSBS4810 *Agrobacterium* strain was used to transform *Arabidopsis*. *Arabidopsis* transformation was done essentially as described in "*Arabidopsis* Protocols: Methods in Molecular Biology" Vol 82. (Edited by Martinez-Zapater J M and Salinas J. ISBN 0-89603-391-0 pg 259–266 (1998)) with the modification of selecting putative transgenic plants on agarose plates containing 80 µM L-phosphinothricine. Plants surviving selection were transplanted to soil and allowed to set seed.

Transgenic *Arabidopsis* seed from representative SBS4809 lines (#6 & #13) were analyzed for the co-production of chimeric heavy and light chains and their assembly into a immunoglobulin complex. Twenty five to thirty seeds of each line were ground in 50 ul of 50 mM Tris-HCl buffer pH 7.6. An equal volume (50 ul) of 2×SDS loading buffer, either with or without the reducing agent (dithiothreitol, DTT) component included, was added to each sample. The samples were heated and clarified before SDS-PAGE. Wild type *Arabidopsis* C24 seed was included as a negative control. Human IgG1 (Sigma) and purified mouse D9 MAb were included as comparative controls (FIG. 3A). Two additional replicate gels were electroblotted for Western blot analysis (FIG. 3B). Detection with an anti-human IgG Fc (heavy chain-specific) antibody indicated the production of the chimeric heavy chain (reduced sample) and its association into a higher molecular weight complex (nonreduced sample) comparable to the mouse and human antibody controls. Detection with an anti-human kappa-specific antibody indicated the production of the chimeric light chain (reduced sample) and its association into a higher molecular weight complex (nonreduced sample) comparable to the mouse and human antibody controls.

Synthesis of a Protein A Coding Sequence for Enhanced Expression in Plants

For enhanced expression of Protein A in plants, a DNA sequence encoding the five tandem immunoglobulin (IgG)-binding domains from the Protein A sequence of Staphylococcus aureus (aa 37–331; Uhlen M. et al (1984) J. Biol. Chem. 259: 1695–1702) was designed and synthesized de novo. The 295 amino acid sequence, encoding the IgG-binding domain repeats, was backtranslated using a codon frequency table for *Arabidopsis* thaliana. The DNA sequence resulting from the backtranslation was further analyzed and modified. Sequence motifs, representing different potential RNA processing signals (AATAAA, AATGGAA, AATGGA, AATGAA, TATAAA, AATAAT, ATTTA, GTAAAA, GTAAGT, GTACGT, GCAG), within the backtranslated DNA coding sequence were identified. Where possible, each motif was eliminated. This was done by changing the sequence within a motif without modifying the Protein A coding potential of the overall sequence. These "silent" DNA changes were made by selecting alternate amino acid codons for any codon overlapping a motif. Alternate codons were selected only if; 1) they encoded the same amino acid, 2) they did not create a tandem duplication with adjacent codons, and 3) they introduced a DNA base change which reduced the identity with the original motif. The process of searching for and eliminating motifs was repeated until remaining motifs could not be eliminated without altering the encoded amino acid sequence. The final DNA sequence was theoretically translated and shown to encode a protein with 100% amino acid identity to the five IgG-binding domains of Staphylococcus aureus Protein A (FIG. 4).

To synthesize the DNA sequence designed by the process described above, sixteen overlapping primers (#1184 (SEQ ID NO:19), #1185 (SEQ ID NO:20), #1186 (SEQ ID NO:21), #1187 (SEQ ID NO:22), #1188 (SEQ ID NO:23), #1189 (SEQ D NO:24), #1190 (SEQ ID NO:25), #1191 (SEQ ID NO:26), #1192 (SEQ ID NO:27), #1193 (SEQ ID NO:28), #1194 (SEQ ID NO:29), #1195 (SEQ ID NO:30), #1196 (SEQ D NO:31), #1197 (SEQ ID NO:32), #1198 (SEQ ID NO:33), #1199 (SEQ ID NO:34)) ranging in size from 51–81 bp, were chemically synthesized and assembled using PCR-based primer extension and PCR fusion (Sandhu G. S. et al (1992) BioTechniques 12:14–16). The primers were designed as eight pairs of alternating forward and reverse primers.

```
Primer # 1184 (forward):
5' GCACAGCATGATGAAGCACAGCAGAATGCTTTC (SEQ ID NO:19)
TACCAGGTGCTCAACATG 3'

Primer # 1185 (reverse):
5' GTCGTCTTTAAGCGATTGGATGAAGCCGTTACG (SEQ ID NO:20)
TTGATCAGCATTGAGATTGGGCATGTTGAGCACCTG
GTAG 3'

Primer # 1186 (forward):
5' CCAATCGCTTAAAGACGACCCTTCCCAGAGCGC (SEQ ID NO:21)
TAATGTCCTCGGCGAAGCTCAAAAGCTGAACGACAG
CCAAGCTC 3'

Primer # 1187 (reverse):
5' CTCGTAAAAGGCTGACTGTTGATCTTTGTTGAA (SEQ ID NO:22)
GTTGTTCTGTTGAGCATCCGCTTTTGGAGCTTGGCT
GTCGTTCAG 3'

Primer # 1188 (forward):
5' CAGTCAGCCTTTTACGAGATCCTTAATATGCCC (SEQ ID NO:23)
AACCTCAACGAGGCCCAGCGTAATGGTTTCATCCAA
TCTCTTAAGGAC 3'
```

-continued

```
Primer # 1189 (reverse):
5' CTCGTTTAGCTTCTTAGCTTCACCCAAAACGTT  (SEQ ID NO:24)
GGTCGACTGCGATGGGTCGTCCTTAAGAGATTGGAT
G 3'

Primer # 1190 (forward):
5' GCTAAGAAGCTAAACGAGTCACAGGCTCCTAAA  (SEQ ID NO:25)
GCTGATAACAACTTCAACAAGGAGCAGCAGAACGCC
TTC 3'

Primer # 1191 (reverse):
5' CTGGATGAACCCGTTTCGCTGTTCCTCGTTGAG  (SEQ ID NO:26)
ATTCGGCATGTTGAGGATTTCATAGAAGGCGTTCTG
CTGCTC 3'

Primer # 1192 (forward):
5' CGAAACGGGTTCATCCAGAGTCTTAAAGATGAC  (SEQ ID NO:27)
CCATCCCAATCCGCTAACCTTCTGTCTGAAGCTAAG
AAGCTAAAC 3'

Primer # 1193 (reverse):
5' GAAGGCGTTCTGTTGCTCCTTGTTAAACTTGTT  (SEQ ID NO:28)
GTCGGCTTTGGGCGCCTGGCTCTCGTTTAGCTTCTT
AGCTTC 3'

Primer # 1194 (forward):
5' GAGCAACAGAACGCCTTCTATGAAATTCTGCAT  (SEQ ID NO:29)
CTCCCTAATCTCAACGAGGAACAACGTAACGGTTTC
ATCCAATCG 3'

Primer # 1195 (reverse):
5' GTTCAGTTTCTTGGCCTCCGCCAACAAGTTTGC  (SEQ ID NO:30)
GGATTGACTCGGATCATCCTTAAGCGATTGGATGAA
ACCGTTACG 3'

Primer # 1196 (forward):
5' GAGGCCAAGAAACTGAACGACGCGCAAGCACCA  (SEQ ID NO:31)
AAAGCTGATAACAAGTTCAACAAGGAACAACAGAAT
GC 3'

Primer # 1197 (reverse):
5' GAAGCCGTTTCTTTGTTCCTCAGTGAGATTTGG  (SEQ ID NO:32)
CAAGTGAAGTATCTCGTAGAAAGCATTCTGTTGTTC
CTTG 3'

Primer # 1198 (forward):
5' GGAACAAAGAAACGGCTTCATCCAGAGTTTGAA  (SEQ ID NO:33)
GGATGACCCGTCTGTCAGCAAGGAGATACTAGCTGA
GGCGAAG 3'

Primer # 1199 (reverse):
5' ATTGTCCTCCTCCTTCGGAGCTTGCGCATCGTT  (SEQ ID NO:34)
CAACTTCTTCGCCTCAGCTAGTATC 3'
```

NcoI restriction enzyme sites were added onto both ends of the DNA sequence to facilitate cloning. Each NcoI site (CCATGG) was adjusted such that the ATG within the site (CCATGG) is in the necessary reading frame to encode a methionine codon for 1) translation initiation at the 5' end and 2) correct translational fusion with the initiating methionine codon of oleosin at the 3' end. Maintaining the correct reading frame required the inclusion of an alanine codon as part of the NcoI/methionine addition to the 3' end. The final amplification of the assembled sequence and the attachment of the NcoI sites was performed by an additional PCR using the two primers #1024 (SEQ ID NO:35) and #1025 (SEQ ID NO:36).

```
Primer # 1024:
5' GCGCCATGGCACAGCATGATGAAGCACAGC 3'  (SEQ ID NO:35)
(NcoI site underlined)

Primer # 1025:
5' GCGCCATGGCATTGTCCTCCTCCTTCGGAGC  (SEQ ID NO:36)
3'
(NcoI site underlined)
```

The final PCR product was cloned into pCR2.1 (Invitrogen) to yield pSBS2904 and the Protein A insert was confirmed by DNA sequencing. The final DNA sequence and encoding protein sequence is shown in FIG. 5.

Construction of a Protein A—Oleosin Expression Vector

An expression vector was constructed to allow for the seed-specific over expression of Protein A as an oil body-associated protein. Oil body targeting and display is achieved by producing a fusion protein with an oleosin sequence (van Rooijen G. J. H. & Moloney M. M. (1995) Bio/Technology 13: 72–77). The Protein A sequence was subcloned, as an NcoI fragment from pSBS2904, into the NcoI site of pSBS2091 to generate a Protein A—oleosin translational fusion in construct pSBS2911. pSBS2091 contains the *Arabidopsis* oleosin gene (van Rooijen et al (1992 Plant Mol. Biol. 18: 1177–1179) with a unique NcoI restriction enzyme site at the oleosin initiation methionine (ATG) codon. Flanking the 5' and 3' end of the Protein A—oleosin sequence in pSBS2911 is the phaseolin promoter and the phaseolin terminator sequences respectively. The phaseolin promoter sequence in pSBS2091 has been modified to change the NcoI site (CCATGG) present in the promoter to CCATGA, thus making the NcoI site at the beginning of oleosin unique. The phaseolin promoter and terminator gene regulatory elements are derived from the common bean Phaseolus vulgaris (Slightom et al (1983) Proc. Natl. Acad. Sci. 80: 1897–1901; Sengupta-Gopalan et al (1985) Proc. Natl. Acad. Sci. USA 82: 3320–3324) and are used to achieve seed-specific over expression. The complete promoter—gene fusion—terminator cassette (SEQ ID NO:349) was excised from pSBS2911 as a PstI-Kpnl fragment and cloned into pSBS4004 to generate pSBS4901. pSBS4004 is a derivative of the *Agrobacterium* binary plasmid pPZP221 (Hajdukiewicz et al (1994) Plant Mol. Biol. 25: 989–994). In pSBS4004, the region between the right and left border sequences of pPZP221 has been removed and replaced with PstI, NcoI, Kpnl restriction enzyme sites and a plant selectable marker cassette containing the parsley ubiquitin promoter, the phosphinothricin acetyl transferase gene, and parsley ubiquitin terminator sequences. This selectable marker cassette allows selection of transformed plant cells based on its conferred resistance to the herbicide glufosinate ammonium.

The pSBS4901 and SBS4810 *Agrobacterium* strains were each used to transform the S317 California variety of safflower to generate individual transgenic lines. The transformation procedure was similar to that outlined by Orlikowska T. K. et al. ((1995) Plant Cell, Tissue and Organ Culture 40: 85–91), but with modifications and improvements both for transforming the S317 variety as well as for using phosphinothricin as the selectable marker. Seeds, which were not damaged, cracked or diseased, were decontaminated in 0.1% HgCl2 for 12 min followed by 4–5 rinses with sterile distilled water. Sterile seeds were germinated in the dark on MS medium (Murashige T. & Skoog F. (1962) Physiol. Plant. 15: 473–497) with 1% sucrose and 0.25% Gelrite. *Agrobacterium* cultures were initiated from frozen glycerol stocks in 5 ml AB minimal liquid media with antibiotic selection, and grown for 48 hours at 28° C. For transformation, an aliquot of this culture was grown overnight in 5 ml of Luria broth with selection. Before use, 6–8 ml of bacterial cells were washed twice with AB media, and made up to a final cell density of 0.4 –0.5 (OD600).

Two-day-old cotyledons were removed from germinated seedlings, dipped in the prepared *Agrobacterium* cells, and plated on MS medium with 3% sucrose, 4 uM N6-benzyladenine (BA) and 0.8 uM naphthaleneacetic acid (NAA). Plates were incubated at 21° C. under dark conditions. After 3 days, these were transferred to the same medium with 300 mg/L timentin. After an additional 4 days, all cultures were moved to the light. After 3 days, explants were placed on selection medium with phosphinothricin added at 0.5 mg/L. For continued bud elongation, explants were transferred weekly onto MS medium without phytohormones but with twice and basal amount of KNO3. Shoots that had elongated to greater than 10 mm were excised from the initial explant and individually grown on selection. For rooting, green shoots, representing putative transgenic tissue, were placed on MS medium with 2% sucrose, 10 uM indolebutyric acid and 0.5 uM NAA. Rooted shoots were transferred to a well drained soilless mix and grown under high humidity and 12 hours of light.

Extraction of Assembled Antibody Complexes Associated with Oil Bodies/Antibody and Protein A—Oleosin Components in a Single Seed Line To create a single safflower line expressing both chimeric antibody (SBS4810) and Protein A—oleosin (SBS4901) transgene constructs, single transgenic lines were selected as male and female donor and manually crossed. Capitula or heads at the late bud stage, just before the florets start emerging, were selected. Two hours after the daily artificial light regime began, bracts were removed from selected capitula for crossing, and any expanded florets were removed and discarded. The anther tubes were removed from all remaining florets. These heads were then bagged and labelled. The next day, when the styles were elongated, the bags were removed and the emasculated florets are fertilized with pollen from selected plants. The fertilized head was covered again for approximately one week or until seeds began to develop visually. Seed was allowed to continue development on the plant and was harvested at maturity.

Double transgenic seeds were analyzed for the presence of both recombinant products; production and assembly of the SBS4810 heavy and light antibody chains, and production of the Protein A-oleosin fusion on the surface of oil bodies. Seeds which contained both chimeric antibody and Protein A-oleosin components were used to test the assembly of the antibody complex on the oil bodies, mediated by Protein A. Individual safflower seeds were ground in 150 ul of 50 mM sodium phosphate buffer pH 8.0. The extracts were centrifuged for 10 minutes at 4° C. and the oil body and soluble undernatant fractions were transferred to a fresh tube. The pellet fraction was reextracted in 50 ul of sodium phosphate buffer and the second oil body and soluble undernatant fraction was pooled with the first equivalent fraction. The pooled oil body and undernatant fractions were centrifuged for 10 minutes at 4° C. The soluble undernatant was removed and clarified by two rounds of centrifugation. The oil body fraction was washed three times in 200 ul of 50 mM sodium phosphate buffer pH 8.0. The washed oil bodies and clarified undernatant fractions were solublized in SDS loading buffer and separated by SDS-PAGE before electroblotting for Western analysis. Both SBS4810 chimeric antibody and SBS4901 Protein A-oleosin fusion are detected using a goat anti-human IgG Fc secondary antibody (ICN Biomedicals Inc.).

Figure 6:
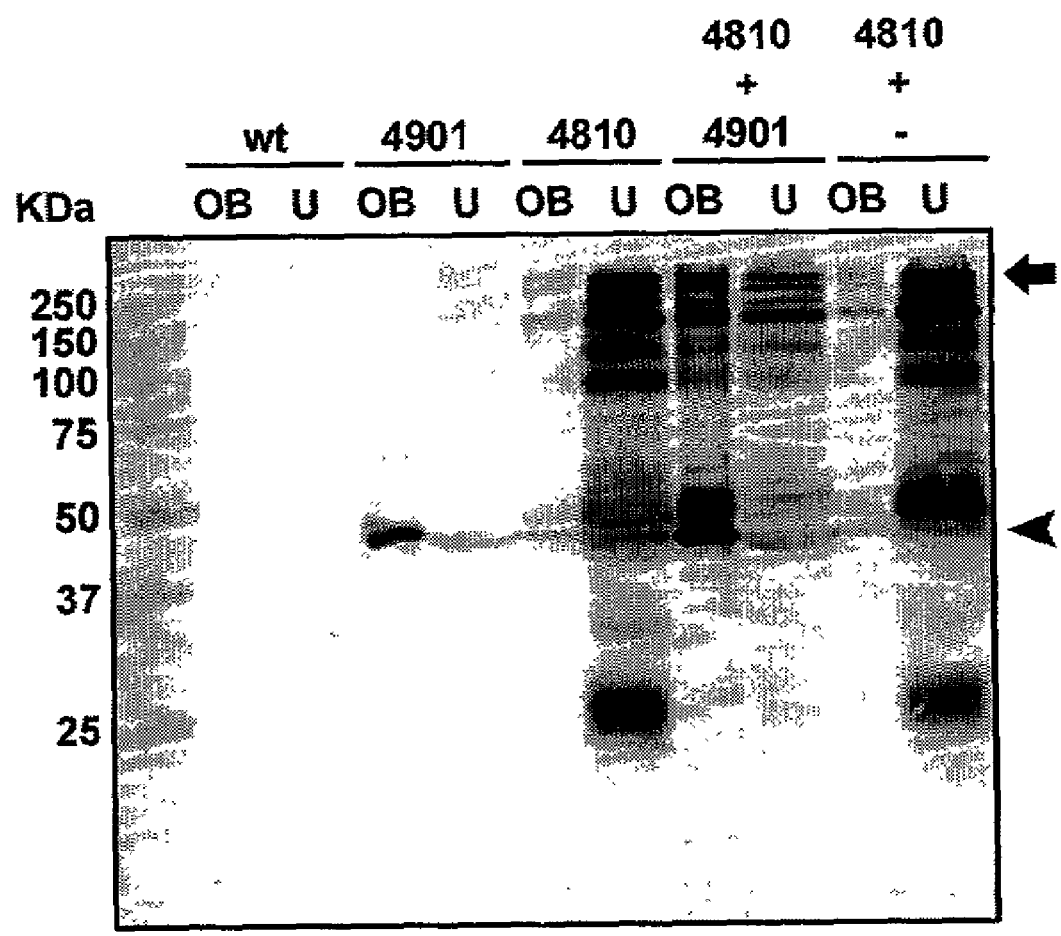
FIG. 6. Individual wild type (wt) or transgenic safflower seeds were extracted and oil body (OB) and soluble undernatant (U) fractions were analyzed by Western blot. Detection was performed using a goat anti-human IgG Fc-specific secondary antibody (ICN Biomedicals Inc.). Seeds analyzed were from individual transgenic lines (Protein A-oleosin SBS4901, chimeric heavy and light chain SBS4810) or seeds resulting from the cross of the SBS4901 and SBS4810 transgenic lines. The double transgenic seed (SBS4810+ SBS4901) and single transgenic seed (SBS4810+−) resulting from the cross are compared to the single transgenic lines.

The recombinant protein profiles of wild type safflower or individual transgenic safflower lines for Protein A—oleosin (SBS4901) or chimeric heavy and light antibody chains (SBS4810) are shown in FIG. 2. No antibody or Protein A products are detected in the oilbody or soluble undernatant fractions of the wild type safflower seed. The Protein A—*Arabidopsis* oleosin fusion protein is detected predominantly in the undernatant fraction from the SBS4901 safflower seed (arrowhead, FIG. 6). Protein A is detected through direct binding to the goat secondary antibody. A number of antibody derived proteins and complexes are produced and detected in the SBS4810 safflower seed, including the completely assembled immunoglobulin (arrow, FIG. 6). The majority of these protein products partition with the soluble undernatant, with only a minor portion is associating non-specifically with the oilbody fraction. Since the transgenic lines used as donor parent lines for the crosses, were segregating the Protein A or chimeric antibody transgene respectively, not all seed resulting from the cross inherited both transgenes. The "SBS4810+−" seed produced from the cross did not inherit the SBS4901 Protein A—oleosin transgene and has an antibody profile comparable to the original SBS4810 transgenic line. This demonstrates that the antibody partitioning between oilbodies and soluble undernatant has not changed as a result of the crossing manipulation itself. The seed producing both transgenes (SBS4810 +SBS4901) however shows a marked increase in the association of antibody products (including the full length immunoglobulin complex) with the oilbodies.

The present invention should therefore not be seen as limited to the particular embodiments described herein, but rather, it should be understood that the present invention has wide applicability with respect to protein expression generally. Since modifications will be apparent to those of skill in this art, it is intended that this invention be limited only by the scope of the appended claims.

All publications, patents and patent applications are herein incorporated by reference in their entirety to the same extent as if each individual publication, patent or patent application was specifically and individually indicated to be incorporated by reference in its entirety.

SUMMARY OF SEQUENCES

SEQ ID NOs:1 and 2 set forth primers which were designed to amplify the oleosin coding sequence and to engineer an NcoI site at the translation initation codon (ATG) and a HindIII site following the translation termination codon (TAA), respectively.

SEQ ID NOs:3 and 4 set forth primers which were designed to an antibody secretion signal sequence and the sequence downstream of the IgG1 isotype termination codon respectively to amplify the D9 heavy chain.

SEQ ID NOs:5 and 6 set forth primers which were designed to represent a degenerate primer sequence was used with broader specificity for the light chain subgroup I family of sequences and the sequence downstream of the coding sequence termination codon to amplify the D9 light chain variable sequence.

SEQ ID NOs:7 to 11 set forth primers which were designed to add a secretion sequence to the D9 heavy chain through primer extension.

SEQ ID NOs:12 to 16 set forth primers which were designed to add a secretion sequence to the D9 light chain through primer extension.

SEQ ID NO:17 sets forth the sequence of the linin promoter—secretion signal D9 light chain—linin terminator cassette excised from pSBS2810

SEQ ID NO:18 sets forth the sequence of the phaseolin promoter—signal sequence—D9 heavy—phaseolin terminator cassette from pSBS4800.

SEQ ID NOs:19–34 set forth primers designed to synthesize the Protein A sequence found in FIG. 4.

SEQ ID NOs:35 and 36 set forth primers designed to attach NcoI sites on the Protein A sequence found in FIG. 4.

SEQ ID NO:37 sets forth the sequence of the Phaseolin promoter—Egineered Protein A—*Arabidopsis* Oleosin gene (with intron)—Phaseolin terminator excised from pSBS2911 as a PstI—Kpnl fragment and cloned into pSBS4004 to generate pSBS4901.

SEQ ID NO:38 sets forth the sequence shown in FIG. 4.

SEQ ID NO:39 sets forth the sequence shown in FIG. 5.

What is claimed is:

1. A method of producing an oil body associated with a recombinant multimeric-immunoglobulin, said method comprising:
    (a) producing in a cell comprising oil bodies, a first immunoglobulin-polypeptide-chain and a second immunoglobulin-polypeptide-chain wherein said first immunoglobulin-polypeptide-chain is capable of associating with said second immunoalobulin-polypeptide-chain to form said multimeric-immunoglobulin; and
    (b) associating said multimeric-immunoglobulin with an oil body through an oil-body-targeting-protein capable of associating with said oil body and said first immunoglobulin-polypeptide-chain.

2. The method of claim 1 further comprising (c) isolating said oil bodies associated with said multimeric-immunoglobulin.

3. The method of claim 1 wherein said multimeric-immunoglobulin associates with oil bodies obtained from said cell comprising oil bodies.

4. The method of claim 1 wherein said multimeric-immunoglobulin associates intracellularly with said oil bodies.

5. The method of claim 1 wherein said second immunoglobulin-polypeptide-chain is associated with a second oil-body-targeting-protein capable of associating with an oil body and said second immunoglobulin-polypeptide-chain.

6. The method of claim 5 wherein each of said first and said second oil-body-targeting-proteins is an oil-body-protein or an immunoglobulin.

7. The method of claim 6 wherein said first and said second oil-body-targeting-protein is an oleosin or caleosin.

8. The method of claim 1 wherein said oil-body-targeting-protein is an oleosin or caleosin and said first immunoglobulin-polypeptide-chain is fused to said oleosin or caleosin.

9. The method of claim 8 wherein said second immunoglobulin-polypeptide-chain is fused to a second oleosin or second caleosin capable of associating with an oil body.

10. The method of claim 1 wherein said first and second immunoglobulin-polypeptide-chains are produced as a multimeric-fusion-protein comprising said first and second immunoglobulin-polypeptide-chains.

11. The method of claim 1, wherein said first immunoglobulin-polypeptide-chain is capable of associating with said second immunoglobulin-polypeptide-chain in the cell.

12. The method of claim 1 wherein said cell is a plant cell.

13. The method of claim 1 wherein said cell is a safflower cell.

14. The method of claim 1 wherein said first immunoglobulin-polypeptide-chain is an immunoglobulin-polypeptide-light chain or an immunologically active portion thereof.

15. The method of claim 14 wherein said second immunoglobulin-polypeptide-chain is an immunoglobulin heavy chain, or an immunologically active portion thereof.

16. The method of claim 1 wherein said oil-body targeting-protein comprises immunocilobulin-binding Protein A, Protein L or Protein G.

17. A method of expressing a recombinant multimeric-immunoglobulin comprising a first and second immunoglobulin-polypeptide-chain in a cell, said method comprising:
(a) introducing into a cell a first chimeric nucleic acid sequence comprising:
(i) a first nucleic acid sequence capable of regulating transcription in said cell operatively linked to;
(ii) a second nucleic acid sequence encoding a first immunoglobulin-polypeptide-chain;
(b) introducing into said cell a second chimeric nucleic acid sequence comprising:
(i) a third nucleic acid sequence capable of regulating transcription in said cell operatively linked to;
(ii) a fourth nucleic acid sequence encoding a second immunoglobulin-polypeptide-chain;
(c) growing said cell under conditions to permit expression of said first and second immunoglobulin-polypeptide-chain in a progeny cell comprising oil bodies wherein said first recombinant immunoglobulin-polypeptide-chain and said second immunoalobulin polypeptide-chain are capable of forming a multimeric-immunoglobulin; and
(d) associating said first immunoglobulin-polypeptide-chain with an oil body through an oil-body-targeting-protein capable of associating with said oil body and said first immunoglobulin-polypeptide-chain.

18. The method of claim 17 further comprising (e) isolating from said progeny cell, oil bodies comprising said multimeric-immunoglobulin.

19. The method of claim 17 wherein said recombinant multimeric-immunoglobulin associates with said oil bodies obtained from said progeny cell comprising oil bodies.

20. The method of claim 17 wherein said oil bodies associate intracellularly with said multimeric-immunoglobulin.

21. The method of claim 17 wherein said second immunoglobulin-polypeptide-chain is associated with a second oil-body-targeting protein capable of associating with an oil body and said second immunoglobulin-polypeptide-chain.

22. The method of claim 21 wherein each of said first and said second oil-body-targeting-proteins is selected from an oil-body-protein or an immunoglobulin.

23. The method of claim 22 wherein said first and said second oil-body-protein is an oleosin or caleosin.

24. The method of claim 23 wherein said first immunoglobulin-polypeptide-chain is fused to said oleosin or caleosin.

25. The method of claim 24 wherein said second immunoglobulin-polypeptide-chain is fused to a second oleosin or second caleosin capable of associating with an oil body.

26. The method of claim 17 wherein said first and second immunoglobulin- polypeptide-chain are produced as a multimeric-fusion-protein comprising said first and second immunoglobulin-polypeptide-chain.

27. The method of claim 17 wherein said first immunoglobulin-polypeptide-chain and said second immunocilobulin polypeptide-chain are capable of forming a multimeric-immunoglobulin in said progeny cell.

28. The method of claim 17 wherein said first immunoglobulin-polypeptide-chain is an immunoglobulin-polypeptide-light chain or an immunologically active portion thereof.

29. The method of claim 28 wherein said second immunoglobulin-polypeptide is an immunoglobulin heavy chain, or an immunologically active portion thereof.

30. The method of claim 28 wherein said oil-body targeting-protein comprises immunoalobulin-bindina Protein A, Protein L or Protein G.

31. The method of claim 17 wherein said cell is a plant cell.

32. The method of claim 31 wherein said plant cell is a safflower cell.

33. A method of producing in a plant a recombinant multimeric- immunoglobulin, said method comprising:
(a) preparing a first plant comprising cells, said cells comprising oil bodies and a first immunoglobulin-polypeptide-chain wherein said first immunoglobulin-polypeptide-chain is capable of associating with said oil bodies through an oil-body-targeting-protein;
(b) preparing a second plant comprising cells, said cells comprising oil bodies and a second immunoglobulin-polypeptide-chain; and
(c) sexually crossing said first plant with said second plant to produce a progeny plant comprising cells, said cells comprising oil bodies, wherein said oil bodies are capable of associating with said first immunoglobulin-polypeptide-chain, and said first recombinant immunoglobulin polypeptide chain is capable of associating with said second immunoglobulin-polypeptide-chain to form said recombinant multimeric-immunoglobulin.

34. The method of claim 33 wherein said second immunoglobulin-polypeptide-chain is capable of associating with oil bodies through an oil-body-targeting-protein in said second plant.

35. The method of claim 33 further comprising (d) isolating from said progeny plant oil bodies comprising said multimeric-immunoglobulin.

36. The method of claim 33 wherein said oil-body-targeting-protein is selected from an oil-body-protein or an immunoglobulin.

37. The method of claim 36 wherein said oil-body-protein is an oleosin or caleosin.

38. The method of claim 37 wherein said first immunoglobulin-polypeptide-chain is fused to said oleosin or caleosin.

39. The method of claim 38 wherein said second immunoglobulin-polypeptide-chain is fused to a second oleosin or second caleosin capable of associating with an oil body.

40. The method of claim 33 wherein said first immunoglobulin-polypeptide-chain is an immunoglobulin-polypeptide-light chain or an immunologically active portion thereof.

41. The method of claim 40 wherein said second immunoglobulin-polypeptide-chain is an immunoglobulin heavy chain, or an immunologically active portion thereof.

42. The method of claim 40 wherein said oil-body targeting-protein comprises immunoalobulin-bindinci Protein A. Protein L or Protein G.

43. The method of claim 33 wherein said plant is safflower.

44. A method of producing in a plant a recombinant multimeric-immunoglobulin comprising:
   (a) preparing a first plant comprising cells, said cells comprising oil bodies and a first and second immunoglobulin-polypeptide-chain wherein said first immunoglobulin-polypeptide-chain is capable of associating with said oil bodies through an oil-body-targeting-protein;
   (b) preparing a second plant comprising cells, said cells comprising oil bodies and an oil-body-targeting-protein capable of associating with said first immunoglobulin-polypeptide-chain through said oil-body- targeting-protein; and
   (c) sexually crossing said first plant with said second plant to produce a progeny plant comprising cells, said cells comprising oil bodies, wherein said oil bodies are capable of associating with said first immunoglobulin-polypeptide-chain through an oil body-targeting-protein, and said first immunoglobulin-polypeptide-chain is capable of associating with said second immunoglobulin-polypeptide-chain to form said recombinant multimeric-immunoglobulin.

45. A method for preparing a multimeric-immunoglobulin associated with oil bodies comprising:
   a) introducing into a cell a chimeric nucleic acid sequence comprising:
      1) a first nucleic acid sequence capable of regulating transcription in said cell operatively linked to;
      2) a second nucleic acid sequence encoding a recombinant fusion polypeptide comprising (i) a nucleic acid sequence encoding a sufficient portion of an oil-body-protein to provide targeting of said recombinant fusion polypeptide to an oil body linked to (ii) a nucleic acid sequence encoding encoding a immunoglobulin comprising a first immunoglobulin-polypeptide-chain linked to a second immunoglobulin-polypeptide-chain, operatively linked to;
      3) a third nucleic acid sequence capable of terminating transcription in said cell;
   b) growing said cell under conditions to permit expression of said multimeric-immunoglobulin in a progeny cell comprising oil bodies; and
   c) isolating from said progeny cell said oil bodies comprising said multimeric-immunoglobulin.

46. A chimeric nucleic acid sequence comprising:
   1) a first nucleic acid sequence capable of regulating transcription in a host cell operatively linked to;
   2) a second nucleic acid sequence encoding a recombinant fusion polypeptide comprising (i) a nucleic acid sequence encoding a sufficient portion of an oil-body-protein to provide targeting of said recombinant fusion polypeptide to an oil body linked to (ii) a nucleic acid sequence encoding an immunoglobulin comprising a first immunoglobulin-polypeptide-chain linked to a second immunoglobulin-polypeptide-chain operatively linked to;
   3) a third nucleic acid sequence capable of terminating transcription in said cell.

47. A chimeric nucleic acid sequence encoding a multimeric-immunoglobulin-fusion-protein, said nucleic acid sequence comprising:
   (a) a first nucleic acid sequence encoding an oil-body-targeting-protein operatively linked in reading frame to;
   (b) a second nucleic acid sequence encoding a first immunoglobulin-polypeptide-chain; linked in reading frame to;
   (c) a third nucleic acid sequence encoding a second immunoglobulin-polypeptide-chain, wherein said first and second immunoglobulin-polypeptide-chain are capable of forming a multimeric-immunoglobulin.

48. The nucleic acid of claim 47, wherein said oil-body-targeting-protein is selected from an oil-body-protein or an immunoglobulin.

49. The nucleic acid of claim 48, wherein said oil-body-protein is an oleosin or caleosin.

50. The nucleic acid of claim 47, wherein said multimeric-immunoglobulin is a heteromultimeric-immunoglobulin.

51. The chimeric nucleic acid of claim 47 wherein said first immunoglobulin-polypeptide-chain is an immunoglobulin-polypeptide-light chain or an immunologically active portion thereof.

52. The chimeric nucleic acid of claim 51 wherein said second immunoglobulin-polypeptide-chain is an immunoglobulin heavy chain, or an immunologically active portion thereof.

53. The chimeric nucleic acid of claim 51 wherein said oil-body targeting-protein comprises immunoalobulin-binding Protein A, Protein L or Protein G.

54. A cell comprising oil bodies and (i) an oil-body-targeting-protein, (ii) a first immunoglobulin-polypeptide-chain and (iii) a second immunoglobulin-polypeptide-chain wherein
   (1) said first immunoglobulin-polypeptide-chain is capable of associating with said oil-body-targeting-protein; and
   (2) said first immunoglobulin-polypeptide-chain capable of associating with said second immunoglobulin-polypeptide-chain to form a multimeric-immunoglobulin.

55. The cell of claim 54 wherein said oil-body-targeting-protein is an oil-body-protein or an immunoglobulin.

56. The cell of claim 55 wherein said oil-body-protein is an oleosin or caleosin.

57. The cell of claim 54 wherein said first immunoglobulin-polypeptide-chain is fused to said second immunoglobulin-polypeptide-chain so as to form a multimeric immunoglobulin-fusion-protein.

58. The cell of claim 54 wherein said multimeric-immunoglobulin-fusion-protein is a heteromultimeric immunoglobulin -fusion-protein.

59. The cell of claim 54 wherein said first immunoglobulin-polypeptide-chain is fused to said oil-body-targeting-protein.

60. The cell of claim 54 wherein said first immunoglobulin-polypeptide-chain is fused to said first oil-body-targeting-protein and said second immunoglobulin-polypeptide-chain is fused to a second oil-body-targeting-protein.

61. The cell of claim 54 wherein said second immunoglobulin-polypeptide-chain is capable of associating with a second oil-body-targeting-protein.

62. The cell of claim 54 wherein said first and second immunoglobulin-polypeptide-chain form a heteromultimeric-immunoglobulin.

63. The cell of claim 54 wherein said first immunoglobulin-polypeptide-chain is an immunoglobulin-polypeptide-light chain or an immunologically active portion thereof.

64. The cell of claim 63 wherein said second immunoglobulin-polypeptide-chain is an immunoglobulin heavy chain, or an immunologically active portion thereof.

65. The cell of claim 54 wherein said cell is obtained from a plant.

66. The cell of claim 54 wherein said cell is obtainable from a safflower plant.

67. A plant comprising cells of claim 54.

68. Plant seed comprising cells of claim 54.

69. A safflower plant comprising cells of claim 54.

* * * * *

SEQUENCE LISTING

```
<160> NUMBER OF SEQ ID NOS: 37

<210> SEQ ID NO 1
<211> LENGTH: 27
<212> TYPE: DNA
<213> ORGANISM: Artificial Sequence
<220> FEATURE:
<223> OTHER INFORMATION: Primer #0013

<400> SEQUENCE: 1
cgcggatcca tggcggatac agctaga                                    27

<210> SEQ ID NO 2
<211> LENGTH: 25
<212> TYPE: DNA
<213> ORGANISM: Artificial Sequence
<220> FEATURE:
<223> OTHER INFORMATION: Primer #0605

<400> SEQUENCE: 2
aagcttaagt agtgtgctgg ccacc                                      25

<210> SEQ ID NO 3
<211> LENGTH: 21
<212> TYPE: DNA
<213> ORGANISM: Artificial Sequence
<220> FEATURE:
<223> OTHER INFORMATION: Primer #1020

<400> SEQUENCE: 3
ctgtcagtaa ctgcaggtgt c                                          21

<210> SEQ ID NO 4
<211> LENGTH: 21
<212> TYPE: DNA
<213> ORGANISM: Artificial Sequence
<220> FEATURE:
<223> OTHER INFORMATION: Primer #1021

<400> SEQUENCE: 4
gtaggtgtca gagtcctgta g                                          21

<210> SEQ ID NO 5
<211> LENGTH: 21
<212> TYPE: DNA
<213> ORGANISM: Artificial Sequence
<220> FEATURE:
<223> OTHER INFORMATION: Primer #1022

<400> SEQUENCE: 5
tctgggtatc tggtrcstgt g                                          21

<210> SEQ ID NO 6
<211> LENGTH: 21
<212> TYPE: DNA
<213> ORGANISM: Artificial Sequence
```

```
<220> FEATURE:
<223> OTHER INFORMATION: Primer #1023

<400> SEQUENCE: 6
gcaacagtgg taggtcgctt g                                      21

<210> SEQ ID NO 7
<211> LENGTH: 31
<212> TYPE: DNA
<213> ORGANISM: Artificial Sequence
<220> FEATURE:
<223> OTHER INFORMATION: Primer #1207

<400> SEQUENCE: 7
gcgcagatct aacatgaact ttctcaagtc c                           31

<210> SEQ ID NO 8
<211> LENGTH: 49
<212> TYPE: DNA
<213> ORGANISM: Artificial Sequence
<220> FEATURE:
<223> OTHER INFORMATION: Primer #1208

<400> SEQUENCE: 8
gtccgaaaca gaggaaagcg tagaatggaa aggacttgag aaagttcat        49

<210> SEQ ID NO 9
<211> LENGTH: 45
<212> TYPE: DNA
<213> ORGANISM: Artificial Sequence
<220> FEATURE:
<223> OTHER INFORMATION: Primer #1209

<400> SEQUENCE: 9
gctttcctct gtttcggaca atactttgtt gctgtcactc acgct            45

<210> SEQ ID NO 10
<211> LENGTH: 38
<212> TYPE: DNA
<213> ORGANISM: Artificial Sequence
<220> FEATURE:
<223> OTHER INFORMATION: Primer #1210

<400> SEQUENCE: 10
gactgctgca ggtgaacctg agcgtgagtg acagcaac                    38

<210> SEQ ID NO 11
<211> LENGTH: 29
<212> TYPE: DNA
<213> ORGANISM: Artificial Sequence
<220> FEATURE:
<223> OTHER INFORMATION: Primer #1211

<400> SEQUENCE: 11
gcgcagatct tcatttacca ggagagtgg                              29

<210> SEQ ID NO 12
<211> LENGTH: 38
<212> TYPE: DNA
<213> ORGANISM: Artificial Sequence
<220> FEATURE:
<223> OTHER INFORMATION: Primer #1202

<400> SEQUENCE: 12
gcgcctcgag atctaccatg aacttcctca gtctttc                     38
```

<210> SEQ ID NO 13
<211> LENGTH: 49
<212> TYPE: DNA
<213> ORGANISM: Artificial Sequence
<220> FEATURE:
<223> OTHER INFORMATION: Primer #1203

<400> SEQUENCE: 13
gaccaaagca gagaaaagca taaaacggga aagacttgag gaagttcat               49

<210> SEQ ID NO 14
<211> LENGTH: 45
<212> TYPE: DNA
<213> ORGANISM: Artificial Sequence
<220> FEATURE:
<223> OTHER INFORMATION: Primer #1204

<400> SEQUENCE: 14
gcttttctct gctttggtca gtatttcgtc gctgttaccc atgct                   45

<210> SEQ ID NO 15
<211> LENGTH: 39
<212> TYPE: DNA
<213> ORGANISM: Artificial Sequence
<220> FEATURE:
<223> OTHER INFORMATION: Primer #1205

<400> SEQUENCE: 15
gactgtgtca tcacaatgtc agcatgggta acagcgacg                          39

<210> SEQ ID NO 16
<211> LENGTH: 37
<212> TYPE: DNA
<213> ORGANISM: Artificial Sequence
<220> FEATURE:
<223> OTHER INFORMATION: Primer #1206

<400> SEQUENCE: 16
gcgcagatct cgagctaaca ctcattcctg ttgaagc                            37

<210> SEQ ID NO 17
<211> LENGTH: 3344
<212> TYPE: DNA
<213> ORGANISM: Artificial Sequence
<220> FEATURE:
<223> OTHER INFORMATION: The Linin promoter-secretion signal D9 light
     chain - linin terminator cassette
<220> FEATURE:
<221> NAME/KEY: exon
<222> LOCATION: (2054)..(2790)
<223> OTHER INFORMATION:

<400> SEQUENCE: 17
acgcgtctca agcatacgga caagggtaaa taacatagtc accagaacat aataaacaaa    60
aagtgcagaa gcaagactaa aaaaattagc tatggacatt caggttcata ttggaaacat   120
cattatccta gtcttgtgac catccttcct cctgctctag ttgagaggcc ttgggactaa   180
cgagaggtca gttgggatag cagatcctta tcctggacta gcctttctgg tgtttcagag   240
tcttcgtgcc gccgtctaca tctatctcca ttaggtctga agatgactct tcacaccaac   300
gacgtttaag gtctctatcc tactcctagc ttgcaatacc tggcttgcaa tacctggagc   360
atcgtgcacg atgattggat actgtggagg aggagtgttt gctgatttag agctcccggt   420
tgggtgattt gacttcgatt tcagtttagg cttgttgaaa ttttttcaggt tccattgtga   480

```
agcctttaga gcttgagctt ccttccatgt taatgccttg atcgaattct cctagagaaa       540
agggaagtcg atctctgagt attgaaatcg aagtgcacat ttttttttca cgtgtccaat       600
caatccacaa acaaagcaga agacaggtaa tctttcatac ttatactgac aagtaatagt       660
cttaccgtca tgcataataa cgtctcgttc cttcaagagg ggttttccga catccataac       720
gacccgaagc tcatgaaag cattagggaa gaacttttgg ttcttcttgt catggccttt       780
ataggtgtca gccgagctcg ccaattcccg tccgactggc tccgcaaaat attcgaacgg       840
caagttatgg acttgcaacc ataactccac ggtattgagc aggacctatt gtgaagactc       900
atctcatgga gcttcagaat gtggttgtca gcaaaccaat gaccgaaatc catcacatga       960
cggacgtcca gtgggtgagc gaaacgaaac aggaagcgcc tatctttcag agtcgtgagc      1020
tccacaccgg attccggcaa ctacgtgttg ggcaggcttc gccgtattag agatatgttg      1080
aggcagaccc atctgtgcca ctcgtacaat tacgagagtt gttttttttg tgattttcct      1140
agtttctcgt tgatggtgag ctcatattct acatcgtatg gtctctcaac gtcgtttcct      1200
gtcatctgat atcccgtcat ttgcatccac gtgcgccgcc tcccgtgcca agtccctagg      1260
tgtcatgcac gccaaattgg tggtggtgcg ggctgccctg tgcttcttac cgatgggtgg      1320
aggttgagtt tgggggtctc cgcggcgatg gtagtgggtt gacggtttgg tgtgggttga      1380
cggcattgat caatttactt cttgcttcaa attctttggc agaaaacaat tcattagatt      1440
agaactggaa accagagtga tgagacggat taagtcagat tccaacagag ttacatctct      1500
taagaaataa tgtaacccct ttagacttta tatatttgca attaaaaaaa taatttaact      1560
tttagacttt atatatagtt ttaataacta agtttaacca ctctattatt tatatcgaaa      1620
ctatttgtat gtctccctc taaataaact tggtattgtg tttacagaac ctataatcaa      1680
ataatcaata ctcaactgaa gttgtgcag ttaattgaag ggattaacgg ccaaaatgca      1740
ctagtattat caaccgaata gattcacact agatggccat ttccatcaat atcatcgccg      1800
ttcttcttct gtccacatat cccctctgaa acttgagaga cacctgcact tcattgtcct      1860
tattacgtgt tacaaaatga aacccatgca tccatgcaaa ctgaagaatg gcgcaagaac      1920
ccttcccctc catttcttat gtggcgacca tccatttcac catctcccgc tataaaacac      1980
ccccatcact tcacctagaa catcatcact acttgcttat ccatccaaaa gatacccacc      2040
ctcgagatct acc atg aac ttc ctc aag tct ttc ccg ttt tat gct ttt       2089
             Met Asn Phe Leu Lys Ser Phe Pro Phe Tyr Ala Phe
             1               5                  10 ctc tgc ttt ggt cag tat ttc gtc gct gtt acc cat gct gac att gtg       2137
Leu Cys Phe Gly Gln Tyr Phe Val Ala Val Thr His Ala Asp Ile Val
        15                  20                  25 atg aca cag tct cca tcc tcc ctg gct atg tca gtg gga cag cgg gtc       2185
Met Thr Gln Ser Pro Ser Ser Leu Ala Met Ser Val Gly Gln Arg Val
30                  35                  40 act atg cgc tgc aag tcc agt cag agc ctt tta aaa agt acc aat caa       2233
Thr Met Arg Cys Lys Ser Ser Gln Ser Leu Leu Lys Ser Thr Asn Gln
45                  50                  55                  60 aag aac tat ttg gcc tgg tac cag cag aaa cca gga cag tct cct aaa       2281
Lys Asn Tyr Leu Ala Trp Tyr Gln Gln Lys Pro Gly Gln Ser Pro Lys
                65                  70                  75 ctt ctg gta tac ttt gca tcc act agg gaa tct ggg gtc cct gat cgc       2329
Leu Leu Val Tyr Phe Ala Ser Thr Arg Glu Ser Gly Val Pro Asp Arg
            80                  85                  90 ttc ata ggc agt gga tct ggg aca gat ttc act ctt acc atc agc agt       2377
Phe Ile Gly Ser Gly Ser Gly Thr Asp Phe Thr Leu Thr Ile Ser Ser
        95                  100                 105
```

```
gtg cag gct gaa gac ctg gca gat tac ttc tgt cag caa cat tat aac       2425
Val Gln Ala Glu Asp Leu Ala Asp Tyr Phe Cys Gln Gln His Tyr Asn
    110             115                 120 act cct ccc acg ttc ggt gct ggg acc aag ctg gag ctg aaa cgg gct       2473
Thr Pro Pro Thr Phe Gly Ala Gly Thr Lys Leu Glu Leu Lys Arg Ala
125             130                 135                 140 gat gct gca cca act gta tcc atc ttc cca cca tcc agt gag cag tta       2521
Asp Ala Ala Pro Thr Val Ser Ile Phe Pro Pro Ser Ser Glu Gln Leu
                145                 150                 155 aca tct gga ggt gcc tca gtc gtg tgc ttc ttg aac aac ttc tac ccc       2569
Thr Ser Gly Gly Ala Ser Val Val Cys Phe Leu Asn Asn Phe Tyr Pro
            160                 165                 170 aaa gac atc aat gtc aag tgg aag att gat ggc agt gaa cga caa aat       2617
Lys Asp Ile Asn Val Lys Trp Lys Ile Asp Gly Ser Glu Arg Gln Asn
        175                 180                 185 ggc gtc ctg aac agt tgg act gat cag gac agc aaa gac agc acc tac       2665
Gly Val Leu Asn Ser Trp Thr Asp Gln Asp Ser Lys Asp Ser Thr Tyr
    190                 195                 200 agc atg agc agc acc ctc acg ttg acc aag gac gag tat gaa cga cat       2713
Ser Met Ser Ser Thr Leu Thr Leu Thr Lys Asp Glu Tyr Glu Arg His
205             210                 215                 220 aac agc tat acc tgt gag gcc act cac aag aca tca act tca ccc att       2761
Asn Ser Tyr Thr Cys Glu Ala Thr His Lys Thr Ser Thr Ser Pro Ile
                225                 230                 235 gtc aag agc ttc aac agg aat gag tgt ta gctcgagcaa gcttatgtga          2810
Val Lys Ser Phe Asn Arg Asn Glu Cys
            240                 245 cgtgaaataa taacggtaaa atatatgtaa taataataat aataaagcca caaagtgaga    2870
atgaggggaa ggggaaatgt gtaatgagcc agtagccggt ggtgctaatt ttgtatcgta    2930
ttgtcaataa atcatgaatt ttgtggtttt tatgtgtttt tttaaatcat gaattttaaa    2990
ttttataaaa taatctccaa tcggaagaac aacattccat atccatgcat ggatgtttct    3050
ttacccaaat ctagttcttg agaggatgaa gcatcaccga acagttctgc aactatccct    3110
caaaagcttt aaaatgaaca acaaggaaca gagcaacgtt ccaaagatcc caaacgaaac    3170
atattatcta tactaatact atattattaa ttactactgc ccggaatcac aatccctgaa    3230
tgattcctat taactacaag ccttgttggc ggcggagaag tgatcggcgc ggcgagaagc    3290
agcggactcg gagacgaggc cttggatgag cagagtcttt acctgccaac gcgt          3344

<210> SEQ ID NO 18
<211> LENGTH: 4191
<212> TYPE: DNA
<213> ORGANISM: Artificial Sequence
<220> FEATURE:
<223> OTHER INFORMATION: Phaseolin D9 heavy chain cassette
<220> FEATURE:
<221> NAME/KEY: exon
<222> LOCATION: (1564)..(2953)
<223> OTHER INFORMATION:

<400> SEQUENCE: 18
ctgcagacgc gtattgtact cccagtatca ttatagtgaa agttttggct ctctcgccgg      60 tggttttta cctctattta aagggttttt ccacctaaaa attctggtat cattctcact     120
ttacttgtta ctttaatttc tcataatctt tggttgaaat tatcacgctt ccgcacacga    180
tatccctaca aatttattat ttgttaaaca ttttcaaacc gcataaaatt ttatgaagtc    240
ccgtctatct ttaatgtagt ctaacatttt catattgaaa tatataattt acttaatttt    300
```

```
                                                               -continued agcgttggta gaaagcataa tgatttattc ttattcttct tcatataaat gtttaatata    360
caatataaac aaattcttta ccttaagaag gatttcccat tttatatttt aaaaatatat    420
ttatcaaata ttttcaacc acgtaaatct cataataata agttgtttca aaagtaataa     480
aatttaactc cataatttt ttattcgact gatcttaaag caacacccag tgacacaact     540
agccattttt ttctttgaat aaaaaaatcc aattatcatt gtatttttt tatacaatga     600 aaatttcacc aaacaatgat ttgtggtatt tctgaagcaa gtcatgttat gcaaaattct    660
ataattccca tttgacacta cggaagtaac tgaagatctg cttttacatg cgagacacat    720
cttctaaagt aattttaata atagttacta tattcaagat ttcatatatc aaatactcaa    780
tattacttct aaaaaattaa ttagatataa ttaaaatatt acttttttaa ttttaagttt    840
aattgttgaa tttgtgacta ttgatttatt attctactat gtttaaattg ttttatagat    900
agtttaaagt aaatataagt aatgtagtag agtgttagag tgttacccta aaccataaac    960
tataagattt atggtggact aattttcata tatttcttat tgcttttacc ttttcttggt   1020
atgtaagtcc gtaactggaa ttactgtggg ttgccatgac actctgtggt cttttggttc   1080
atgcatggat gcttgcgcaa gaaaaagaca agaacaaag aaaaaagaca aaacagagag    1140
acaaaacgca atcacacaac caactcaaat tagtcactgg ctgatcaaga tcgccgcgtc   1200
catgtatgtc taaatgccat gcaaagcaac acgtgcttaa catgcacttt aaatggctca   1260
cccatctcaa cccacacaca aacacattgc cttttcttc atcatcacca caaccacctg    1320
tatatattca ttctcttccg ccacctcaat ttcttcactt caacacacgt caacctgcat   1380
atgcgtgtca tcccatgccc aaatctccat gcatgttcca accaccttct ctcttatata   1440 ataccctataa ataccctcaa tatcactcac ttctttcatc atccatccat ccagagtact   1500
actactctac tactataata ccccaaccca actcatattc aatactactc taccggatct    1560 aac atg aac ttt ctc aag tcc ttt cca ttc tac gct ttc ctc tgt ttc    1608
    Met Asn Phe Leu Lys Ser Phe Pro Phe Tyr Ala Phe Leu Cys Phe
    1               5                   10                  15 gga caa tac ttt gtt gct gtc act cac gct cag gtt cac ctg cag cag    1656
Gly Gln Tyr Phe Val Ala Val Thr His Ala Gln Val His Leu Gln Gln
            20                  25                  30 tct gga gct gag ctg atg aag cct ggg gcc tca atg aag ata tcc tgc    1704
Ser Gly Ala Glu Leu Met Lys Pro Gly Ala Ser Met Lys Ile Ser Cys
        35                  40                  45 aag gct act ggc tac aca ttc agt agc tac tgg ata gag tgg gta aag    1752
Lys Ala Thr Gly Tyr Thr Phe Ser Ser Tyr Trp Ile Glu Trp Val Lys
    50                  55                  60 cag agg cct gga cat ggc ctt gag tgg att gga gag att tta cct ggc    1800
Gln Arg Pro Gly His Gly Leu Glu Trp Ile Gly Glu Ile Leu Pro Gly
65                  70                  75 agt ggt agt act acc tac aat gag aag ttc aag ggc aag gcc aca ttc    1848
Ser Gly Ser Thr Thr Tyr Asn Glu Lys Phe Lys Gly Lys Ala Thr Phe
80                  85                  90                  95 act gca gat aca tcc tcc aac aca gcc tac atg caa ctc agc agc ctg    1896
Thr Ala Asp Thr Ser Ser Asn Thr Ala Tyr Met Gln Leu Ser Ser Leu
                100                 105                 110 aca tct gag gac tct gcc gtc tat tac tgt gca aga ttg gat gtt gac    1944
Thr Ser Glu Asp Ser Ala Val Tyr Tyr Cys Ala Arg Leu Asp Val Asp
            115                 120                 125 tcc tgg ggc caa ggc acc act ctc aca gtc tcc tca gcc aaa acg aca    1992
Ser Trp Gly Gln Gly Thr Thr Leu Thr Val Ser Ser Ala Lys Thr Thr
        130                 135                 140 ccc cca tct gtc tat cca ctg gcc cct gga tct gct gcc caa act aac    2040
```

-continued

```
Pro Pro Ser Val Tyr Pro Leu Ala Pro Gly Ser Ala Ala Gln Thr Asn
    145                 150                 155 tcc atg gtg acc ctg gga tgc ctg gtc aag ggc tat ttc cct gag cca      2088
Ser Met Val Thr Leu Gly Cys Leu Val Lys Gly Tyr Phe Pro Glu Pro
160                 165                 170                 175 gtg aca gtg acc tgg aac tct gga tcc ctg tcc agc ggt gtg cac acc      2136
Val Thr Val Thr Trp Asn Ser Gly Ser Leu Ser Ser Gly Val His Thr
                180                 185                 190 ttc cca gct gtc ctg cag tct gac ctc tac act ctg agc agc tca gtg      2184
Phe Pro Ala Val Leu Gln Ser Asp Leu Tyr Thr Leu Ser Ser Ser Val
            195                 200                 205 act gtc ccc tcc agc acc tgg ccc agc gag acc gtc acc tgc aac gtt      2232
Thr Val Pro Ser Ser Thr Trp Pro Ser Glu Thr Val Thr Cys Asn Val
        210                 215                 220 gcc cac ccg gcc agc agc acc aag gtg gac aag aaa att gtg ccc agg      2280
Ala His Pro Ala Ser Ser Thr Lys Val Asp Lys Lys Ile Val Pro Arg
    225                 230                 235 gat tgt ggt tgt aag cct tgc ata tgt aca gtc cca gaa gta tca tct      2328
Asp Cys Gly Cys Lys Pro Cys Ile Cys Thr Val Pro Glu Val Ser Ser
240                 245                 250                 255 gtc ttc atc ttc ccc cca aag ccc aag gat gtg ctc acc att act ctg      2376
Val Phe Ile Phe Pro Pro Lys Pro Lys Asp Val Leu Thr Ile Thr Leu
                260                 265                 270 act cct aag gtc acg tgt gtt gtg gta gac atc agc aag gat gat ccc      2424
Thr Pro Lys Val Thr Cys Val Val Val Asp Ile Ser Lys Asp Asp Pro
            275                 280                 285 gag gtc cag ttc agc tgg ttt gta gat gat gtg gag gtg cac aca gct      2472
Glu Val Gln Phe Ser Trp Phe Val Asp Asp Val Glu Val His Thr Ala
        290                 295                 300 cag acg caa ccc cgg gag gag cag ttc aac agc act ttc cgc tca gtc      2520
Gln Thr Gln Pro Arg Glu Glu Gln Phe Asn Ser Thr Phe Arg Ser Val
    305                 310                 315 agt gaa ctt ccc atc atg cac cag gac tgg ctc aat ggc aag gag ttc      2568
Ser Glu Leu Pro Ile Met His Gln Asp Trp Leu Asn Gly Lys Glu Phe
320                 325                 330                 335 aaa tgc agg gtc aac agt gca gct ttc cct gcc ccc atc gag aaa acc      2616
Lys Cys Arg Val Asn Ser Ala Ala Phe Pro Ala Pro Ile Glu Lys Thr
                340                 345                 350 atc tcc aaa acc aaa ggc aga ccg aag gct cca cag gtg tac acc att      2664
Ile Ser Lys Thr Lys Gly Arg Pro Lys Ala Pro Gln Val Tyr Thr Ile
            355                 360                 365 cca cct ccc aag gag cag atg gcc aag gat aaa gtc agt ctg acc tgc      2712
Pro Pro Pro Lys Glu Gln Met Ala Lys Asp Lys Val Ser Leu Thr Cys
        370                 375                 380 atg ata aca gac ttc ttc cct gaa gac att act gtg gag tgg cag tgg      2760
Met Ile Thr Asp Phe Phe Pro Glu Asp Ile Thr Val Glu Trp Gln Trp
    385                 390                 395 aat ggg cag cca gcg gag aac tac aag aac act cag ccc atc atg gac      2808
Asn Gly Gln Pro Ala Glu Asn Tyr Lys Asn Thr Gln Pro Ile Met Asp
400                 405                 410                 415 aca gat ggc tct tac ttc gtc tac agc aag ctc aat gtg cag aag agc      2856
Thr Asp Gly Ser Tyr Phe Val Tyr Ser Lys Leu Asn Val Gln Lys Ser
                420                 425                 430 aac tgg gag gca gga aat act ttc acc tgc tct gtg tta cat gag ggc      2904
Asn Trp Glu Ala Gly Asn Thr Phe Thr Cys Ser Val Leu His Glu Gly
            435                 440                 445 ctg cac aac cac cat act gag aag agc ctc tcc cac tct cct ggt aaa t    2953
Leu His Asn His His Thr Glu Lys Ser Leu Ser His Ser Pro Gly Lys
        450                 455                 460
```

```
gaagatccaa gcttaaataa gtatgaacta aaatgcatgt aggtgtaaga gctcatggag      3013
agcatggaat attgtatccg accatgtaac agtataataa ctgagctcca tctcacttct      3073
tctatgaata aacaaaggat gttatgatat attaacactc tatctatgca ccttattgtt      3133
ctatgataaa tttcctctta ttattataaa tcatctgaat cgtgacggct tatggaatgc      3193
ttcaaatagt acaaaaacaa atgtgtacta aagacttcc taaacaattc taactttagc      3253
attgtgaacg agacataagt gttaagaaga cataacaatt ataatggaag aagtttgtct      3313
ccatttatat attatatatt acccacttat gtattatatt aggatgttaa ggagacataa      3373
caattataaa gagagaagtt tgtatccatt tatatattat atactaccca tttatatatt      3433
atacttatcc acttatttaa tgtctttata aggtttgatc catgatattt ctaatatttt      3493
agttgatatg tatatgaaaa ggtactattt gaactctctt actctgtata aaggttggat      3553
catccttaaa gtgggtctat ttaattttat tgcttcttac agataaaaaa aaattatgag      3613
ttggtttgat aaaatattga aggatttaaa ataataataa ataataaata acatataata      3673
tatgtatata aatttattat aatataacat ttatctataa aaaagtaaat attgtcataa      3733
atctatacaa tcgtttagcc ttgctggaac gaatctcaat tatttaaacg agagtaaaca      3793
tatttgactt tttggttatt taacaaatta ttatttaaca ctatatgaaa ttttttttt      3853 ttatcagcaa agaataaaat taaattaaga aggacaatgg tgtcccaatc cttatacaac      3913
caacttccac aagaaagtca agtcagagac aacaaaaaaa caagcaaagg aaattttta      3973 atttgagttg tcttgtttgc tgcataattt atgcagtaaa acactacaca taaccctttt      4033
agcagtagag caatggttga ccgtgtgctt agcttctttt attttatttt tttatcagca      4093 aagaataaaat aaaataaaat gagacacttc agggatgttt caacccttat acaaaacccc      4153
aaaaacaagt ttcctagcac cctaccaact aaggtacc                              4191
```

<210> SEQ ID NO 19
<211> LENGTH: 51
<212> TYPE: DNA
<213> ORGANISM: Artificial Sequence
<220> FEATURE:
<223> OTHER INFORMATION: Primer #1184 (forward)

<400> SEQUENCE: 19

```
gcacagcatg atgaagcaca gcagaatgct ttctaccagg tgctcaacat g              51
```

<210> SEQ ID NO 20
<211> LENGTH: 73
<212> TYPE: DNA
<213> ORGANISM: Artificial Sequence
<220> FEATURE:
<223> OTHER INFORMATION: Primer #1185 (reverse)

<400> SEQUENCE: 20

```
gtcgtcttta agcgattgga tgaagccgtt acgttgatca gcattgagat tgggcatgtt     60
gagcacctgg tag                                                        73
```

<210> SEQ ID NO 21
<211> LENGTH: 77
<212> TYPE: DNA
<213> ORGANISM: Artificial Sequence
<220> FEATURE:
<223> OTHER INFORMATION: Primer #1186 (forward)

<400> SEQUENCE: 21

```
ccaatcgctt aaagacgacc cttcccagag cgctaatgtc ctcggcgaag ctcaaaagct     60
```

```
gaacgacagc caagctc                                              77

<210> SEQ ID NO 22
<211> LENGTH: 78
<212> TYPE: DNA
<213> ORGANISM: Artificial Sequence
<220> FEATURE:
<223> OTHER INFORMATION: Primer #1187 (reverse)

<400> SEQUENCE: 22
ctcgtaaaag gctgactgtt gatctttgtt gaagttgttc tgttgagcat ccgcttttgg  60
agcttggctg tcgttcag                                              78

<210> SEQ ID NO 23
<211> LENGTH: 81
<212> TYPE: DNA
<213> ORGANISM: Artificial Sequence
<220> FEATURE:
<223> OTHER INFORMATION: Primer #1188 (forward)

<400> SEQUENCE: 23
cagtcagcct tttacgagat ccttaatatg cccaacctca acgaggccca gcgtaatggt  60
ttcatccaat ctcttaagga c                                          81

<210> SEQ ID NO 24
<211> LENGTH: 70
<212> TYPE: DNA
<213> ORGANISM: Artificial Sequence
<220> FEATURE:
<223> OTHER INFORMATION: Primer #1189 (reverse)

<400> SEQUENCE: 24
ctcgtttagc ttcttagctt cacccaaaac gttggtcgac tgcgatgggt cgtccttaag  60
agattggatg                                                       70

<210> SEQ ID NO 25
<211> LENGTH: 72
<212> TYPE: DNA
<213> ORGANISM: Artificial Sequence
<220> FEATURE:
<223> OTHER INFORMATION: Primer #1190 (forward)

<400> SEQUENCE: 25
gctaagaagc taaacgagtc acaggctcct aaagctgata caacttcaa caaggagcag  60 cagaacgcct tc                                                    72

<210> SEQ ID NO 26
<211> LENGTH: 75
<212> TYPE: DNA
<213> ORGANISM: Artificial Sequence
<220> FEATURE:
<223> OTHER INFORMATION: Primer #1191 (reverse)

<400> SEQUENCE: 26
ctggatgaac ccgtttcgct gttcctcgtt gagattcggc atgttgagga tttcatagaa  60
ggcgttctgc tgctc                                                 75

<210> SEQ ID NO 27
<211> LENGTH: 78
<212> TYPE: DNA
<213> ORGANISM: Artificial Sequence
<220> FEATURE:
```

<223> OTHER INFORMATION: Primer #1192 (forward)

<400> SEQUENCE: 27
cgaaacgggt tcatccagag tcttaaagat gacccatccc aatccgctaa ccttctgtct   60
gaagctaaga agctaaac                                                 78

<210> SEQ ID NO 28
<211> LENGTH: 75
<212> TYPE: DNA
<213> ORGANISM: Artificial Sequence
<220> FEATURE:
<223> OTHER INFORMATION: Primer #1193 (reverse)

<400> SEQUENCE: 28
gaaggcgttc tgttgctcct tgttaaactt gttgtcggct ttgggcgcct ggctctcgtt   60
tagcttctta gcttc                                                    75

<210> SEQ ID NO 29
<211> LENGTH: 78
<212> TYPE: DNA
<213> ORGANISM: Artificial Sequence
<220> FEATURE:
<223> OTHER INFORMATION: Primer #1194 (forward)

<400> SEQUENCE: 29
gagcaacaga acgccttcta tgaaattctg catctcccta atctcaacga ggaacaacgt   60
aacggtttca tccaatcg                                                 78

<210> SEQ ID NO 30
<211> LENGTH: 78
<212> TYPE: DNA
<213> ORGANISM: Artificial Sequence
<220> FEATURE:
<223> OTHER INFORMATION: Primer #1195 (reverse)

<400> SEQUENCE: 30
gttcagtttc ttggcctccg ccaacaagtt tgcggattga ctcggatcat ccttaagcga   60
ttggatgaaa ccgttacg                                                 78

<210> SEQ ID NO 31
<211> LENGTH: 71
<212> TYPE: DNA
<213> ORGANISM: Artificial Sequence
<220> FEATURE:
<223> OTHER INFORMATION: Primer #1196 (forward)

<400> SEQUENCE: 31
gaggccaaga aactgaacga cgcgcaagca ccaaaagctg ataacaagtt caacaaggaa   60
caacagaatg c                                                        71

<210> SEQ ID NO 32
<211> LENGTH: 73
<212> TYPE: DNA
<213> ORGANISM: Artificial Sequence
<220> FEATURE:
<223> OTHER INFORMATION: Primer #1197 (reverse)

<400> SEQUENCE: 32
gaagccgttt ctttgttcct cagtgagatt tggcaagtga agtatctcgt agaaagcatt   60
ctgttgttcc ttg                                                      73

<210> SEQ ID NO 33
<211> LENGTH: 76
<212> TYPE: DNA
<213> ORGANISM: Artificial Sequence
<220> FEATURE:
<223> OTHER INFORMATION: Primer #1198 (forward)

<400> SEQUENCE: 33
ggaacaaaga aacggcttca tccagagttt gaaggatgac ccgtctgtca gcaaggagat    60
actagctgag gcgaag                                                    76

<210> SEQ ID NO 34
<211> LENGTH: 58
<212> TYPE: DNA
<213> ORGANISM: Artificial Sequence
<220> FEATURE:
<223> OTHER INFORMATION: Primer #1199 (forward)

<400> SEQUENCE: 34
attgtcctcc tccttcggag cttgcgcatc gttcaacttc ttcgcctcag ctagtatc     58

<210> SEQ ID NO 35
<211> LENGTH: 30
<212> TYPE: DNA
<213> ORGANISM: Artificial Sequence
<220> FEATURE:
<223> OTHER INFORMATION: Primer #1024

<400> SEQUENCE: 35
gcgccatggc acagcatgat gaagcacagc                                    30

<210> SEQ ID NO 36
<211> LENGTH: 32
<212> TYPE: DNA
<213> ORGANISM: Artificial Sequence
<220> FEATURE:
<223> OTHER INFORMATION: Primer #1025

<400> SEQUENCE: 36
gcgcccatgg cattgtcctc ctccttcgga gc                                 32

<210> SEQ ID NO 37
<211> LENGTH: 4473
<212> TYPE: DNA
<213> ORGANISM: Artificial Sequence
<220> FEATURE:
<223> OTHER INFORMATION: The complete promoter-gene fusion-terminator
      cassette
<220> FEATURE:
<221> NAME/KEY: exon
<222> LOCATION: (1555)..(2799)
<223> OTHER INFORMATION:
<220> FEATURE:
<221> NAME/KEY: exon
<222> LOCATION: (3040)..(3204)
<223> OTHER INFORMATION:

<400> SEQUENCE: 37
ctgcaggaat tcattgtact cccagtatca ttatagtgaa agttttggct ctctcgccgg    60
tggtttttta cctctatttta aagggggtttt ccacctaaaa attctggtat cattctcact 120
ttacttgtta ctttaatttc tcataatctt tggttgaaat tatcacgctt ccgcacacga   180
tatccctaca aatttattat ttgttaaaca ttttcaaacc gcataaaatt ttatgaagtc   240
ccgtctatct ttaatgtagt ctaacatttt catattgaaa tatataattt acttaatttt   300
agcgttggta gaaagcataa tgatttattc ttattcttct tcatataaat gtttaatata   360

-continued

```
caatataaac aaattcttta ccttaagaag gatttcccat tttatatttt aaaaatatat    420
ttatcaaata ttttttcaacc acgtaaatct cataataata agttgtttca aaagtaataa    480
aatttaactc cataattttt ttattcgact gatcttaaag caacacccag tgacacaact    540
agccattttt ttctttgaat aaaaaaatcc aattatcatt gtattttttt tatacaatga    600
aaatttcacc aaacaatgat ttgtggtatt tctgaagcaa gtcatgttat gcaaaattct    660
ataattccca tttgacacta cggaagtaac tgaagatctg cttttacatg cgagacacat    720
cttctaaagt aattttaata atagttacta tattcaagat ttcatatatc aaatactcaa    780
tattacttct aaaaaattaa ttagatataa ttaaaatatt acttttttaa ttttaagttt    840
aattgttgaa tttgtgacta ttgatttatt attctactat gtttaaattg ttttatagat    900
agtttaaagt aaatataagt aatgtagtag agtgttagag tgttacccta aaccataaac    960
tataagattt atggtggact aattttcata tatttcttat tgcttttacc ttttcttggt   1020
atgtaagtcc gtaactggaa ttactgtggg ttgccatgac actctgtggt cttttggttc   1080
atgcatggat gcttgcgcaa gaaaaagaca agaacaaag aaaaaagaca aaacagagag   1140
acaaaacgca atcacacaac caactcaaat tagtcactgg ctgatcaaga tcgccgcgtc   1200
catgtatgtc taaatgccat gcaaagcaac acgtgcttaa catgcacttt aaatggctca   1260
cccatctcaa cccacacaca aacacattgc ctttttcttc atcatcacca caaccacctg   1320
tatatattca ttctcttccg ccacctcaat ttcttcactt caacacacgt caacctgcat   1380
atgcgtgtca tcccatgccc aaatctccat gcatgttcca accaccttct ctcttatata   1440
atacctataa atacctctaa tatcactcac ttctttcatc atccatccat ccagagtact   1500
actactctac tactataata ccccaaccca actcatattc aatactactc tacc atg     1557
                                                             Met
                                                             1 gca cag cat gat gaa gca cag cag aat gct ttc tac cag gtg ctc aac   1605
Ala Gln His Asp Glu Ala Gln Gln Asn Ala Phe Tyr Gln Val Leu Asn
        5                  10                  15 atg ccc aat tta aat gct gat caa cgt aac ggc ttc atc caa tcg ctt   1653
Met Pro Asn Leu Asn Ala Asp Gln Arg Asn Gly Phe Ile Gln Ser Leu
    20                  25                  30 aaa gac gac cct tcc cag agc gct aat gtc ctc ggc gaa gct caa aag   1701
Lys Asp Asp Pro Ser Gln Ser Ala Asn Val Leu Gly Glu Ala Gln Lys
 35                  40                  45 ctg aac gac agc caa gct cca aaa gcg gat gct caa cag aac aac ttc   1749
Leu Asn Asp Ser Gln Ala Pro Lys Ala Asp Ala Gln Gln Asn Asn Phe
 50                  55                  60                  65 aac aaa gat caa cag tca gcc ttt tac gag atc ctt aat atg ccc aac   1797
Asn Lys Asp Gln Gln Ser Ala Phe Tyr Glu Ile Leu Asn Met Pro Asn
             70                  75                  80 ctc aac gag gcc cag cgt aat ggt ttc atc caa tct ctt aag gac gac   1845
Leu Asn Glu Ala Gln Arg Asn Gly Phe Ile Gln Ser Leu Lys Asp Asp
         85                  90                  95 cca tcg cag tcg acc aac gtt ttg ggt gaa gct aag aag cta aac gag   1893
Pro Ser Gln Ser Thr Asn Val Leu Gly Glu Ala Lys Lys Leu Asn Glu
        100                 105                 110 tca cag gct cct aaa gct gat aac aac ttc aac aag gag cag cag aac   1941
Ser Gln Ala Pro Lys Ala Asp Asn Asn Phe Asn Lys Glu Gln Gln Asn
    115                 120                 125 gcc ttc tat gaa atc ctc aac atg ccg aat ctc aac gag gaa cag cga   1989
Ala Phe Tyr Glu Ile Leu Asn Met Pro Asn Leu Asn Glu Glu Gln Arg
130                 135                 140                 145
```

```
aac ggg ttc atc cag agt ctt aaa gat gac cca tcc caa tcc gct aac    2037
Asn Gly Phe Ile Gln Ser Leu Lys Asp Asp Pro Ser Gln Ser Ala Asn
            150                 155                 160 ctt ctg tct gaa gct aag aag cta aac gag agc cag gcg ccc aaa gcc    2085
Leu Leu Ser Glu Ala Lys Lys Leu Asn Glu Ser Gln Ala Pro Lys Ala
        165                 170                 175 gac aac aag ttt aac aag gag caa cag aac gcc ttc tat gaa att ctg    2133
Asp Asn Lys Phe Asn Lys Glu Gln Gln Asn Ala Phe Tyr Glu Ile Leu
    180                 185                 190 cat ctc cct aat ctc aac gag gaa caa cgt aac ggt ttc atc caa tcg    2181
His Leu Pro Asn Leu Asn Glu Glu Gln Arg Asn Gly Phe Ile Gln Ser
195                 200                 205 ctt aag gat gat ccg agt caa tcc gca aac ttg ttg gcg gag gcc aag    2229
Leu Lys Asp Asp Pro Ser Gln Ser Ala Asn Leu Leu Ala Glu Ala Lys
210                 215                 220                 225 aaa ctg aac gac gcg caa gca cca aaa gct gat aac aag ttc aac aag    2277
Lys Leu Asn Asp Ala Gln Ala Pro Lys Ala Asp Asn Lys Phe Asn Lys
            230                 235                 240 gaa caa cag aat gct ttc tac gag ata ctt cac ttg cca aat ctc act    2325
Glu Gln Gln Asn Ala Phe Tyr Glu Ile Leu His Leu Pro Asn Leu Thr
        245                 250                 255 gag gaa caa aga aac ggc ttc atc cag agt ttg aag gat gac ccg tct    2373
Glu Glu Gln Arg Asn Gly Phe Ile Gln Ser Leu Lys Asp Asp Pro Ser
    260                 265                 270 gtc agc aag gag ata cta gct gag gcg aag aag ttg aac gat gcg caa    2421
Val Ser Lys Glu Ile Leu Ala Glu Ala Lys Lys Leu Asn Asp Ala Gln
275                 280                 285 gct ccg aag gag gag gac aat gcc atg gcg gat aca gct aga gga acc    2469
Ala Pro Lys Glu Glu Asp Asn Ala Met Ala Asp Thr Ala Arg Gly Thr
290                 295                 300                 305 cat cac gat atc atc ggc aga gac cag tac ccg atg atg ggc cga gac    2517
His His Asp Ile Ile Gly Arg Asp Gln Tyr Pro Met Met Gly Arg Asp
            310                 315                 320 cga gac cag tac cag atg tcc gga cga gga tct gac tac tcc aag tct    2565
Arg Asp Gln Tyr Gln Met Ser Gly Arg Gly Ser Asp Tyr Ser Lys Ser
        325                 330                 335 agg cag att gct aaa gct gca act gct gtc aca gct ggt ggt tcc ctc    2613
Arg Gln Ile Ala Lys Ala Ala Thr Ala Val Thr Ala Gly Gly Ser Leu
    340                 345                 350 ctt gtt ctc tcc agc ctt acc ctt gtt gga act gtc ata gct ttg act    2661
Leu Val Leu Ser Ser Leu Thr Leu Val Gly Thr Val Ile Ala Leu Thr
355                 360                 365 gtt gca aca cct ctg ctc gtt atc ttc agc cca atc ctt gtc ccg gct    2709
Val Ala Thr Pro Leu Leu Val Ile Phe Ser Pro Ile Leu Val Pro Ala
370                 375                 380                 385 ctc atc aca gtt gca ctc ctc atc acc ggt ttt ctt tcc tct gga ggg    2757
Leu Ile Thr Val Ala Leu Leu Ile Thr Gly Phe Leu Ser Ser Gly Gly
            390                 395                 400 ttt ggc att gcc gct ata acc gtt ttc tct tgg att tac aag            2799
Phe Gly Ile Ala Ala Ile Thr Val Phe Ser Trp Ile Tyr Lys
        405                 410                 415 taagcacaca tttatcatct tacttcataa ttttgtgcaa tatgtgcatg catgtgttga   2859
gccagtagct ttggatcaat ttttttggta gaataacaaa tgtaacaata agaaattgca   2919
aattctaggg aacatttggt taactaaata cgaaatttga cctagctagc ttgaatgtgt   2979
ctgtgtatat catctatata ggtaaaatgc ttggtatgat acctattgat tgtgaatagg   3039 tac gca acg gga gag cac cca cag gga tca gac aag ttg gac agt gca    3087
Tyr Ala Thr Gly Glu His Pro Gln Gly Ser Asp Lys Leu Asp Ser Ala
            420                 425                 430
```

```
agg atg aag ttg gga agc aaa gct cag gat ctg aaa gac aga gct cag    3135
Arg Met Lys Leu Gly Ser Lys Ala Gln Asp Leu Lys Asp Arg Ala Gln
            435                 440                 445 tac tac gga cag caa cat act ggt ggg gaa cat gac cgt gac cgt act    3183
Tyr Tyr Gly Gln Gln His Thr Gly Gly Glu His Asp Arg Asp Arg Thr
            450                 455                 460 cgt ggt ggc cag cac act act taagttaccc cactgatgtc atcgtctaga      3234
Arg Gly Gly Gln His Thr Thr
            465         470 tttaaatgca agcttaaata agtatgaact aaaatgcatg taggtgtaag agctcatgga  3294
gagcatggaa tattgtatcc gaccatgtaa cagtataata actgagctcc atctcacttc  3354
ttctatgaat aaacaaagga tgttatgata tattaacact ctatctatgc accttattgt  3414
tctatgataa atttcctctt attattataa atcatctgaa tcgtgacggc ttatggaatg  3474
cttcaaatag tacaaaaaca aatgtgtact ataagacttt ctaaacaatt ctaactttag  3534
cattgtgaac gagacataag tgttaagaag acataacaat tataatggaa gaagtttgtc  3594
tccatttata tattatatat tacccactta tgtattatat taggatgtta aggagacata  3654
acaattataa agagagaagt ttgtatccat ttatatatta tatactaccc atttatatat  3714
tatacttatc cacttattta atgtctttat aaggtttgat ccatgatatt tctaatattt  3774
tagttgatat gtatatgaaa aggtactatt tgaactctct tactctgtat aaaggttgga  3834
tcatccttaa agtgggtcta tttaatttta ttgcttctta cagataaaaa aaaattatga  3894
gttggtttga taaaatattg aaggatttaa aataataata aataataaat aacatataat  3954
atatgtatat aaatttatta taatataaca tttatctata aaaaagtaaa tattgtcata  4014
aatctataca atcgtttagc cttgctggaa cgaatctcaa ttatttaaac gagagtaaac  4074
atatttgact ttttggttat ttaacaaatt attatttaac actatatgaa attttttttt  4134
tttatcagca aagaataaaa ttaaattaag aaggacaatg gtgtcccaat ccttatacaa  4194
ccaacttcca caagaaagtc aagtcagaga caacaaaaaa acaagcaaag gaaattttt   4254 aatttgagtt gtcttgtttg ctgcataatt tatgcagtaa aacactacac ataacccttt  4314
tagcagtaga gcaatggttg accgtgtgct tagcttcttt tatttttatt ttttatcagc  4374
aaagaataaa taaaataaaa tgagacactt cagggatgtt tcaaccctta tacaaaaccc  4434
caaaaacaag tttcctagca ccctaccaac taaggtacc                        4473
```